United States Patent
Bonilla et al.

(10) Patent No.: US 12,123,048 B2
(45) Date of Patent: Oct. 22, 2024

(54) FLUORINATED 4'-ALKYLUMBELLIFERYL A-D-GLUCOPYRANOSIDES, BIOLOGICAL STERILIZATION INDICATORS INCLUDING THE SAME AND METHODS OF USING THE SAME

(71) Applicant: 3M INNOVATIVE PROPERTIES COMPANY, St. Paul, MN (US)

(72) Inventors: Tonya D. Bonilla, Woodbury, MN (US); Stephen B. Roscoe, Woodbury, MN (US); George W. Griesgraber, Eagan, MN (US)

(73) Assignee: Solventum Intellectual Property Company, Maplewood, MN (US)

( * ) Notice: Subject to any disclaimer, the term of this patent is extended or adjusted under 35 U.S.C. 154(b) by 808 days.

(21) Appl. No.: 17/298,872

(22) PCT Filed: Dec. 3, 2019

(86) PCT No.: PCT/IB2019/060408
§ 371 (c)(1),
(2) Date: Jun. 1, 2021

(87) PCT Pub. No.: WO2020/115661
PCT Pub. Date: Jun. 11, 2020

(65) Prior Publication Data
US 2022/0017939 A1   Jan. 20, 2022

Related U.S. Application Data

(60) Provisional application No. 62/776,308, filed on Dec. 6, 2018.

(51) Int. Cl.
*C07H 17/075*   (2006.01)
*A61L 2/28*   (2006.01)
(Continued)

(52) U.S. Cl.
CPC .................. *C12Q 1/22* (2013.01); *A61L 2/28* (2013.01); *C07H 17/075* (2013.01); *G01N 21/6428* (2013.01); *G01N 2021/6439* (2013.01)

(58) Field of Classification Search
CPC ........... C12Q 1/22; A61L 2/28; C07H 17/075; G01N 21/6428; G01N 2021/6439
See application file for complete search history.

(56) References Cited

U.S. PATENT DOCUMENTS 5,073,488 A   12/1991 Matner
5,830,912 A   11/1998 Gee
(Continued)

FOREIGN PATENT DOCUMENTS

WO   WO 2004-000569   12/2003
WO   WO 2005-013308   2/2005
(Continued)

OTHER PUBLICATIONS

Ahmed, "A fluorogenic substrate for the continuous assaying of aryl sulfatases", Analytical Biochemistry, 2005, vol. 340, No. 1, pp. 80-88.
(Continued)

*Primary Examiner* — Medhanit W Bahta

(57) ABSTRACT

A self-contained biological sterilization indicator comprises: a housing; bacterial spores comprising, and/or capable of producing, an enzyme capable of catalyzing cleavage of an enzyme substrate; and a frangible container containing a composition, wherein the composition comprises the enzyme substrate, wherein if the frangible container is broken the composition will contact the bacterial spores to form a mixture having an initial pH in the range from 6.0 to 9.0. The enzyme substrate comprises a fluorinated 4'-alky-
(Continued)

lumbelliferyl α-D-glucopyranoside represented by the structural formula (I) wherein one of $R^1$ and $R^2$ is F and the other is H, and $R^3$ is an alkyl group having from 1 to 12 carbon atoms. A biological sterilization indicator comprising a kit containing isolated components comprising (i) bacterial spores comprising, and/or capable of producing, an enzyme capable of catalyzing cleavage of the enzyme substrate and a method of assessing efficacy of a sterilization process are also disclosed.

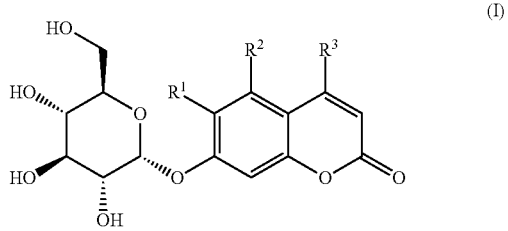

(I)

24 Claims, 6 Drawing Sheets

(51) Int. Cl.
  *C12Q 1/22* (2006.01)
  *G01N 21/64* (2006.01)

(56) References Cited

U.S. PATENT DOCUMENTS

| | | | |
|---|---|---|---|
| 6,623,955 B2 | 9/2003 | Matner | |
| 7,026,491 B2 | 4/2006 | Cheng | |
| 8,840,837 B2 | 9/2014 | Smith | |
| 8,980,622 B2 | 3/2015 | Smith | |
| 9,040,714 B2 | 5/2015 | Zeng | |
| 9,145,573 B2 | 9/2015 | Pederson | |
| 9,322,046 B2 | 4/2016 | Chandrapati | |
| 9,410,180 B2 | 8/2016 | Pederson | |
| 9,434,975 B2 | 9/2016 | Roscoe | |
| 2003/0235677 A1 | 12/2003 | Hanschen | |
| 2010/0267653 A1* | 10/2010 | Stewart | A61P 31/10 536/18.1 |
| 2016/0102335 A1* | 4/2016 | Franciskovich | C12M 1/34 435/31 |
| 2017/0218428 A1 | 8/2017 | Witcher | |

FOREIGN PATENT DOCUMENTS

| | | | |
|---|---|---|---|
| WO | WO 2007-070310 | 6/2007 | |
| WO | WO 2008-079469 | 7/2008 | |
| WO | WO 2011-087711 | 7/2011 | |
| WO | WO 2011-127070 | 10/2011 | |
| WO | WO 2012-061229 | 5/2012 | |
| WO | WO 2016-060714 | 4/2016 | |
| WO | WO-2019094631 A1 * | 5/2019 | ......... A61K 31/7034 |
| WO | WO 2019-123156 | 6/2019 | |
| WO | WO 2019-123217 | 6/2019 | |
| WO | WO 2020-023833 | 1/2020 | |

OTHER PUBLICATIONS

Chan, "Turnover is Rate-Limited by Deglycosylation for Micromonospora viridifaciens Sialidase-Catalyzed Hydrolyses: Conformational Implications for the Michaelis Complex". Journal of the American Chemical Society, Mar. 2011, vol. 133, No. 9, pp. 2989-2997.
Dubiella, "Tunable Probes with Direct Fluorescence Signals for the Constitutive and Immunoproteasome", Angewandte Chemie (International ed.), Oct. 2016, vol. 55, No. 42, pp. 13330-13334.
Fjeld, "Kinetic Analysis of Human Serine/Threonine Protein Phosphatase 2Cα*", The Journal of Biological Chemistry, Jul. 1999, vol. 274, No. 29, pp. 20336-20343.
Ge, "An ultrasensitive, continuous assay for xylanase using the fluorogenic substrate 6,8-difluoro-4-methylumbelliferyl β-D-xylobioside", Analytical Biochemistry, 2007, vol. 362, No. 1, pp. 63-68.
Gee, "Fluorogenic Substrates Based on Fluorinated Umbelliferones for Continuous Assays of Phosphatases and b-Galactosidases", Analytical Biochemistry, 1999, vol. 273, pp. 41-48.
Roth, "Methods of Biochemical Analysis—vol. 17" Table of Content, 1969, 3 Pages.
Roth, "Methods of Biochemical Analysis—vol. 7" Table of Content, 1959, 9 Pages.
Setlow, "Analysis of a-glucosidase enzyme activity used in a rapid test for steam sterilization assurance" Journal of Applied Microbiology, May 2016, vol. 120, No. 5, pp. 1326-1335.
Sun, "Synthesis of Fluorinated Fluoresceins", Journal of Organic Chemistry, Sep. 1997, vol. 62, No. 19, pp. 6469-6475.
Sun, "Synthesis of Novel Fluorinated Coumarins: Excellent UV-Light Excitable Fluorescent Dyes", Bioorganic & Medicinal Chemistry Letters, 1998, vol. 8, pp. 3107-3110.
Yeung, "Kinetic and Structural Evaluation of Selected Active Site Mutants of the Aspergillus fumigatus KDNase (Sialidase)", Biochemistry (Easton), Dec. 2013, vol. 52, No. 51, pp. 9177-9186.
International Search Report for PCT International Application No. PCT/IB2019/060408, mailed on Mar. 11, 2020, 3 pages.

* cited by examiner

FLUORINATED 4'-ALKYLUMBELLIFERYL A-D-GLUCOPYRANOSIDES, BIOLOGICAL STERILIZATION INDICATORS INCLUDING THE SAME AND METHODS OF USING THE SAME

CROSS-REFERENCE TO RELATED APPLICATIONS

This application is a national stage filing under 35 U.S.C. 371 of PCT/IB2019/060408, filed Dec. 3, 2019, which claims the benefit of U.S. Provisional Application No. 62/776,308, filed Dec. 6, 2018.

TECHNICAL FIELD

The present disclosure broadly relates to fluorinated 4'-alkylumbelliferyl α-D-glucopyranosides, biological sterilization indicators including the same and methods of using the same.

BACKGROUND

Biological sterilization indicators (biological indicators) provide a means for determining whether a sterilizing machine, such as those used to sterilize surgical instruments in hospitals, is functioning properly and killing microorganisms that are present in the sterilization chamber during a sterilization procedure.

Biological indicators are recognized in the art as providing an accurate and precise means for testing the effectiveness of a sterilization procedure. In contrast to sterilization indicators that measure spore outgrowth alone, biological indicators that measure the activity of an enzyme whose activity is correlated with the destruction of contaminating microorganisms during a sterilization procedure provide a faster result. For example, Geobacillus stearothermophilus α-glucosidase activity correlates with the loss or maintenance of spore viability post-sterilization, which provides test results within minutes to hours instead of days (growth-based detection readings).

In one method, the substrate 4'-methylumbelliferyl-α-D-glucopyranoside (MUG, shown below):

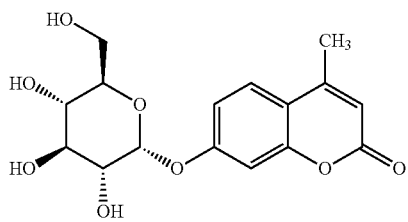

is incorporated into a detection medium. Once in contact with the medium, a spore-derived enzyme rapidly hydrolyzes the substrate to release the intensely fluorescent molecule 4-methylumbelliferone, shown below.

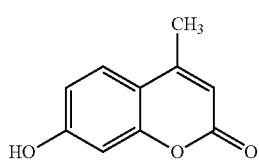

The deprotonated form of 4-methylumbelliferone ($pK_a$=7.8), shown below:

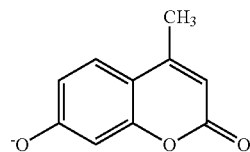

Highest fluorescence is observed in its deprotonated anionic form, typically having a greater fluorescence intensity at pH=10 than at a pH of 6-8, when excited at 360 nanometers (nm), with an emission maximum of 455 nm. However, a pH of 6-8 is typically desired for the detection of α-glucosidase activity from Geobacillus stearothermophilus endospores.

Detection of α-glucosidase activity is often preferred for detection of G. stearothermophilus in biological indicators used to monitor sterilization protocols; for example, as described in U.S. Pat. No. 5,073,488 (Matner et al.).

Using MUG substrate, the enzyme can be detected within short time-frames from fractional kill sterilization cycles. Another significant advantage of using this system for biological sterilization indicators, in particular self-contained steam sterilization biological sterilization indicators, is that MUG substrate can tolerate high heat exposures.

SUMMARY

There is a need for materials (e.g., enzyme substrates) that provide improved sensitivity in bioassay applications that currently use 4'-methylumbelliferyl α-D-glucopyranoside (MUG) to monitor G. stearothermophilus α-glucosidase activity by continuous fluorescence detection in culture media and buffer solutions, preferably at a pH of 6 to 9, more preferably 6 to 8.

Accordingly, in one aspect, the present disclosure provides a fluorinated 4'-alkylumbelliferyl α-D-glucopyranoside represented by the structural formula

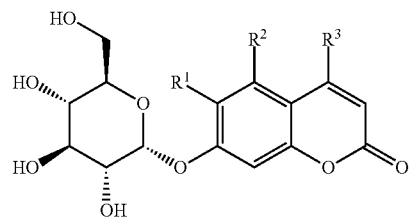

wherein one of $R^1$ and $R^2$ is F and the other is H, and $R^3$ is an alkyl group having from 1 to 12 carbon atoms. Fluorinated 4'-alkylumbelliferyl α-D-glucopyranosides according to the preceding structural formula are useful as enzyme substrates in certain biological sterilization indicators, especially those utilizing α-glucosidase produced by G. stearothermophilus.

In another aspect, the present disclosure provides a self-contained biological sterilization indicator comprising:

a housing, bacterial spores comprising, and/or capable of producing, an enzyme capable of catalyzing cleavage of an enzyme substrate represented by the structural formula

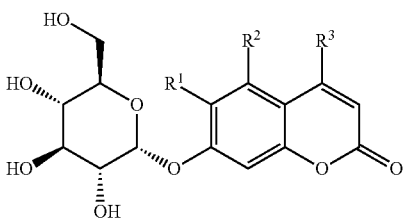

wherein:
one of R¹ and R² is F and the other is H, and
R³ is an alkyl group having from 1 to 12 carbon atoms; and
a frangible container containing a composition, wherein the composition comprises the enzyme substrate, wherein if the frangible container is broken the composition will contact the bacterial spores to form a mixture having an initial pH in the range from 6.0 to 9.0.

In yet another aspect, the present disclosure provides a biological sterilization indicator comprising a kit containing isolated components comprising:
(i) bacterial spores comprising, and/or capable of producing, an enzyme capable of catalyzing cleavage of an enzyme substrate represented by the structural formula

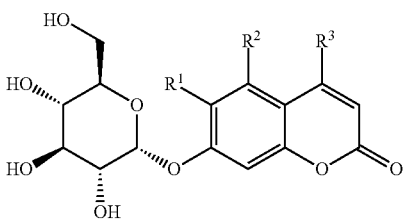

wherein:
one of R¹ and R² is F and the other is H, and
R³ is an alkyl group having from 1 to 12 carbon atoms; and
(ii) a composition, wherein the composition comprises the enzyme substrate, wherein if the composition is brought into contact with the bacterial spores to form a mixture, the mixture will have an initial pH in the range from 6.0 to 9.0.

In yet another aspect, the present disclosure provides a method of assessing efficacy of a sterilization process, the method comprising sequentially:
a) providing a biological sterilization indicator comprising:
bacterial spores comprising, and/or capable of producing, an enzyme capable of catalyzing cleavage of an enzyme substrate represented by the structural formula

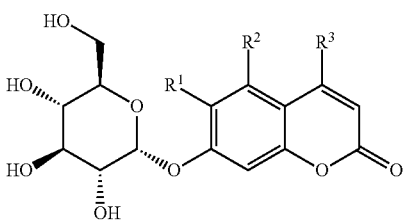

wherein:
one of R¹ and R² is F and the other is H, and
R³ is an alkyl group having from 1 to 12 carbon atoms; and
a composition, wherein the composition comprises the enzyme substrate, wherein if the composition is brought into contact with the bacterial spores to form a mixture, the mixture will have an initial pH in the range from 6.0 to 9.0;
b) subjecting at least the bacterial spores to the sterilization process;
c) contacting the composition with the bacterial spores; and
d) evaluating efficacy of the sterilization process.

Advantageously, fluorinated 4'-alkylumbelliferyl α-D-glucopyranosides according to the present disclosure are stable under typical thermal conditions used in sterilization processes, react with *G. stearothermophilus* to generate fluorescent species with improved fluorescence yield as compared to non-fluorinated analogs, at conditions in a pH range of 6.0 to 9.0.

All scientific and technical terms used herein have meanings commonly used in the art unless otherwise specified. The definitions provided herein are to facilitate understanding of certain terms used frequently in this application and are not meant to exclude a reasonable interpretation of those terms in the context of the present disclosure.

The term "powerset" as used herein for a given set S having n elements refers to the mathematical definition of a powerset and all possible subsets of S, without including the empty set, but including S itself, having from 1 to n elements in every combination and is denoted as P(S). Applicants note that the mathematical definition of a powerset includes the empty set (a set having no elements). However, the definition adopted here by Applicants excludes the empty set and includes all subsets having at least one element, including the full set of n elements (S). In general, the powerset includes all subsets having "i" elements for I=1 to n−1, and the subset having all n elements (n). For instance, the powerset of a subset S having the elements a, b, and c (n=3) includes the following 7 subsets: all possible subsets having one element: {(a), (b), (c)}; all possible subsets having any possible combination two elements: {(a, b), (a, c), (b, c)}, and the subset having all 3 elements: (a, b, c).

The term "frangible" container refers to any container that can be acted upon to release its contents, for example by breaking it, puncturing it, shattering it, and/or cutting it.

The term "process challenge device", abbreviated as "PCD," refers to a container (e.g., a housing) that may comprise a biological sterilization indicator inside and which contains an additional barrier to a sterilant to reach its contents (e.g., a biological sterilization indicator) compared to the path the sterilant would need to travel to reach the items insider the PCD (e.g., biological sterilization indicator) if the items were not inside the PCD. A PCD is also known as a "test pack" and both terms are being used interchangeably in this disclosure. A PCD is designed to simulate sterilization conditions used for instruments or other items to be sterilized and generally comprise a defined challenge to the sterilization process. In its most simply embodiment, a PCD is a sealed container that has an inlet (e.g., an orifice or puncture) for a sterilant to be able to reach the interior of the container.

The term "fluorescently-detectable compound" refers to a compound that is susceptible to detection by fluorescence, even if the compound may not be fluorescent at all times and only fluoresces when excited by energy of the proper wavelength. Examples of fluorescently-detectable compounds useful in this patent application include the products of an enzymatic reaction of a substrate with a cleaving enzyme where the substrate is not fluorescently-detectable using the excitation wavelengths used to detect the enzymatic reaction product. The fluorescent detection can be carried out in solution or on a substrate. An example of such a compound is 4-methylumbelliferone (4-MU), which is the product of the enzymatic cleavage of 4'-alkylumbelliferyl α-D-glucopyranoside by the enzyme α-D-glucosidase.

Features and advantages of the present disclosure will be further understood upon consideration of the detailed description as well as the appended claims.

Figure 1:
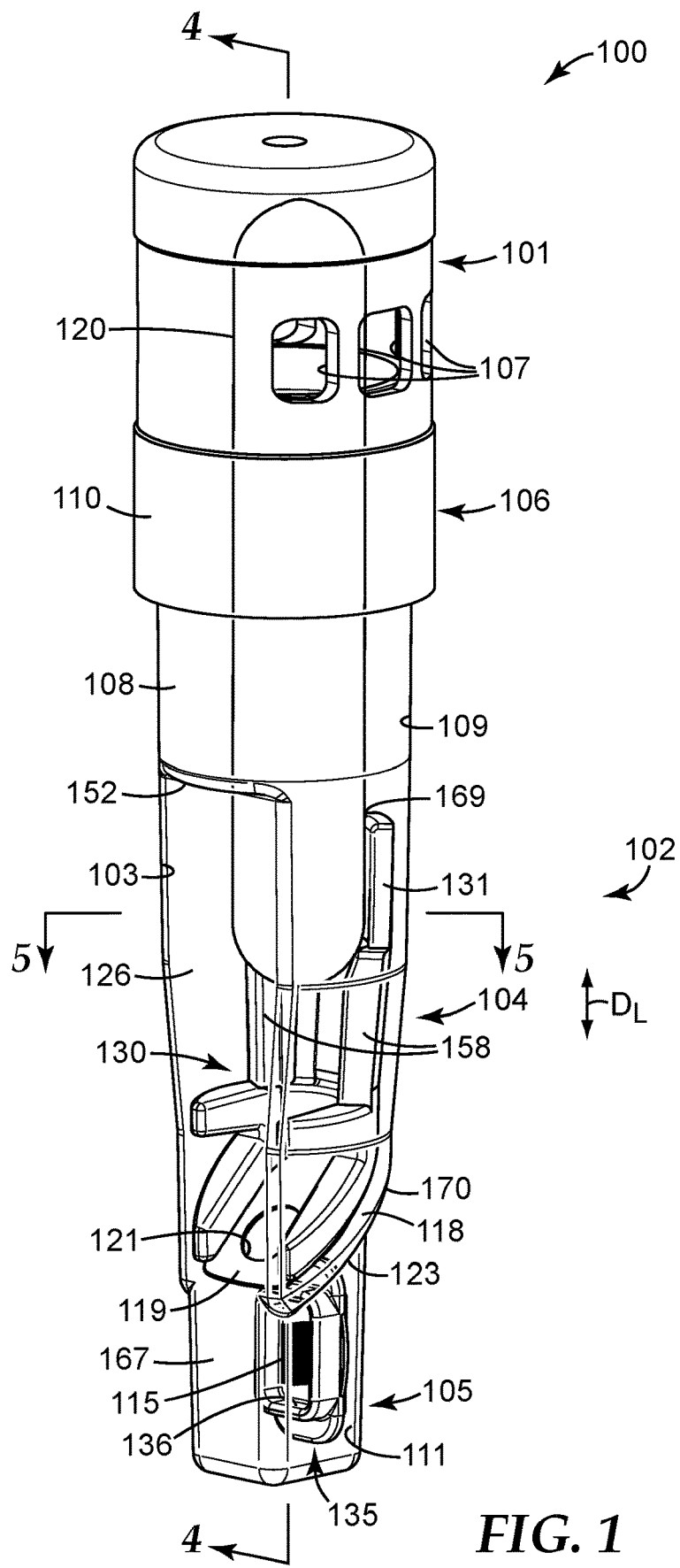
FIG. 1 is a front perspective view of a biological sterilization indicator according to one embodiment of the present disclosure, the biological sterilization indicator including a housing that includes a first portion and a second portion.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

The present disclosure provides two monofluorinated 4'-alkylumbelliferyl α-D-glucopyranosides, which can be used as enzyme substrates, that are stable under typical thermal conditions used in sterilization processes and react with *G. stearothermophilus* to generate fluorescent species with improved fluorescence yield, as compared to nonfluorinated analogs, at conditions in a pH range of 6.0 to 9.0.

The monofluorinated 4'-alkylumbelliferyl α-D-glucopyranoside is represented by the structural formula

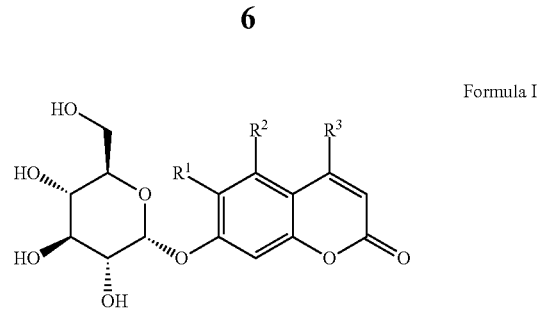

Formula I

In Formula I, one of $R^1$ and $R^2$ is F (i.e., fluorine) and the other is H (i.e., hydrogen). $R^3$ is an alkyl group having from 1 to 12 carbon atoms such as, for example, methyl, ethyl, propyl (e.g., n-propyl or isopropyl), butyl (e.g., n-butyl, isobutyl), pentyl (e.g., n-pentyl, isopentyl, neopentyl), hexyl, octyl, nonyl, decyl, undecyl, and dodecyl. In some embodiments, $R^3$ is an alkyl group having 1 to 4 carbon atoms such as, for example, methyl, ethyl, n-propyl, isopropyl, n-butyl, and isobutyl.

In one embodiment, the fluorinated 4'-alkylumbelliferyl α-D-glucopyranoside is represented by structural Formula II, below:

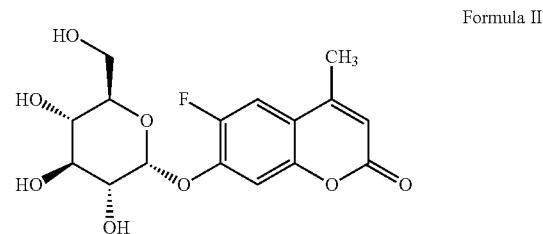 [SMILES: Cc1cc(=O)oc2cc(O[C@H]3O[C@H](CO)[C@@H](O)[C@H](O)[C@H]3O)c(F)cc12]

Formula II

In another embodiment, the fluorinated 4'-alkylumbelliferyl α-D-glucopyranoside is represented by structural Formula III, below:

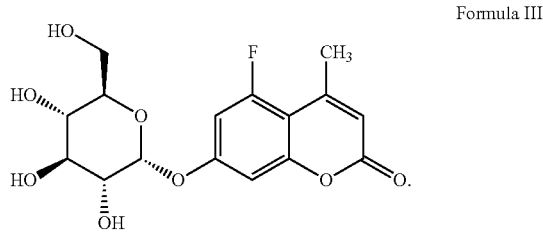 [SMILES: Cc1cc(=O)oc2cc(O[C@H]3O[C@H](CO)[C@@H](O)[C@H](O)[C@H]3O)cc(F)c12]

Formula III

The compounds in Formulas II and III can be prepared by methods described hereinafter.

In some embodiments, combinations of compounds according to Formula II and Formula III may be used.

In some embodiments, the present disclosure is directed to a self-contained biological sterilization indicator comprising:

a housing, bacterial spores comprising, and/or capable of producing, an enzyme capable of catalyzing the cleavage of an enzyme substrate represented by the structural formula

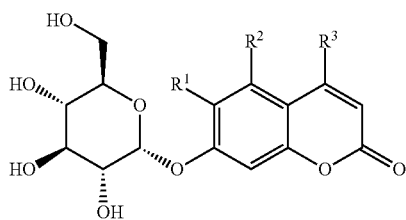

wherein:
one of $R^1$ and $R^2$ is F and the other is H, and
$R^3$ is an alkyl group having from 1 to 12 carbon atoms;
and
a frangible container containing a composition, wherein the composition comprises the enzyme substrate. The self-contained biological sterilization indicator is configured such that if the frangible container is broken, the composition will contact the bacterial spores to form a mixture having a pH in the range from 6.0 to 9.0, in some preferred embodiments from 6.0 to 7.0. In one exemplary embodiment, the frangible container is a sealed tube or ampule containing the composition. Upon breaking the frangible container, the composition and the bacterial spores are brought into contact, for example, by diffusion or agitation, or other mixing means. Optionally, in some embodiments, the self-contained biological sterilization indicator is inside a process-challenge device.

Housing

In general, the term "housing" refers to a container, usually an outer container, having walls impermeable to a sterilant, where other components of the biological sterilization indicator are located. The housing may be inside a process challenge device or may be a process challenge device itself. In some embodiments, the housing may have dimensions useful to produce a flat or generally planar biological sterilization indicator. This disclosure encompasses housings of any shape and dimensions.

The housing contains at least one opening that allows flow of a sterilant to the interior of the housing (sterilant pathway). In some embodiments, the housing may comprise a body with an opening and a cap to close that opening. In some embodiments, the cap may be capable of completely sealing the housing and eliminating any fluid communication between the interior of the housing and ambiance (e.g., closing the sterilant pathway). In general, the cap has an open position in which there is an opening (e.g., a gap) between the cap and the body of the container that allows flow of liquid or gas (e.g., a sterilant) into and out of the interior of the housing. The cap also has a closed position where the opening is sealed and any fluid flow through the gap is eliminated. In other embodiments, the cap may comprise vents that allow passage of a sterilant to the interior of the housing and create an additional sterilant pathway, even if the cap is present and in the closed position. In other preferred embodiments, however, when the cap comprises vents, placing the cap in the closed position simultaneously closes (a) the gap between the cap and the body of the container and (b) the vents present on the cap, essentially closing the sterilant pathway.

In other embodiments, the cap may lack vents and the only sterilant pathway may be through the space between the cap and the body of the housing (or through another opening or vent, if present on the body) when the cap is the open position. In some embodiments, if vents exist on the housing, they are located on the cap. In embodiments where no other opening exists besides the opening between the cap and the body of the housing, then placing the cap in the closed position completely seals off the interior of the housing, which stops the fluid communication between the interior of the housing and ambience. In those embodiments, the sterilant pathway may be sealed when the cap is in the closed position.

Microorganisms (Spores)

Generally, microorganisms are chosen to be used in a biological sterilization indicator that are particularly resistant to a given sterilization process. The biological sterilization indicators of the present disclosure include a viable culture of a known species of microorganism, usually in the form of microbial spores. Bacterial spores, rather than the vegetative form of the organisms, are used at least partly because vegetative bacteria are known to be relatively easily killed by sterilizing processes. Additionally, spores also have superior storage characteristics and could remain in their dormant state for years. As a result, sterilization of an inoculum of a standardized spore strain provides a higher degree of confidence that inactivation of all microorganisms in a sterilizing chamber has occurred.

By way of example only, the present disclosure describes the microorganisms used in the biological sterilization indicator as being "spores;" however, it should be understood that the type of microorganism (e.g., spore) used in a particular embodiment of the biological sterilization indicator is selected for being resistant to the particular sterilization process contemplated (more resistant than the microorganisms normally present on the items to be sterilized so that inactivation of the test microorganisms indicates a successful sterilization.).

In general, the spores used in a particular system are selected according to the sterilization process at hand. For example, for a steam sterilization process, *Geobacillus stearothermophilus* (*G. stearothermophilus*) can be used. While demonstrated for *G. stearothermophilus*, the compounds and devices of the present disclosure may also be used with other biological sterilization indicators, for example, if as they produce appropriate enzymes to cleave the α-D-glucopyranoside moiety from the fluorinated 4-alkylumbelliferyl moiety.

The bacterial spores either comprise an enzyme capable of catalyzing the cleavage of a monofluorinated 4'-alkylumbelliferyl α-D-glucopyranoside according to Formula I to produce a fluorescently-detectable compound, or are capable of producing such an enzyme, or both. The enzymes useful in biological sterilization indicators of the present disclosure include extracellular and intracellular enzymes whose activity correlates with the viability of at least one of the microorganisms commonly used to monitor sterilization efficacy ("test" microorganism or "test spores"). In this context, "correlates" means that the enzyme activity, over background, can be used to predict growth of the test microorganism. The enzyme should be one which, following a sterilization cycle which is sublethal to the test microorganism, remains sufficiently active to react with a substrate for the enzyme, within twenty-four hours, and in preferred embodiment within eight hours or less, yet be inactivated or appreciably reduced in activity following a sterilization cycle which would be lethal to the test microorganism.

When acted upon by an enzyme (e.g., α-glucosidase) produced by *G. stearothermophilus*, monofluorinated 4'-alkylumbelliferyl α-D-glucopyranosides according to Formula I are cleaved to form the fluorescent compounds shown below in Formula IV:

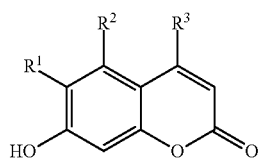

Formula IV and their deprotonated forms shown in Formula V, below:

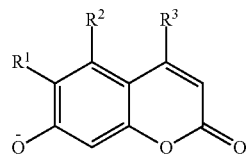

Formula V while the nonfluorinated analog 4-methylumbelliferone has a ($pK_a$=7.8), shown below, the compounds of Formulas II and III, after cleavage of the glucose, have $pK_a$ values of about 6.5 and 5.9, respectively, making them better-suited for use in less alkaline, more biological-organism-friendly pH values of, for example, from 6.0 to 7.0. In some preferred embodiments, the enzyme that cleaves the monofluorinated 4'-alkylumbelliferyl α-D-glucopyranoside is α-D-glucosidase. This is especially advantageous since the deprotonated form fluoresces much more strongly.

Sterilization Processes

Biological sterilization indicators of the present disclosure may be used to monitor the effectiveness of one or more types of sterilization procedures, including sterilization procedures that use various sterilants, such as steam (e.g., pressurized steam), vapor phase hydrogen peroxide (which may or may not include hydrogen peroxide plasma), ethylene oxide gas, dry heat, propylene oxide gas, methyl bromide, chlorine dioxide, formaldehyde and peracetic acid (alone or with a vapor phase of another material), ozone, radiation, and combinations thereof.

In at least some of the sterilization processes, an elevated temperature, for example, 50° C., 60° C., 100° C., 121° C., 132° C., 134° C., or 135° C., is included or may be encountered in the process. In addition, elevated pressures and/or a vacuum may be encountered, for example, 15 psi (0.10 MPa) at different stages within a single given sterilization cycle, or in different sterilization cycles.

In the case of steam being the sterilant, the sterilization temperatures can include 121° C., 132° C., 134° C., or 135° C. The instant biological sterilization indicators are suitable for steam sterilization cycles at each of the temperatures above and for each temperature the cycle can have a different air removal process chosen from gravity, pre-vacuum ("pre-vac"), and steam flush pressure pulse (SFPP). Each of these cycles may have different exposure times depending on the type of instruments/devices being sterilized. In this disclosure, pre-vacuum and SFPP are also labeled as Dynamic Air Removal (DAR) cycles.

A tabular representation of exemplary steam sterilization cycles in which the present biological sterilization indicators can be used is shown below:

| 121° C. | | | 132° C. | | | 134° C. | | | 135° C. | | |
|---|---|---|---|---|---|---|---|---|---|---|---|
| Gravity | Pre-Vac | SFPP | Gravity | Pre-Vac | SFPP | Gravity | Pre-Vac | SFPP | Gravity | Pre-Vac | SFPP |

In this disclosure, the term a "T gravity" sterilization cycle refers to a steam process where the sterilization temperature is T and air is removed (conditioning) from the sterilization chamber as a result of steam displacement. In this case, the force of gravity causes the heavier gas (air) to exit the chamber via the sterilizer drain as steam enters the chamber. In general, gravity cycles require more exposure time because the air removal method is more passive in nature. For instance, a "121 gravity" cycle is a steam sterilization carried out at 121° C. under gravity conditioning.

A "T pre-vac" sterilization cycle refers to a steam process where the sterilization temperature is T and where air removal is done by mechanical vacuum evacuation in conjunction with steam injections. As a consequence of this conditioning method, the pressure in the sterilization chamber can decrease below atmospheric values during the evacuation cycle and can increase to positive pressures when steam is being introduced. For instance, "121 pre-vac" sterilization cycle refers to a steam process where the sterilization temperature is 121° C. and the conditioning occurs via vacuum evacuations.

A "T SFPP" sterilization cycle refers to a steam process where the sterilization temperature is T ° C. and where conditioning is carried out through a series of pressurizations and flushes with steam. During a SFPP process, the pressure in the chamber does not drop below atmospheric (no vacuum is drawn). For example, a "121 SFPP cycle refers to a steam process where the sterilization temperature is 121° C. and the conditioning occurs via steam flush pressure pulses.

In this disclosure, a "dynamic air removal" cycle refers to a sterilization cycle that uses either pre-vacuum or SFPP conditioning.

In other embodiments, the biological sterilization indicators of the present disclosure may be used to monitor the effectiveness of a vapor phase sterilization procedure that uses an oxidizing sterilant. In some embodiments, the biological sterilization indicators may be used to monitor the effectiveness of any of the hydrogen peroxide sterilization procedures known in the art. More preferably, the biological sterilization indicator may be used to monitor the effectiveness of a hydrogen peroxide vapor phase sterilization procedure.

While aqueous hydrogen peroxide ($H_2O_2$) has a long history of use as a sterilant, the concept of vapor-phase hydrogen peroxide (VPHP) sterilization has been developed within the past decade. This process is a low temperature sterilization process that kills a wide range of microorganisms including bacterial endospore-forming bacteria commonly used as challenge organisms to evaluate and validate the effectiveness of sterilization cycles in hospitals. A major advantage of hydrogen peroxide is its short exposure cycle time (few minutes). Furthermore, at the end of a hydrogen peroxide sterilization process, only air and water remain in the chamber. Significantly, the novel features of the biological sterilization indicators described herein allow for the development of a rapid-readout hydrogen peroxide biological sterilization indicator.

In general, a sterilization process includes placing the biological sterilization indicator of the present disclosure in a sterilizer. In some embodiments, the sterilizer includes a sterilization chamber that can be sized to accommodate a plurality of articles to be sterilized, and can be equipped with a means of evacuating air and/or other gases from the chamber and a means for adding a sterilant to the chamber. The self-contained biological sterilization indicator can be positioned in areas of the sterilizer that are most difficult to sterilize. Alternately, the biological sterilization indicator can be positioned in process challenge devices to simulate sterilization conditions where sterilant may not be delivered as directly as would be the case in more favorable sterilization circumstances.

The sterilant can be added to the sterilization chamber after evacuating the chamber of at least a portion of any air or other gas present in the chamber. Alternatively, sterilant can be added to the chamber without evacuating the chamber. A series of evacuation steps can be used to assure that the sterilant reaches all desired areas within the chamber and contacts all desired article(s) to be sterilized, including the biological sterilization indicator.

The self-contained biological sterilization indicators are capable of determining the efficacy of one or more steam sterilization cycles chosen from the powerset of the following eleven cycles: 121 gravity, 121 pre-vac, 121 SFPP, 132 gravity, 132 pre-vac, 132 SFPP, 134 pre-vac, 134 SFPP, 135 gravity, 135 pre-vac, and 135 SFPP, preferably within 1 hr.

Composition

The composition is located in the frangible container and contains one or more enzyme substrates according to Formula I (e. g., a compound according to Formula II or Formula III), mentioned above. In some embodiments, the composition may also include nutrients for the spores, such as germination nutrients that allow germination and/or growth of any viable surviving spores. In some embodiments, the composition is solid (e.g., a powder).

Suitable nutrients may be provided initially in a dry form (e.g., powdered form, tablet form, caplet form, capsule form, a film or coating, entrapped in a bead or other carrier, another suitable shape or configuration, or a combination thereof) and then optionally combined with a suitable solvent to provide a composition that is then placed in the frangible container.

In some embodiments, the composition is liquid (i.e., a liquid composition). In some of those embodiments, the solvent of the liquid composition is water. The combination of nutrients form a nutrient medium and together with the enzyme substrate and one or more non-nutrient components such as indicators, buffer components, salts, solvent, etc. (see below) form the composition.

The nutrients in the composition can include one or more sugars, including, but not limited to, glucose, fructose, dextrose, maltose, trehalose, cellobiose, or the like, or a combination thereof. Alternatively, the nutrients may include complex media, such as peptone, tryptone, phytoene peptone, yeast extract, soybean casein digest, other extracts, hydrolysates, etc., or a combination thereof. In other embodiments, the nutrients in the composition represent a combination of one or more complex media components and other specific nutrients. The nutrient medium can also include a salt, including, but not limited to, sodium chloride, potassium chloride, calcium chloride, or the like, or a combination thereof. In some embodiments, the nutrient can further include at least one amino acid, including, but not limited to, at least one of methionine, phenylalanine, alanine, tyrosine, and tryptophan.

As part of a self-contained biological sterilization indicator, the composition comprising nutrients, the enzyme substrate, and other components is typically present throughout the sterilization procedure but is kept separate and not accessible to the sources of biological activity in the frangible container until desired. After the sterilization process is completed and the biological sterilization indicator is used to determine the efficacy of the sterilization, the composition is placed in contact with the spores resulting in a mixture. In this disclosure, placing the composition with the spores includes activating the frangible container so that the composition is released and contacts the spores. This process may include mixing of the composition with the spores, such as manual or mechanical shaking of the housing of the biological sterilization indicator so that the composition adequately mixes with the spores.

In this disclosure, the process of bringing the spores and medium together is referred to as "activation" of the biological sterilization indicator. That is, the term "activation" and variations thereof, when used with respect to a biological sterilization indicator refer generally to bringing one or more sources of biological activity (e.g., spores) in fluid communication with the composition (comprising, e.g., a nutrient medium for the spores of interest and an enzyme substrate). For example, when a frangible container within the biological sterilization indicator that contains the composition is at least partially fractured, punctured, pierced, crushed, cracked, breaking, or the like, such that the medium has been put in fluid communication with the source(s) of biological activity, the biological sterilization indicator can be described as having been "activated." Said another way, a biological sterilization indicator has been activated when the source(s) of biological activity have been exposed to the composition that was previously housed separately from the source(s) of biological activity.

In some preferred embodiments, the mixture resulting from mixing the composition with the spores after activation remains isolated within the housing of the biological sterilization indicator after the sterilization cycle has been completed and no additional reagents or components are added to it during or after activation. If the spores are viable and grow, then the enzyme produced by the bacteria catalyzes the cleavage of the enzyme substrate, which produces the fluorescently-detectable compound. This means that the same solution in the same container (housing) is used for three separate events: (a) spore germination/growth, if the spores are viable, (b) the enzymatic cleavage of the enzyme substrate, resulting in the production of the fluorescently-detectable compound, and (c) the fluorescence detection of the fluorescently-detectable compound.

In some embodiments, the composition may comprise a buffered solution. The ionic conditions of the buffered solution should be such that the enzyme and enzyme substrate are not affected. In some embodiments, a buffer solution is used as part of the composition, such as phosphate buffers, (e.g., phosphate buffered saline solution, potassium phosphate or potassium phosphate dibasic), tris (hydroxymethyl)aminomethane-HCl solution, or acetate buffer, or any other buffer suitable for sterilization known in the art. Buffers suitable for the present biological sterilization indicators should be compatible with fluorogenic and chromogenic enzyme substrates used as part of the composition. Another consideration in choosing the buffers is their influence on the enzyme activity. For example, phosphate buffered saline contains a relatively high concentration of inorganic phosphate, which is a competitive inhibitor of alkaline phosphatase. Thus, for that enzyme, a Tris-HCl buffer is recommended. The strength of the buffered solution may be from 0.05 M to 0.5 M, preferably from 0.05 M to 0.25 M, more preferably from 0.05 M to 0.15 M, even more preferably about 0.1 M.

The concentration of enzyme substrate present in the composition depends upon the identity of the particular substrate and enzyme, the amount of enzyme-product that must be generated to be detectable, either visually or by instrument, and the amount of time that one is willing to wait in order to determine whether active enzyme is present in the reaction mixture. Preferably, the amount of enzyme substrate is sufficient to react with any residual active enzyme present, after the sterilization cycle, within about an eight-hour period of time, such that at least $10^{-8}$ molar enzyme-modified product is produced.

In some embodiments, the composition comprises a solution adjusted to a suitable pH, but without an added buffer system. In other embodiments, however, the composition does comprise a buffered solution.

In some embodiments, the biological sterilization indicator may comprise an additional indicator compound that can facilitate the detection of another metabolic activity of the test microorganisms (e.g., spore) (aside from an enzyme substrate that can produce a fluorescently-detectable compound). This additional metabolic activity can also be an enzymatic activity. Non-limiting examples of indicator compounds include a chromogenic enzyme substrate (e.g., observable in the visible spectrum), a pH indicator, a redox indicator, a chemiluminescent enzyme substrate, a dye, and a combination of any two or more of the foregoing indicator compounds.

In some embodiments, the additional indicator is a pH indicator that produces a change in color when the pH decreases, indicating growth of the test microorganisms. In some embodiments, the pH indicator is bromocresol purple. The pH indicator can be used to detect a second biological activity, such as the fermentation of a carbohydrate to acid end products (suggesting survival of the test microorganisms) and an enzymatic biological activity such as α-D-glucosidase enzyme activity, for example. These activities can indicate the presence or absence of a viable spore following the exposure of a biological sterilization indicator to a sterilization process, for example. The bromocresol purple can be used at a concentration of about 0.03 g/L in the aqueous mixture, for example. Enzyme substrates according to any of Formulas I-III can be used, for example, at a concentration of about 0.05 to about 0.5 g/L (e.g., about 0.05 g/L, about 0.06 g/L, about 0.07 g/L, about 0.08 g/L, about 0.09 g/L, about 0.1 g/L, about 0.15 g/L, about 0.2 g/L, about 0.25 g/L, about 0.3 g/L, about 0.35 g/L, about 0.4 g/L, about 0.45 g/L, about 0.5 g/L) in the aqueous mixture.

In some situations, one or more components of a biological sterilization indicator (e.g., crevasses in the housing, substrates or carriers for spores, walls of container, etc.) may retain residual oxidizing sterilant. This can occur, for example, with hydrogen peroxide vapor as well as with other vapor sterilants such as ozone and peracetic acid. For example, certain carrier materials, e.g., those that are hydrophilic such as glass fiber and cellulosic materials, can retain residual oxidizing sterilant, particularly hydrogen peroxide. In this context, "residual" means an amount of retained sterilant that inhibits the growth of low numbers of spore survivors. Typically, this means more than 10 micrograms of sterilant retained per microgram of carrier. In certain situations, the amount of residual sterilant can be greater than 40 micrograms sterilant per milliliter of growth media. As a comparison, if the carrier material has a contact angle of greater than 90°, it is hydrophobic, and there is generally no more than 10 micrograms sterilant retained per microgram of carrier.

Therefore, in some embodiments, the biological sterilization indicators comprise one or more neutralizers, which are not an enzyme and not a metal catalyst disposed within the biological sterilization indicator. A neutralizer is a compound or material that reacts with residual sterilant, e.g., hydrogen peroxide, to neutralize its effect, wherein the neutralizer is not an enzyme, and not a metal catalyst. Enzyme neutralizers are typically not stable at the high temperatures, and thus not desirable.

Suitable examples of neutralizers include sulfur containing materials such as methionine, L-cysteine, D-ethionine, S-methyl-L-cysteine, S-benzyl-L-cysteine, sodium thiosulfate, glutathione, L-cystathionine, N-acetyl-L-cysteine, carboxymethylcysteine, D,L-homocysteine, D,L-homocysteine-thiolactone, and thiodipropionic acid, and non-sulfur containing materials such as isoascorbic acid, potassium ferricyanide, and sodium pyruvate. Various combinations of such neutralizers can be used. Preferred neutralizers include methionine, L-cysteine, D-ethionine, S-methyl-L-cysteine, S-benzyl-L-cysteine, sodium thiosulfate, thiodipropionic acid, isoascorbic acid, potassium ferricyanide, sodium pyruvate, and combinations thereof.

Detection of Enzymatic Activity and Determination of a Successful Sterilization Process As mentioned in the previous section, after the indicator is exposed to the sterilization process, the spores can be incubated in a nutrient medium to determine whether any of the spores survived the sterilization process, with spore growth indicating that the sterilization process was insufficient to destroy all of the test microorganisms.

In some embodiments, the cap of the biological sterilization indicator can be coupled to the body of the biological sterilization indicator during sterilization in a first position that maintains fluid communication between the interior of the biological sterilization indicator and ambient environment, allowing the sterilant to reach the interior of the biological sterilization indicator. After sterilization, in order to activate the biological sterilization indicator, the cap can be pressed further onto the tube (e.g., to a second position in which the interior of the biological sterilization indicator is no longer in fluid communication with ambience) to maintain sterility and reduce the evaporation rate of the composition. As mentioned previously, the composition is maintained separate from the spores in the frangible container during sterilization, but is released into the interior of the housing after sterilization as part of the activation by fracturing, puncturing, piercing, crushing, cracking, breaking, or the like, the frangible container.

In some embodiments of the present disclosure, closing the biological sterilization indicator (e.g., moving a portion of the biological sterilization indicator, such as the cap, relative to another portion to seal the interior) can include or cause fracturing, puncturing, etc. of the frangible container containing the composition, such that closing the biological sterilization indicator causes activation of the biological sterilization indicator.

After activation, the mixture resulting from placing the composition in contact with the spores is incubated for a period of time and under conditions that would be sufficient to liberate a detectable amount of the enzyme modified product, assuming, of course, that any of the spores remain active. In general, the amount of product which is detectable by known methods is at least $10^{-8}$ molar. Preferably, the incubation conditions are sufficient to generate at least $10^{-8}$ molar of fluorescently-detectable compound, more preferably, at least about $10^{-6}$ molar or even at least about $10^{-5}$ molar of fluorescently-detectable compound. The incubation time and temperature needed to produce a detectable amount of fluorescently-detectable compound will depend upon the identity of the enzyme and the substrate, and the concentrations of each present in the reaction mixture. In general, the incubation time required is between about 1 minute and 12 hours, and the incubation is between about 20° C. and 70° C. Preferably, where *G. stearothermophilus* is the source of the enzyme, the incubation time is from about 2 minutes to 3 hours, or from 2 minutes to 1 hour, or from 5 minutes to 1 hour, or from 15 minutes to 30 minutes, or from 15 minutes to 25 minutes, and the incubation temperature is from about 30° C. to 40° C., and from about 52° C. to 65° C., respectively.

To detect a detectable change in the spores the biological sterilization indicator can be assayed immediately after the composition and the spores have been combined to achieve a baseline reading. After that, any detectable change from the baseline reading can be detected. The biological sterilization indicator can be monitored and measured continuously or intermittently. In some embodiments, a portion of, or the entire, incubating step may be carried out prior to measuring the detectable change. In some embodiments, incubation can be carried out at one temperature (e.g., at 37° C., or at 50-60° C.), and measuring of the detectable change can be carried out at a different temperature (e.g., at room temperature, 25° C., or at 37° C.). In other embodiments, the incubation and measurement of fluorescence occurs at the same temperature.

The readout time of the biological sterilization indicator (i.e., the time to determine the effectiveness of the sterilization process) can be, in some embodiments, less than 8 hours, in some embodiments, less than 1 hour, in some embodiments, less than 30 minutes, in some embodiments, less than 15 minutes, in some embodiments, less than 5 minutes, and in some embodiments, less than 1 minute. In other embodiments, the readout time for the biological sterilization indicator of this disclosure is from 2 min to 1 hr, or from 2 min to 50 min, or from 2-30 min, or from 2-20 min, or from 2-25 min, or from 5 to 30 min, or from 5-25 min, or from 5-20 min. The detection of fluorescence above the baseline reading that would indicate presence of viable spores (i.e., a failed sterilization process) can be performed according to any method know in the art, including area under curve (in a plot of time vs fluorescence intensity), monitoring a change in slope of the curve, using a threshold value for the fluorescence, etc., or a combination thereof of two or more techniques.

One of the advantages of the biological sterilization indicators of this disclosure is that a single type can be used for various sterilization conditions. Examples include the steam sterilization cycles: 121 gravity, 121 pre-vac, 121 SFPP, 132 gravity, 132 pre-vac, 132 SFPP, 134 pre-vac, 134 SFPP, 135 gravity, 135 pre-vac, and 135 SFPP. For that reason, the biological sterilization indicator can be used for any subset of cycles chosen from the set above. That is, a single biological sterilization indicator is capable of determining the efficacy of one or more sterilization cycles chosen from the powerset of 121 gravity, 121 pre-vac, 121 SFPP, 132 gravity, 132 pre-vac, 132 SFPP, 134 pre-vac, 134 SFPP, 135 gravity, 135 pre-vac, and 135 SFPP.

In addition to being able to determine the efficacy of any of the above sterilization cycles, the biological sterilization indicator is capable of doing so in less than one hour. In fact, in some embodiments, the biological sterilization indicator has a readout time of less than 1 hour, in some embodiments, less than 30 minutes, in some embodiments, less than 15 minutes, or even less than 10 or less than 5 minutes, in other embodiments, the readout time is from 2 min to 1 hr, or from 10 min to 50 min, or from 10-30 min, or from 10-20 min, or from 10-25 min, or from 15 to 30 min, or from 15-25 min, or from 15-20 min.

Exemplary Embodiments of Self-Contained Biological Sterilization Indicators

FIGS. 1-7 illustrate the biological sterilization indicator 100 according to one embodiment of the present disclosure. Other embodiments of biological sterilization indicators are described in U.S. Pat. No. 8,980,622 (Smith et al.); U.S. Pat. No. 9,410,180 (Pederson et al.); U.S. Pat. No. 9,145,573 (Pederson et al.); and U.S. Pat. No. 8,840,837 (Smith et al.), each of which is incorporated herein by reference in its entirety.

The biological sterilization indicator 100 can include a housing 102, which can include a first portion 104 and a second portion 106 (e.g., a cap) adapted to be coupled together to provide a self-contained biological sterilization indicator. In some embodiments, the first portion 104 and second portion 106 can be formed of the same materials, and in some embodiments, the first portion 104 and the second portion 106 can be formed of different materials. The housing 102 can define a reservoir 103 of the biological sterilization indicator 100 in which other components can be positioned and into which a sterilant can be directed during a sterilization process.

The housing 102 can be defined by at least one liquid impermeable wall, such as a wall 108 of the first portion 104 and/or a wall 110 of the second portion 106. It should be understood that a one-part unitary housing 102 may also be employed or that the first and second portions 104 and 106 can take on other shapes, dimensions, or relative structures without departing from the spirit and scope of the present disclosure. Suitable materials for the housing 102 (e.g., the walls 108 and 110) can include, but are not limited to, a glass, a metal (e.g., foil), a polymer (e.g., polycarbonate (PC), polypropylene (PP), polyphenylene (PPE), polyethylene, polystyrene (PS), polyester (e.g., polyethylene terephthalate (PET)), polymethyl methacrylate (PMMA or acrylic), acrylonitrile-butadiene-styrene copolymer (ABS), cycloolefin polymer (COP), cycloolefin copolymer (COC), polysulfone (PSU), polyethersulfone (PES), polyetherimide (PEI), polybutylene terephthalate (PBT), ceramic, porcelain, and combinations thereof.

The biological sterilization indicator 100 includes a frangible container 120 that contains a liquid (e.g., an aqueous mixture) 122, and which is dimensioned to be received within the biological sterilization indicator 100, for example, within at least a portion of the housing 102 (e.g., at least within the first portion 104 of the housing 102). The frangible container 120 can be formed of a variety of materials, including, but not limited to, one or more of metal (e.g., foil), a polymer (e.g., any of the polymers listed above with respect to the housing 102), glass (e.g., a glass ampoule), and combinations thereof. In some embodiments, only a portion of the container 120 is frangible, for example, the container 120 can include a frangible portion or cover (e.g., a frangible barrier, film, membrane, or the like). The frangible container 120 can have a first state in which it is intact and the liquid 122 is contained therein, and a second state in which at least a portion of the container 120 is fractured. In the second state of the container 120, the liquid 122 can be in fluid communication with the reservoir 103 of the biological sterilization indicator 100, e.g., when the container 120 is positioned in the biological sterilization indicator 100.

As shown in the illustrated embodiment, the container 120 can be held in place within the biological sterilization indicator 100 and/or fractured by an insert 130, which is described in greater detail below.

Figure 2:
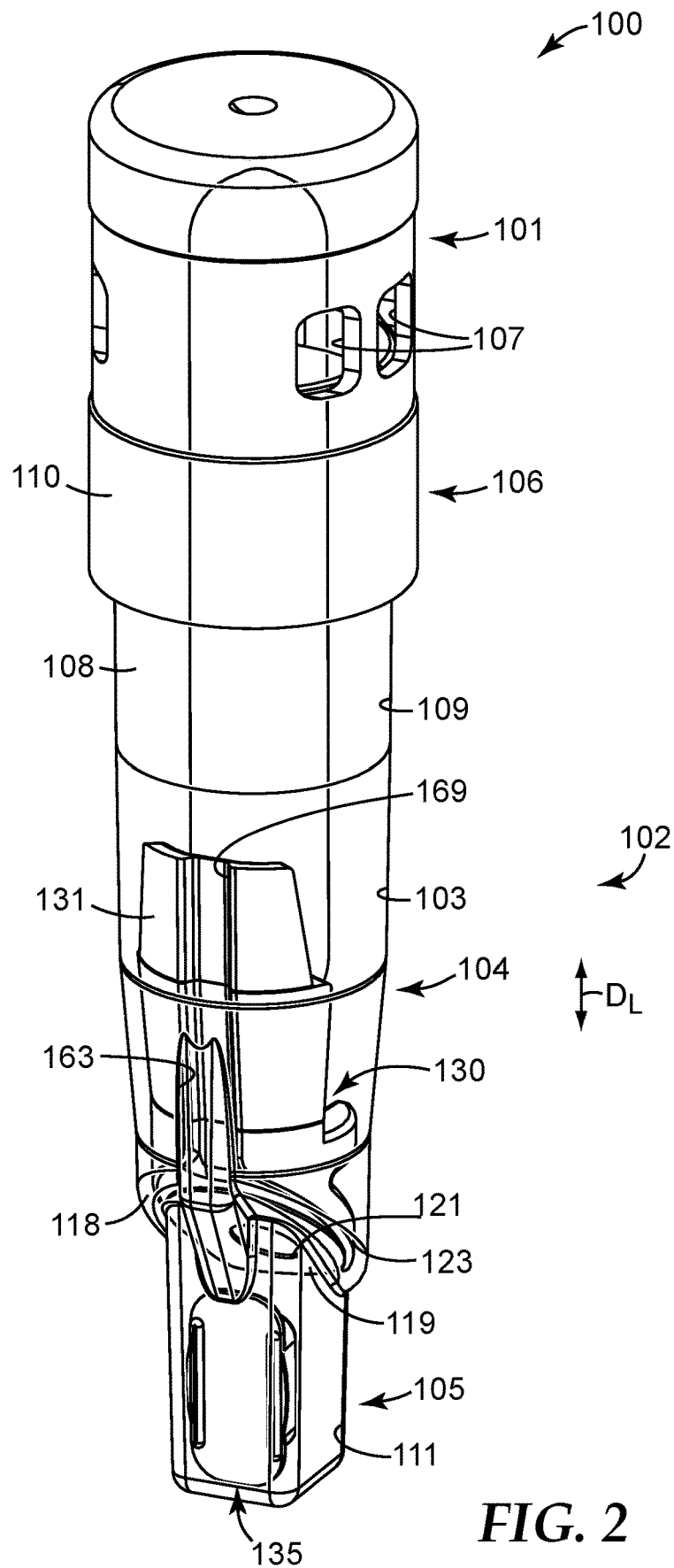
FIG. 2 is a rear perspective view of the biological sterilization indicator of FIG. 1.
Figure 3:
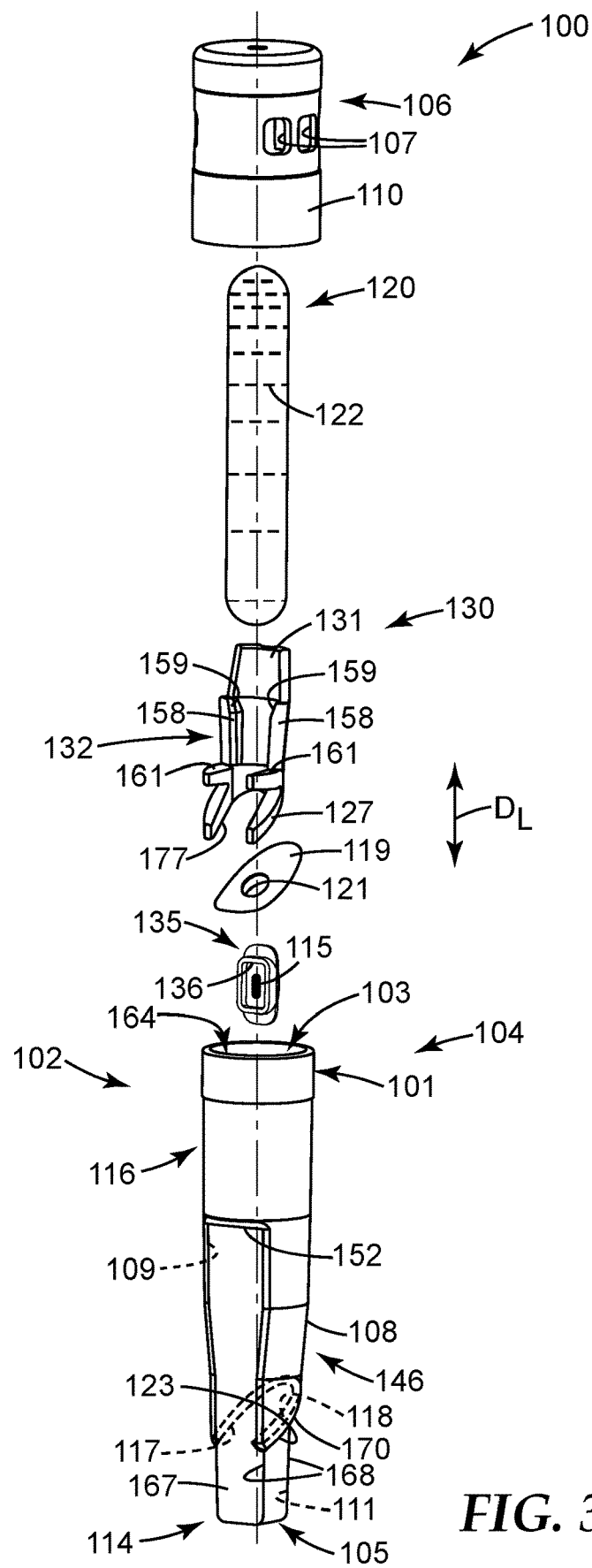
FIG. 3 is a front exploded view of the biological sterilization indicator of FIGS. 1-2.

The first portion 104 of the housing 102 can be adapted to house a majority of the components of the biological sterilization indicator 100, and can be referred to as a "tube," "tubular body," "base," or the like. The housing 102 can include a reservoir 103 that can be defined by one or both of the first portion 104 and the second portion 106 of the housing 102. The biological sterilization indicator 100 can further include spores or another source(s) of biological activity 115 (or a locus of spores) positioned in fluid communication with the reservoir 103. As shown in FIGS. 1-3, the second portion 106 of the housing 102 can include one or more apertures 107 to provide fluid communication between the interior of the housing 102 (e.g., the reservoir 103) and ambient environment. For example, the one or more apertures 107 can provide fluid communication between the spores 115 and the ambient environment during a sterilization process, and can serve as an inlet into the biological sterilization indicator 100 and as an inlet of a sterilant path 164 (described in greater detail below). In some embodiments, the second portion 106 of the housing 102 can be coupled to a first (e.g., open) end 101 of the first portion 104 of the housing 102, and the spores 115 can be positioned at a second (e.g., closed) end 105, opposite the first end 101, of the first portion 104 of the housing 102.

In some embodiments, a barrier or filter (e.g., a sterile barrier; not shown) can be positioned in the sterilant path 164 (e.g., at the inlet formed by the aperture 107) to inhibit contaminating or foreign organisms, objects or materials from entering the biological sterilization indicator 100. Such a barrier can include a gas-transmissive, microorganism-impermeable material, and can be coupled to the housing 102 by a variety of coupling means, including, but not limited to, an adhesive, a heat seal, sonic welding, or the like. Alternatively, the barrier can be coupled to the sterilant path 164 via a support structure (such as the second portion 106) that is coupled to the first portion 104 of the housing 102 (e.g., in a snap-fit engagement, a screw-fit engagement, a press-fit engagement, or a combination thereof). During exposure to a sterilant, the sterilant can pass through the barrier into the sterilant path 164 and into contact with the spores 115.

As shown in the illustrated embodiment, the housing 102 can include a lower portion 114 and an upper portion 116, which can be at least partially separated by an inner wall (or partial wall) 118, ledge, partition, flange, or the like, in which can be formed an opening 117 that provides fluid communication between the lower portion 114 and the upper portion 116. In some embodiments, the lower portion 114 of the first portion 104 of the housing 102 (sometimes referred to as simply "the lower portion 114" or the "the lower portion 114 of the housing 102") can be adapted to house the spores 115 or a locus of spores. In some embodiments, the lower portion 114 can be referred to as the "detection portion" or "detection region" of the housing 102, because at least a portion of the lower portion 114 can be interrogated for signs of spore growth. In addition, in some embodiments, the upper portion 116 of the first portion 104 of the housing 102 (sometimes referred to as "the upper portion 116" or the "the upper portion 116 of the housing 102" for simplicity) can be adapted to house at least a portion of the frangible container 120, particularly before activation.

In some embodiments, the portion of the reservoir 103 that is defined at least partially by the upper portion 116 of the housing 102 can be referred to as a first chamber (or reservoir, zone, region, or volume) 109 and the portion of the reservoir 103 that is defined at least partially by the lower portion 114 of the housing 102 can be referred to as a second chamber (or reservoir, zone, region, or volume) 111. In some embodiments, the second chamber 111 can be referred to as a "spore growth chamber" or a "detection chamber," and can include a volume to be interrogated for spore viability to determine the efficacy of a sterilization process.

The first chamber 109 and the second chamber 111 can be positioned in fluid communication with each other to allow a sterilant and the liquid 122 to move from (i.e., through) the first chamber 109 to the second chamber 111. In some embodiments, the degree of fluid connection between the first chamber 109 and the second chamber 111 (e.g., the size of an opening, such as the opening 117, connecting the first chamber 109 and the second chamber 111) can increase after, simultaneously with, and/or in response to the activation step (i.e., the liquid 122 being released from the container 120). In some embodiments, the control of fluid communication (or extent of fluid connection) between the first chamber 109 (e.g., in the upper portion 116) and the second chamber 111 (e.g., in the lower portion 114) can be provided by at least a portion of the insert 130.

The container 120 can be positioned and held in the first chamber 109 during sterilization and when the container 120 is in a first, unfractured, state. The spores 115 can be housed in the second chamber 111 and in fluid communication with ambience when the container 120 is in the first state. The first chamber 109 and the second chamber 111 can be configured such that the container 120 is not present in the second chamber 111, and particularly not when the container 120 is in its first, unfractured, state. A sterilant can move into the second chamber 111 (e.g., via the first chamber 109) during sterilization, and the liquid 122 can move into the second chamber 111 (e.g., from the first chamber 109) during activation, when the container 120 is fractured and the liquid 122 is released into the interior of the housing 102.

As a result, when the container 120 is in the first state, the first chamber 109 and the second chamber 111 can be in fluid communication with one another, and with ambience (e.g., during sterilization). For example, the first chamber 109 and the second chamber 111 can be in fluid communication with ambience via the one or more apertures 107. In some embodiments, the first chamber 109 and the second chamber 111 can be in fluid communication with ambience in such a way that the first chamber 109 is positioned upstream of the second chamber 111 when a sterilant is entering the biological sterilization indicator 100. That is, the first chamber 109 can be positioned between the sterilant inlet (e.g., the one or more apertures 107) and the second chamber 111, and the sterilant inlet can be positioned on an opposite side of the first chamber 109 than the second chamber 111.

Figure 4:
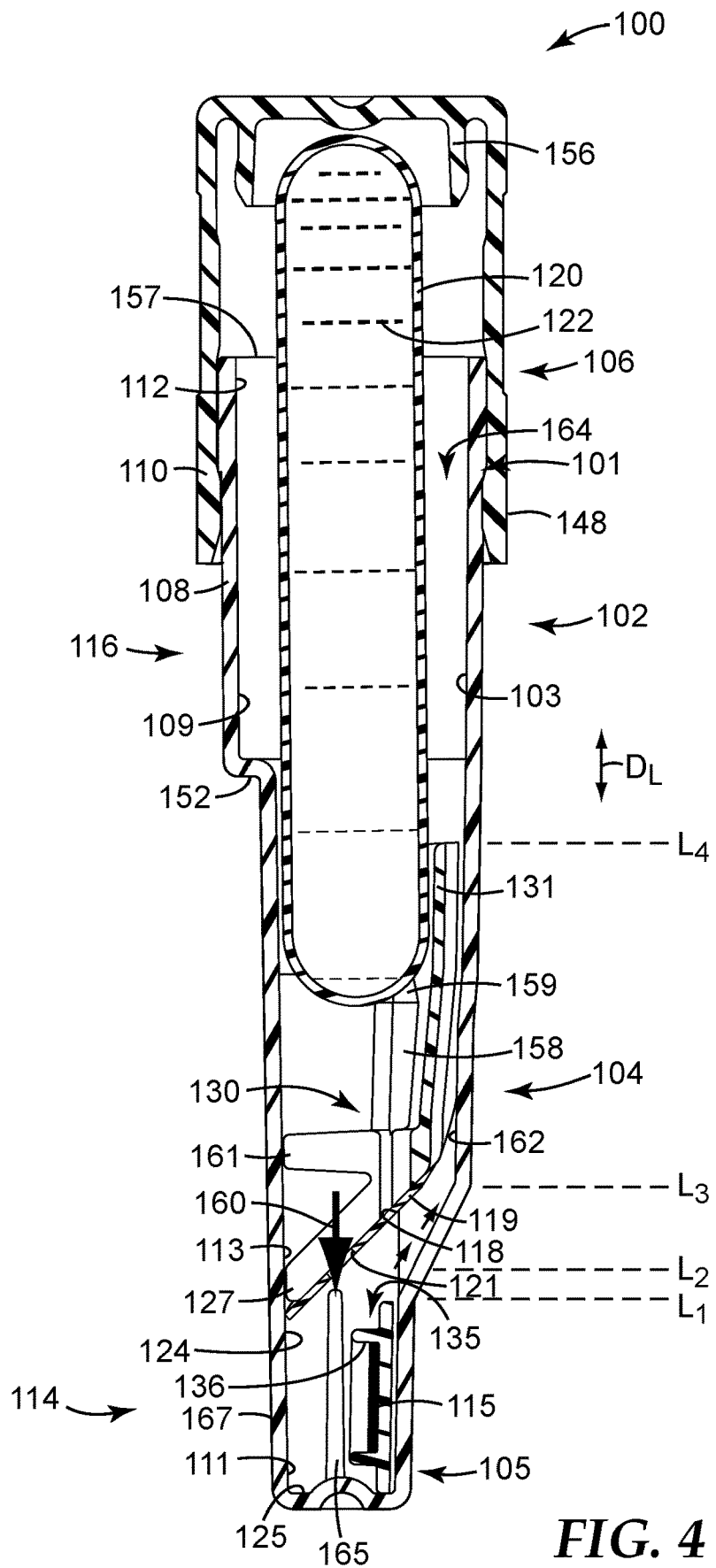
FIG. 4 is a side cross-sectional view of the biological sterilization indicator of FIGS. 1-3, taken along line 4-4 of FIG. 1, the biological sterilization indicator shown in a first state, and the second portion of the housing of the biological sterilization indicator shown in a first position.
Figure 5:
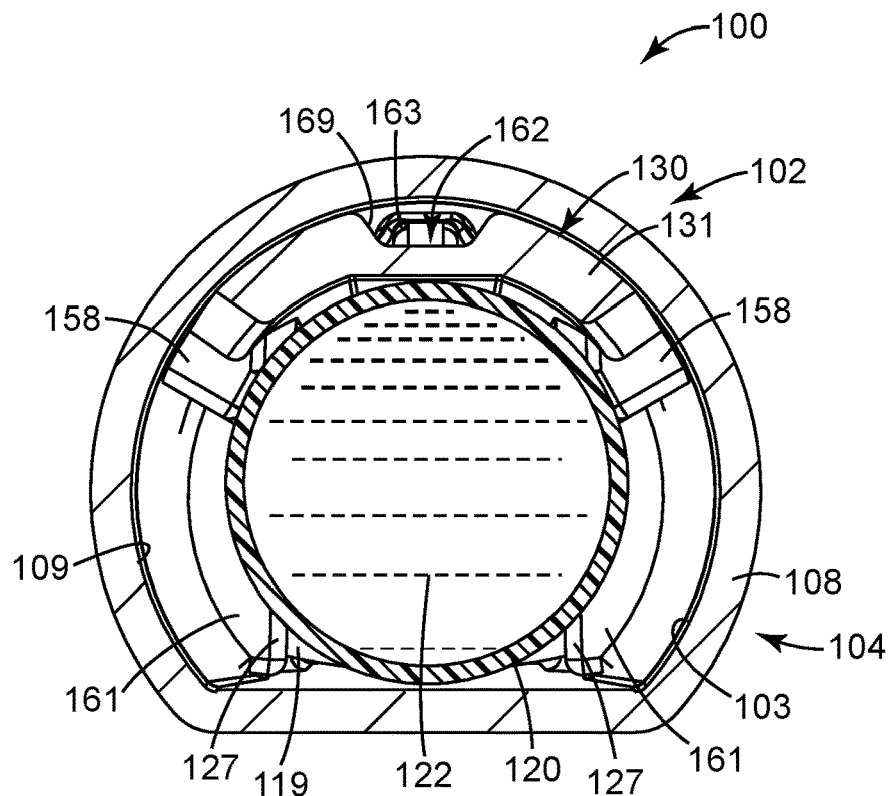
FIG. 5 is a top cross-sectional view of the biological sterilization indicator of FIGS. 1-4, taken along line 5-5 of FIG. 1.
Figure 6:
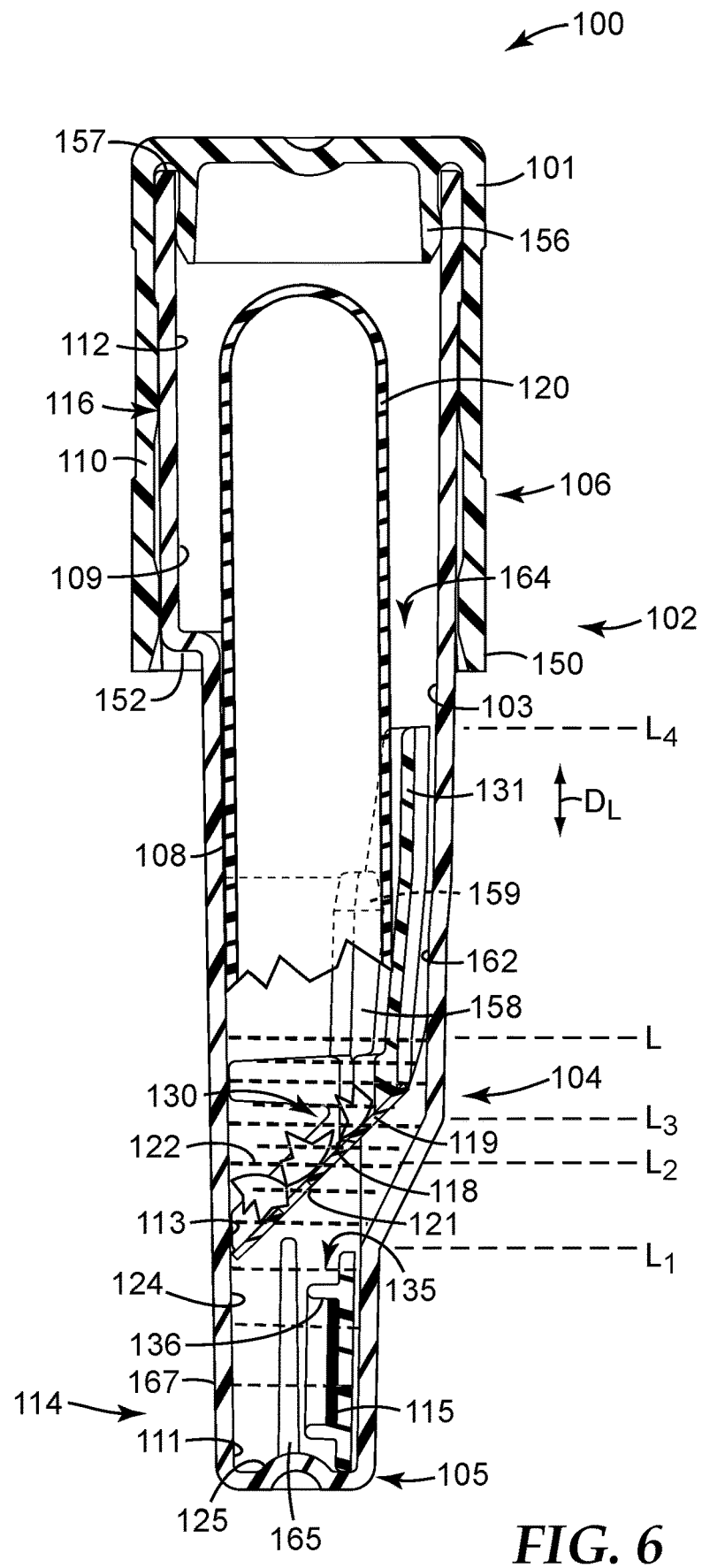
FIG. 6 is a side cross-sectional view of the biological sterilization indicator of FIGS. 1-5, the biological sterilization indicator shown in a second state, and the second portion of the housing of the biological sterilization indicator shown in a second position.

As shown in FIGS. 4 and 6, in some embodiments, the first chamber 109 can be defined by one or both of the first portion 104 and the second portion 106, particularly when the container 120 is in the first state. In addition, in some embodiments, the first chamber 109 can include a first end 112 positioned adjacent the open end 101 of the first portion 104 of the housing 102, adjacent the second portion 106 of the housing 102, and/or at least partially defined by the second portion 106. The first chamber 109 can further include a second end 13 positioned adjacent and in fluid communication with the second chamber 111 and positioned toward the closed end 105 of the housing 102. The first end 112 of the first chamber 109 can be at defined by the first portion 104 and/or the second portion 106 of the housing 102.

As further shown in FIGS. 4 and 6, in some embodiments, the second chamber 111 can include a first end 124 positioned adjacent and in fluid communication with the first chamber 109 and positioned toward the open end 101 of the housing 102, and a second end 125 at least partially defined by, including, or positioned adjacent the closed end 105 of the housing 102.

Said another way, as shown in FIGS. 4 and 6, the biological sterilization indicator 100 can include a longitudinal direction $D_L$, and in some embodiments, the first chamber 109 can be positioned longitudinally above the second chamber 111.

In some embodiments, the second chamber 111 can be at least partially defined by, can include, or can be positioned adjacent the closed end 105 of the biological sterilization indicator 100. In addition, in some embodiments, the second chamber 111 can be smaller (e.g., in volume and/or cross-sectional area) than at least one of the first chamber 109 and the volume of the liquid 122 in the container 120 that will be released when the biological sterilization indicator 100 is activated. As a result, in such embodiments, the second chamber 111 can exhibit an air-lock effect where gas (e.g. air) that is present in the second chamber 111 can inhibit fluid movement into the second chamber 111. In some embodiments, as described in greater detail below, a fluid path that allows the second chamber 111 to vent to another portion of the biological sterilization indicator 100 can facilitate fluid movement into the second chamber 111.

In some embodiments, the wall 118 (sometimes referred to as a "separating wall") can be angled or slanted, for example, oriented at a non-zero and non-right angle with respect to the longitudinal direction $D_L$ of the housing 102 (e.g., where the longitudinal direction $D_L$ extends along the length of the housing 102). Such angling or slanting of the wall 118 can facilitate the movement of the liquid 122 from the upper portion 116 to the lower portion 114 after sterilization and after the container 120 has been broken to release the liquid 122.

As shown in FIGS. 1-3, in some embodiments, the wall 118 can be at least partially formed by a change in the inner dimension of the housing 102. For example, as shown, the wall 118 can be formed by a decrease in a cross-sectional area from a first longitudinal position in the first chamber 109 to a second longitudinal position in the second chamber 111. In addition, by way of example only, the internal cross-sectional shape of the housing 102 can change at the transition from the first chamber 109 to the second chamber 111 from being substantially round (e.g., with one flat side that makes up less than 50% of the perimeter) in the first chamber 109 to substantially parallelepipedal (e.g., substantially square) in the second chamber 111.

Furthermore, in some embodiments, the wall 118 can also be at least partially formed by a change in the outer dimension of the housing 102. As shown in FIGS. 1-3, in some embodiments, the housing 102 includes a step (or ledge, overhang, transition, or the like) 123 that is angled consistently with the wall 118 (if the wall 118 is angled), and which includes a change in the outer shape and dimension of the housing 102. However, it should be understood that in some embodiments, even if the inner dimension of the housing 102 changes to create a second chamber 111 that has a different cross-sectional shape or dimension than the first chamber 109, the outer shape and dimension of the housing 102 need not change, or change consistently with the change in the inner shape and/or dimension. For example, in some embodiments, the step 123 can be oriented substantially perpendicularly with respect to the longitudinal direction $D_L$.

In some embodiments, the reservoir 103 has a volume of at least about 0.5 milliliters (mL), in some embodiments, at least about 1 mL, and in some embodiments, at least about 1.5 mL. In some embodiments, the reservoir 103 has a volume of no greater than about 5 mL, in some embodiments, no greater than about 3 mL, and in some embodiments, no greater than about 2 mL.

In some embodiments, the frangible container 120 has a volume of at least about 0.25 mL, in some embodiments, at least about 0.5 mL, and in some embodiments, at least about 1 mL. In some embodiments, the frangible container 120 has a volume of no greater than about 5 mL, in some embodiments, no greater than about 3 mL, and in some embodiments, no greater than about 2 mL.

In some embodiments, the volume of the liquid 122 contained in the frangible container 120 is at least about 50 microliters, in some embodiments, at least about 75 microliters, and in some embodiments, at least about 100 microliters. In some embodiments, the volume of the liquid 122 contained in the frangible container 120 is no greater than about 5 mL, in some embodiments, no greater than about 3 mL, and in some embodiments, no greater than about 2 mL.

In some embodiments, the first chamber 109 (i.e., formed by the upper portion 116 of the first portion 104 of the housing 102) has a volume of at least about 500 microliters (or cubic millimeters), in some embodiments, at least about 1000 microliters, in some embodiments, at least about 2000 microliters, and in some embodiments, at least about 2500 microliters. In some embodiments, the first chamber 109 has a volume of no greater than about 5000 microliters, in some embodiments, no greater than about 4000 microliters, and in some embodiments, no greater than about 3000 microliters. In some embodiments, the first chamber 109 has a volume of about 2790 microliters, or 2800 microliters.

In some embodiments, the second chamber 111 (i.e., formed by the lower portion 114 of the first portion 104 of the housing 102) has a volume of at least about 5 microliters, in some embodiments, at least about 20 microliters, and in some embodiments, at least about 35 microliters. In some embodiments, the second chamber 111 has a volume of no greater than about 250 microliters, in some embodiments, no greater than about 200 microliters, in some embodiments, no greater than about 175 microliters, and in some embodiments, no greater than about 100 microliters. In some embodiments, the second chamber 111 has a volume of about 208 microliters, or 210 microliters.

In some embodiments, the volume of the second chamber 111 is at least about 5% of the volume of the first chamber 109, and in some embodiments, at least about 7%. In some embodiments, the volume of the second chamber 111 is no greater than about 20% of the volume of the first chamber 109, in some embodiments, no greater than about 15%, in some embodiments, no greater than about 12%, and in some embodiments, no greater than about 10%. In some embodiments, the volume of the second chamber 111 is about 7.5% of the volume of the first chamber 109.

In some embodiments, the volume of the second chamber 111 is no greater than about 60% of the volume of the liquid 122 housed in the container 120, in some embodiments, no greater than about 50%, and in some embodiments, no greater than about 25%. In some embodiments, designing the second chamber 111 to have a volume that is substantially less than that of the liquid 122 housed in the container 120 can ensure that the additional liquid volume can compensate for unintended evaporation.

In some embodiments, the first chamber 109 (i.e., formed by the upper portion 116 of the first portion 104 of the housing 102) has a cross-sectional area (or average cross-sectional area) at the transition between the first chamber 109 and the second chamber 111, or at the position adjacent the second chamber 111, of at least about 25 mm$^2$; in some embodiments, at least about 30 mm$^2$; and in some embodiments, at least about 40 mm$^2$. In some embodiments, the first chamber 109 has a cross-sectional area at the transition between the first chamber 109 and the second chamber 111, or at the position adjacent the second chamber 111, of no greater than about 100 mm$^2$, in some embodiments, no greater than about 75 mm$^2$, and in some embodiments, no greater than about 50 mm$^2$.

In some embodiments, the second chamber 111 (i.e., formed by the lower portion 114 of the first portion 104 of the housing 102) has a cross-sectional area at the transition between the first chamber 109 and the second chamber 111, or at the position adjacent the first chamber 109, of at least about 5 mm$^2$, in some embodiments, at least about 10 mm$^2$, and in some embodiments, at least about 15 mm$^2$. In some embodiments, the second chamber 111 has a cross-sectional area (or average cross-sectional area) of no greater than about 30 mm$^2$, and in some embodiments, no greater than about 25 mm$^2$.

In some embodiments, the cross-sectional area of the second chamber 111 at the transition between the first chamber 109 and the second chamber 111 can be no greater than about 60% of the cross-sectional area of the first chamber 109 at the transition, in some embodiments, no greater than about 50%, in some embodiments, no greater than about 40%, and in some embodiments, no greater than about 30%.

In some embodiments, the biological sterilization indicator 100 can further include a substrate 119. In some embodiments, as shown in FIGS. 1-4 and 6, the substrate 119 can be dimensioned to be positioned adjacent the wall 118, and particularly, to rest atop the wall 118. The substrate 119 can be positioned between the upper portion 116 (i.e., the first chamber 109) and the lower portion 114 (i.e., the second chamber 111) of the biological sterilization indicator 100 and, in some embodiments, can at least partially define the first chamber 109 and the second chamber 111. As such, in some embodiments, the substrate 119 can be positioned between the container 120 and the spores 115. In some embodiments, the substrate 119 can be positioned in the first chamber 109, or on a first chamber side of the wall 118, such that the substrate 119 is not positioned in the second chamber 111.

In addition, the substrate 119 can be positioned to minimize diffusion of an assay signal (e.g., fluorescence) out of the second chamber 111. In some embodiments, depending on the material makeup of the substrate 119, the substrate 119 can also absorb dyes, indicator reagents, or other materials from solution that may inhibit accurate reading of a signal from the biological sterilization indicator 100 (i.e., "inhibitors"). In some embodiments, as shown in FIGS. 1-4, 6 and 7, the substrate 119 can include one or more apertures 121, which can be configured to control (i.e., facilitate and/or limit, depending on number, size, shape, and/or location) fluid movement between the first chamber 109 and the second chamber 111 of the biological sterilization indicator 100, and particularly, which can facilitate movement of the liquid 122 to the spores 115 when the container 120 is fractured. By way of example only, particular benefits or advantages were observed when the aperture 121 was positioned to the front of (or "forward of") the center of the substrate 119, as shown. In the embodiment illustrated in FIGS. 1-7, the "front" of the biological sterilization indicator 100 or components therein can generally be described as being toward a flat face 126. In general, the "front" of the biological sterilization indicator 100 can refer to the portion of the biological sterilization indicator 100 that will be interrogated by a reading apparatus.

In addition, by way of example only, the aperture 121 is illustrated as being circular or round; however, other cross-sectional aperture shapes are possible and within the scope of the present disclosure. Furthermore, by way of example only, and as shown in FIG. 3, the substrate 119 is shaped to substantially fill the first chamber cross-sectional area at the transition between the first chamber 109 and the second chamber 111. However, other shapes of the substrate 119 are possible and can be adapted to accommodate the housing 102, the first chamber 109, the second chamber 111, the wall 118, or another component of the biological sterilization indicator 100.

As mentioned above, the second chamber 111 can include a volume to be interrogated. Such a volume can be assayed for spore viability to determine the lethality or effectiveness of a sterilization procedure. In some embodiments, the volume to be interrogated can be all or a portion of the second chamber 111. In some embodiments, the substrate 119 can be positioned outside of the volume to be interrogated, which can minimize the number of structures in the volume that may interfere with the assaying processes. For example, in some embodiments, the substrate 119 can be positioned such that the substrate 119 is not in direct contact with at least one of the spores 115, the spore carrier 135, and the spore reservoir 136. In some embodiments, the substrate 119 can be positioned such that the substrate 119 is not located between a detection system (e.g., an optical detection system, such as a fluorescence excitation source and an emission detector) and at least one of the spores 115, the spore carrier 135, and the spore reservoir 136. The substrate 119 can have the above positions when the container 120 is in the first state and/or the second state, but particularly, when the container 120 is in the second state.

In some embodiments, substrate position in the biological sterilization indicator 100 can affect the correlation of a rapid detection system for spore viability (e.g., fluorescence detection) with a slower (e.g., overnight or 24-hr) detection system (e.g., a pH indicator that can exhibit a color change (e.g., in 24 hr) in response to spore growth). For example, in some embodiments, the substrate 119 can improve the correlation of fluorescence readings at various timepoints with growth results after 24 hours, as shown in Example 1 below. Particularly, when the substrate 119 is positioned in a "first" position—as described herein and as shown in FIGS. 1, 2, and 4-7—the fluorescence can accurately correlate to growth. As shown in Example 1, such correlation can be an improvement over other substrate positions and biological sterilization indicators with no substrate.

In addition, the substrate 119 can be positioned in the biological sterilization indicator 100 such that the substrate 119 is not in direct contact with the container 120 when the container 120 is in the first state. For example, in some embodiments, the substrate 119 can be positioned in the first chamber 109 (e.g., adjacent a bottom end (e.g., the second end 113) of the first chamber 109), but even in such embodiments, the substrate 119 can be positioned such that the substrate 119 does not contact the container 120. For example, as shown in FIGS. 1-2 and 4-6, in some embodiments, the insert 130 can be positioned between the container 120 and the substrate 119 when the container 120 is in the first state, such that the insert 130 holds the container 120 in the first state. The insert 130, or a portion thereof, can be positioned adjacent the substrate 119. For example, as shown in the illustrated embodiment, the substrate 119 can be positioned between (e.g., sandwiched between) the insert 130 and the wall 118. As such, in some embodiments, the substrate 119 can be positioned between the insert 130 and the second chamber 111. In some embodiments, when the container 120 is in the second state, fractured portions, or shards, of the container 120 may come into contact with the substrate 119, but in some embodiments, the fracture portions of the container 120 do not come into contact with the substrate 119.

As mentioned above, in some embodiments, the substrate 119 can be positioned and configured to control or affect fluid flow in the biological sterilization indicator 100, and particularly, to control fluid flow between the first chamber 109 and the second chamber 111. For example, in some embodiments, the substrate 119 can be configured (e.g., sized, shaped, oriented, and/or constructed of certain materials) to control the rate at which a sterilant is delivered to the second chamber 111 (and to the spores 115), and can thereby control the "kill rate" of the spores 115. For example, the sterilant delivery rate can be less than it otherwise would be if the substrate 119 were not present between the first chamber 109 and the second chamber 111. That is, in some embodiments, the substrate 119 can control the kill rate by selectively protecting the spores 115. In some embodiments, the substrate 119 can serve as a "valve" for controlling fluid flow, and particularly, for controlling sterilant delivery, in the biological sterilization indicator 100. Furthermore, in some embodiments, the substrate 119 can have properties that enhance or modulate a response generated by the spores 115, for example, if the spores 115 survive a sterilization process.

Furthermore, in some embodiments, the substrate 119 can be configured (e.g., sized, shaped, positioned, oriented, and/or constructed of certain materials) to control the rate at which detectable products diffuse out of the volume to be interrogated. In some embodiments, the detectable product can include a signal (e.g., a fluorescent signal) that indicates spore viability, and in some embodiments, the detectable product can be the spore(s) 115 itself. Controlling the diffusion of detectable products out of the volume to be interrogated can be particularly useful in embodiments in which the volume of the liquid 122 is greater than the volume of the second chamber 111 (or of the volume to be interrogated), because the liquid 112 in such embodiments can extend in the biological sterilization indicator 100 to a higher level than the second chamber 111 (or the volume to be interrogated) when the container 120 is in its second, fractured, state. In such embodiments, detectable products can be free to move throughout the full volume of the liquid 122 (i.e., to a volume outside of the volume to be interrogated), unless there is some barrier or means for controlling such diffusion, such as the substrate 119. For example, in some embodiments, the substrate 119 can be positioned at a level just above the volume to be interrogated (i.e., below the level of the liquid 122), to inhibit movement of the detectable products to the portion of the liquid 122 that is positioned above the substrate 119.

In some embodiments, the substrate 119 can control sterilant delivery rate (e.g., into the second chamber 111) and/or the diffusion rate of detectable products (e.g., out of the second chamber 111) by providing a physical barrier or blockage to the sterilant and/or the detectable products. Such a physical barrier can also function to collect broken portions of the container 120 when the container 120 is in the second, fractured, state to inhibit movement of the broken portions into the volume to be interrogated where the broken portions could block, refract, reflect, or otherwise interfere with detection processes (e.g., optical detection processes).

In addition, in some embodiments, the liquid 122, either before or after coming into fluid communication with the spores 115, can include one or more inhibitors, or other components, that may interfere with an accurate assay or detection process. In some embodiments, examples of inhibitors can include at least one of dyes, indicator reagents, other materials or substances that may inhibit a reaction (e.g., an enzymatic reaction) necessary for detection of spore viability (e.g., salts, etc.), other materials or substances that may interfere with the detection process, or combinations thereof. In such embodiments, the substrate 119 can be configured to absorb and/or selectively concentrate one or more inhibitors from the liquid 122, or at least from the volume of the liquid 122 to be interrogated. Determining that the substrate receives and concentrates the indicator reagent (or biological derivative thereof) can be accomplished by fluidically contacting an aqueous medium comprising the indicator reagent (or biological derivative thereof) with the substrate for a period of time and analyzing the substrate for the presence of the reagent (or biological derivative thereof), as shown in Example 3.

For example, in some embodiments, more than one indicator reagent can be present in the liquid 122, either before contacting the spores 115 or as a result of contacting the spores 115. In such embodiments, while a first indicator reagent (e.g., used for fluorescence detection) may be necessary for spore viability detection, a second indicator reagent (e.g., a pH indicator) may interfere with the detection of the first indicator reagent. By way of example only, in embodiments in which the second indicator reagent is a pH indicator (e.g., one or more of the pH indicators described below), the pH indicator may conflict or interfere with the fluorescence reading of the first indicator reagent, for example, in embodiments in which the pH indicator emits electromagnetic radiation at a wavelength that is similar to the spectral band of the fluorescence of the first indicator reagent (e.g., when the pH indicator exhibits a color shift). In such embodiments, the substrate 119 can be configured (e.g., formed of an appropriate material) to absorb and/or selectively concentrate the second indicator reagent when positioned in contact with the liquid 122 to reduce the concentration of the second indicator reagent in the liquid 122, or at least in the volume of the liquid 122 to be interrogated.

Fluorogenic enzyme substrates according to Formula I (hereinabove) can be used in methods to detect predetermined biological activities, and are suitable for use as an indicator reagent according to the present disclosure. For example, a first indicator reagent can include a reagent that has a first absorption spectrum and, thus, it absorbs light in the ultraviolet and/or visible wavelengths of the electromagnetic spectrum.

In order to detect a biological activity comprising an enzyme, the operator should be knowledgeable concerning the enzyme activity to be detected and the enzyme substrates that will react with the enzyme so as to produce a product which can be detected either by its fluorescence, color, etc. (see M. Roth, Methods of Biochemical Analysis, Vol. 7, D. Glock, Ed., Interscience Publishers, New York, NY, 1969, which is incorporated herein by reference in its entirety). The appropriate enzyme substrate to be utilized will depend upon the biological activity to be detected.

A person of ordinary skill in the relevant art will recognize that the amount of absorbance of any particular wavelength of light by a solution containing a first indicator reagent will be influenced by the concentration of the first indicator reagent in the solution and the molar extinction coefficient of the indicator reagent at the selected wavelength. The skilled person will also recognize that the amount of light emission of any particular wavelength by a solution containing a biological derivative of a second indicator reagent will be influenced by the concentration of the second biological derivative in the solution and the fluorescence quantum yield of the biological derivative. Therefore, the concentration of the first indicator reagent in the liquid mixture can be selected in conjunction with an appropriate substrate to permit i) the substrate to remove enough first indicator substrate from the liquid mixture to allow more sensitive detection of the second biological derivative and ii) the first indicator reagent (or biological derivative thereof) to be easily detected on the substrate material.

In addition, in some embodiments (e.g., in embodiments in which the wall 118 is slanted and the substrate 119 is positioned adjacent the wall 118), the substrate 119 can be angled or slanted, for example, oriented at a non-zero and non-right angle with respect to the longitudinal direction $D_L$ of the housing 102. Such angling or slanting of the substrate 119 can facilitate the movement of the liquid 122 from the first chamber 109 to the second chamber 111 after sterilization and after the container 120 has been broken to release the liquid 122.

In some embodiments, the substrate 119 can be formed of a variety of materials to accomplish one or more of the above functions. Examples of substrate materials can include, but are not limited to, cotton, glass wool, cloth, nonwoven polypropylene, nonwoven rayon, nonwoven polypropylene/rayon blend, nonwoven nylon, nonwoven glass fiber or other nonwoven fibers, filter papers, microporous hydrophobic and hydrophilic films, glass fibers, open celled polymeric foams, and semi-permeable plastic films (e.g., particle filled films, thermally induced phase separation (TIPS) membranes, etc.), and combinations thereof. For example, in embodiments in which the substrate 119 can be used to selectively concentrate one more indicator reagents (e.g., bromocresol purple), the substrate 119 can be formed of a charged nylon (such as a reprobing, charged transfer membrane available from GE Water & Process Technologies, Trevose, PA, under the trade designation "MAGNAPROBE" (e.g., 0.45 micron pore size, 30 cm×3 m roll, Catalog No. NP0HY00010, Material No. 1226566)).

In some embodiments, at least a portion of one or more of the insert 130, the wall 118, and/or the substrate 119, or an opening therein, can provide fluid communication between the first chamber 109 (e.g., in the upper portion 116) and the second chamber 111 (e.g., in the lower portion 114), and/or can control the fluid communication between the first chamber 109 and the second chamber 111 (e.g., by controlling the extent of fluid connection between the first chamber 109 and the second chamber 111).

The biological sterilization indicator 100 can include a first fluid path 160 that can be positioned to fluidly couple the first chamber 109 and the second chamber 111, and which can allow sterilant (e.g., during sterilization, when the container 120 is in a first, unfractured, state) and/or the liquid 122 (e.g., after sterilization and during activation, when the container 120 is in a second, fractured, state) to reach the spores 115. In the illustrated embodiment the first fluid path 160 can generally be defined by one or more of the following: (1) the insert 130, e.g., via an aperture 177 described below, an opening formed in the insert 130, and/or any open spaces around the insert 130, such as between the insert 130 (e.g., a front portion thereof) and the housing 102; (2) the wall 118, e.g., the aperture 117 defined by the wall 118; (3) the substrate 119, e.g., the aperture 121 formed therein, or any open spaces around the substrate 119, such as between the substrate 119 (e.g., a front portion thereof) and the housing 102; (4) the housing 102, e.g., any openings or spaces formed therein; and combinations thereof. As a result, the first fluid path 160 is generally represented in the illustrated embodiment by an arrow in FIGS. 4 and 7.

The biological sterilization indicator 100 can further include a second fluid path 162 positioned to fluidly couple the second chamber 111 with another chamber or portion of the biological sterilization indicator 100, such as the first chamber 109. The second fluid path 162 can be further positioned to allow gas that was previously present in the second chamber 111 to be displaced and to exit the second chamber 111, for example, when the sterilant and/or the liquid 122 is moved into the second chamber 111. As such, the second fluid path 162, which is described in greater detail below, can serve as an internal vent in the biological sterilization indicator 100.

In some embodiments, the substrate 119 can provide a physical barrier or blockage between the first chamber 109 and the second chamber 111 which can allow for at least one of the following: controlling the sterilant delivery rate/kill rate at which sterilant is delivered into the second chamber 111; controlling the diffusion of spores 115 and/or detectable products out of the second chamber 111; controlling the delivery rate of the liquid 122 to the second chamber 111 (and to the spores 115) when the container 120 is in the second, fractured, state; or a combination thereof.

Because, in some embodiments, the substrate 119 can provide a physical barrier to delivering the liquid 122 to the second chamber 111 during activation (i.e., when the container 120 is in the second state), aperture 121 in the substrate 119 and/or the angle of the substrate 119 can be controlled to effect a desired liquid delivery rate. In addition, or alternatively, the second fluid path 162 can provide a vent for any gas or air that is trapped in the second chamber 111 to facilitate moving the liquid 122 through or past the substrate 119 and into the second chamber 111 when desired.

In addition, or alternatively, the housing 102 can be configured (e.g., formed of an appropriate material and/or configured with microstructured grooves or other physical surface modifications) to facilitate moving the liquid 122 to the second chamber 111 when desired.

As shown in FIGS. 1-7, the biological sterilization indicator 100 can further include an insert 130. In some embodiments, the insert 130 can be adapted to hold or carry the container 120, such that the container 120 is held intact in a location separate from the spores 115 during sterilization. That is, in some embodiments, the insert 130 can include (or function as) a carrier 132 (see FIG. 3) for the container 120, particularly, before the container 120 is broken during the activation step (i.e., the step in which the liquid 122 is released from the container 120 and introduced to the spores 115, which can occur after a sterilization process). In some embodiments, the insert 130 can be further adapted to allow the container 120 to move at least somewhat in the housing 102, e.g., longitudinally with respect to the housing 102. The insert 130 of the illustrated embodiment is described in greater detail below.

In some embodiments, the biological sterilization indicator 100 can further include a spore carrier 135, as shown in FIGS. 1-4 and 6. However, in some embodiments, the insert 130 can be modified to include a portion adapted to house the spores 115. For example, in some embodiments, the insert 130 and the spore carrier 135 can be integrally formed as one insert comprising a first portion adapted to hold and eventually fracture the container 120, when desired, and a second portion adapted to house the spores 115 in a region of the biological sterilization indicator 100 that is separate from the container 120 during sterilization (i.e., prior to fracture).

As shown in FIGS. 1-4 and 6, the spore carrier 135 can include a spore reservoir 136 (which can also be referred to as a depression, divot, well, recess, or the like), in which the spores 115 can be positioned, either directly or on a substrate. In embodiments employing a nutrient medium that is positioned to be mixed with the liquid 122 when it is released from the container 120, the nutrient medium can be positioned near or in the spore reservoir 136, and the nutrient medium can be mixed with (e.g., dissolved in) the water when the water is released from the container 120. By way of example only, in embodiments in which the nutrient medium is provided in a dry form, the dry form can be present within the reservoir 103, the spore reservoir 136, on a substrate for the spores, or a combination thereof. In some embodiments, a combination of liquid and dry nutrient media can be employed.

In some embodiments, the spore reservoir 136 has a volume of at least about 1 microliter, in some embodiments, at least about 5 microliters, and in some embodiments, at least about 10 microliters. In some embodiments, the spore reservoir 136 has a volume of no greater than about 250 microliters, in some embodiments, no greater than about 175 microliters, and in some embodiments, no greater than about 100 microliters.

As shown in FIGS. 4 and 6, in some embodiments, the biological sterilization indicator 100 can further include a rib or protrusion 165 that can be coupled to or integrally formed with a wall 108 of the housing 102, which can be positioned to maintain the spore carrier 135 in a desired location in the housing 102 and/or at a desired angle or orientation, for example, with respect to detection systems (e.g., optical detection systems) of the reading apparatus 12.

As shown in FIGS. 1-4 and 6, the second portion 106 of the housing 102 can be adapted to be coupled to the first portion 104. For example, as shown, the second portion 106 can be adapted to be coupled to the upper portion 116 (e.g., the first end 101) of the first portion 104 of the housing 102. In some embodiments, as shown in FIGS. 1-4, the second portion 106 can be in the form of a cap that can be dimensioned to receive at least a portion of the first portion 104 of the housing 102.

As shown in FIGS. 1-2 and 4-5, during sterilization and before activation, the second portion 106 can be in a first "unactivated" position 148 with respect to the first portion 104, and the container 120 can be in a first, intact, state. As shown in FIG. 6, the second portion 106 of the housing 102 can be moved to a second "activated" position 150 (e.g., where the second portion 106 is fully depressed) with respect to the first portion 104, and the container 120 can be in a second, fractured, state. For example, after sterilization, the biological sterilization indicator 100 can be activated by moving the second portion 106 from the first position 148 to the second position 150 (i.e., a sufficient amount) to cause fracturing of the container 120 and to release the liquid 122 from the container 120, to allow the liquid 122 to be in fluid communication with the spores 115. The biological sterilization indicator 100 can be activated prior to positioning the biological sterilization indicator 100 in a well of a reading apparatus, after positioning the biological sterilization indicator 100 in the well, or as the biological sterilization indicator 100 is positioned in the well (i.e., the biological sterilization indicator 100 can be slid into place in the reading apparatus, and the second portion 106 can continue to be pressed until it is in its second position 150, e.g., in which the bottom of the well provides sufficient resistance to move the second portion 106 to its second position 150). The second position 150 can be located closer to the closed end 105 of the first portion 104 of the biological sterilization indicator 100 than the first position 148.

As shown in the illustrated embodiment, in some embodiments, the first portion 104 of the housing 102 can include a step, overhang, or flat-to-round transition 152. The step 152 is shown as being exposed when the second portion 106 is in its first position 148 and as being obscured or covered when the second portion 106 is in its second position 150. As such, the step 152 can be detected to determine whether the second portion 106 is in the first position 148 (i.e., the biological sterilization indicator 100 is unactivated), or is in the second position 150 (i.e., the biological sterilization indicator 100 is activated). Using such features of the biological sterilization indicator 100 to determine a status of the biological sterilization indicator 100, for example, to confirm whether the biological sterilization indicator 100 has been activated, is described in greater detail in co-pending U.S. Application No. 61/409,042. The longitudinal position of the step 152 is shown by way of example only; however, it should be understood that the step 152 can instead be located at a different longitudinal position (e.g., closer to the closed end 105 of the biological sterilization indicator 100), or, in some embodiments, the transition from a rounded portion to a flat face can be gradual, tapered, or ramped.

A variety of coupling means can be employed between the first portion 104 and the second portion 106 of the housing 102 to allow the first portion 104 and the second portion 106 to be removably coupled to one another, including, but not limited to, gravity (e.g., one component can be set atop another component, or a mating portion thereof), screw threads, press-fit engagement (also sometimes referred to as "friction-fit engagement" or "interference-fit engagement"), snap-fit engagement, magnets, adhesives, heat sealing, other suitable removable coupling means, and combinations thereof. In some embodiments, the biological sterilization indicator 100 need not be reopened and the first portion 104 and the second portion 106 need not be removably coupled to one another, but rather can be permanently or semi-permanently coupled to one another. Such permanent or semi-permanent coupling means can include, but are not limited to, adhesives, stitches, staples, screws, nails, rivets, brads, crimps, welding (e.g., sonic (e.g., ultrasonic) welding), any thermal bonding technique (e.g., heat and/or pressure applied to one or both of the components to be coupled), snap-fit engagement, press-fit engagement, heat sealing, other suitable permanent or semi-permanent coupling means, and combinations thereof. One of ordinary skill in the art will recognize that some of the permanent or semi-permanent coupling means can also be adapted to be removable, and vice versa, and are categorized in this way by way of example only.

As shown in FIGS. 4 and 6, the second portion 106 can be movable between a first longitudinal position 148 with respect to the first portion 104 and a second longitudinal position 150 with respect to the first portion 104; however, it should be understood that the biological sterilization indicator 100 could instead be configured differently, such that the first and second positions 148 and 150 are not necessarily longitudinal positions with respect to one or both of the first portion 104 and the second portion 106 of the housing 102.

The second portion 106 can further include a seal 156 (e.g., a projection, a protrusion, a flap, flange, O-ring, or the like, or combinations thereof) that can be positioned to contact the first end 101 of the first portion 104, and particularly, an open upper end 157 of the first portion 104 to close or seal (e.g., hermetically seal) the biological sterilization indicator 100 after the second portion 106 has been moved to the second position 150 and the liquid 122 has been released from the container 120 (i.e., when the container 120 is in a second, fractured, state). That is, the spores 115 can be sealed from ambience when the container 120 is in the second state. The seal 156 can take a variety of forms and is shown in FIGS. 4 and 6 by way of example as forming an inner ring or cavity that together with the wall 110 of the second portion 106 is dimensioned to receive the upper end 157 of the first portion 104 of the housing 102 to seal the biological sterilization indicator 100.

In some embodiments, one or both of the seal 156 and the upper end 157 can further include a structure (e.g., a protrusion) configured to engage the other of the upper end 157 and the seal 156, respectively, in order to couple the second portion 106 of the housing 102 to the first portion 104 of the housing 102.

In addition, in some embodiments, the second portion 106 of the housing 102 can be coupled to the first portion 104 of the housing 102 to seal the biological sterilization indicator 100 from ambience after activation. Such sealing can inhibit contamination, evaporation, or spilling of the liquid 122 after it has been released from the container 120, and/or can inhibit contamination of the interior of the biological sterilization indicator 100.

The seal 156 can be configured to have a length in the longitudinal direction $D_L$ of the biological sterilization indicator 100 to accommodate different degrees or levels of closure. That is, in some embodiments, the "second position" 150 of the second portion 106 of the housing 102 can be any position in which at least a portion of the seal 156 has engaged a portion (e.g., the upper end 157) of the first portion 104 of the housing 102 such that the interior of the biological sterilization indicator 100 is sealed from ambience. The biological sterilization indicator 100 and the biological sterilization indicator system 10 can correspondingly be configured such that if the reading apparatus 12 detects that the second portion 106 has moved to the second position 150, the user knows that the seal 156 is engaged.

The insert 130 will now be described in greater detail.

As shown in FIGS. 1-2 and 4, during sterilization and before activation, the second portion 106 can be in a first position 148 with respect to the first portion 104. In the first position 148, the container 120 can be held intact in a position separate from the lower portion 114, the second chamber 111, or the spores 115, and the liquid 122 can be contained within the container 120.

As shown in FIG. 6, after sterilization, the biological sterilization indicator 100 can be activated to release the liquid 122 from the container 120 to move the liquid 122 to the second chamber 111. That is, the second portion 106 of the housing 102 can be moved to a second position 150 with respect to the first portion 104. When the second portion 106 is moved from the first position 148 to the second position 150, the seal 156 of the second portion 106 of the housing 102 can engage the upper end 157 of the first portion 104 to seal the reservoir 103 of the biological sterilization indicator 100 from ambience. In such embodiments, the second portion 106 can reversibly engage the first portion 104 in the second position 150, and in some embodiments, the second portion 106 can irreversibly engage the first portion 104. However, it should be understood that the structures and coupling means for the first portion 104 and the second portion 106 are shown in illustrated embodiment by way of example only, and any of the above-described coupling means can instead be employed between the first portion 104 and the second portion 106 of the housing 102.

The insert 130 can be adapted to hold or carry the container 120, such that the container 120 is held intact in a location separate from the spores 115 during sterilization. That is, as mentioned above, in some embodiments, the insert 130 can include (or function as) a carrier 132 for the container 120, particularly, before the container 120 is broken during the activation step (i.e., the step in which the liquid 122 is released from the container 120 and introduced to the spores 115, which typically occurs after a sterilization process).

In addition, the insert 130 can be adapted to hold the container 120 intact in a position in the housing 102 that maintains at least a minimal spacing (e.g., a minimal cross-sectional area of space) between the container 120 and the housing 102 and/or between the container 120 and any other components or structures in the housing 102 (e.g., at least a portion of the insert 130, such as the carrier 132, etc.), for example, to maintain a substantially constant sterilant path 164 in the biological sterilization indicator 100. In some embodiments, the insert 130 can be adapted to hold the container 120 in a substantially consistent location in the housing 102.

In some embodiments, as shown in FIG. 3, at least a portion of the housing 102 can include a tapered portion 146 in which the housing 102 (e.g., the wall 108 and/or an inner surface thereof) generally tapers in the longitudinal direction $D_L$ of the housing 102. As a result, the cross-sectional area in the housing 102 can generally decrease along the longitudinal direction $D_L$.

In some cases, without providing the means to maintain at least a minimal spacing around the container 120 (e.g., between the container 120 and surrounding structure), there can be a possibility that the container 120 can become positioned in the housing 102 (e.g., in the tapered portion 146) in such a way that it obstructs or blocks the sterilant path 164. However, the biological sterilization indicator 100 of the present disclosure is designed to inhibit this from occurring. For example, in the illustrated embodiment, the insert 130 (and particularly, the carrier 132) can be configured to hold the container 120 out of the tapered portion 146 of the housing 102, such that at least a minimal cross-sectional area is maintained around the container 120 in any orientation of the biological sterilization indicator 100 prior to activation. For example, in the embodiment illustrated in FIGS. 1-5, even if the biological sterilization indicator 100 is tipped upside down, the container 120 may fall away from contact with the insert 130, but in no orientation, is the container 120 moved any closer to the tapered portion 146, or the spores 115 until activation of the biological sterilization indicator 100. In addition, until activation, at least a minimal spacing (and particularly, a cross-sectional area of that spacing) between the container 120 and the housing 102 and/or the insert 130 can be maintained to provide a substantially constant sterilant path 164, for example, around the container 120, through the first fluid path 160 and into the second chamber 111.

In some embodiments, the relative sizing and positioning of the components of the biological sterilization indicator 100 can be configured such that, before activation, the container 120 is held intact in a substantially consistent location in the biological sterilization indicator 100. Such a configuration can provide a substantially constant sterilant path 164 and can maintain the container 120 in a position such that the container 120 is not able to move substantially, if at all, in the biological sterilization indicator 100 before activation.

In some embodiments, at least a portion of the insert 130 can be adapted to allow the container 120 to move in the housing 102, e.g., longitudinally with respect to the housing 102, between a first (longitudinal) position in which the container 120 is intact and a second (longitudinal) position in which at least a portion of the container 120 is fractured. By way of example only, the insert 130 can include one or more projections or arms 158 (two projections 158 spaced about the container 120 are shown by way of example only) adapted to hold and support the container 120 before activation and to allow the container 120 to move in the housing 102 during activation, for example, when the second portion 106 is moved with respect to the first portion 104 of the housing 102. The projections 158 can also be adapted (e.g., shaped and/or positioned) to fracture the container 120 in a desired manner when the biological sterilization indicator is activated. As a result, the insert 130 can sometimes function to hold the container 120 intact before activation, and can function to break the container 120 during activation. As a result, the insert 130, or a portion thereof, can sometimes be referred to as a "carrier" (e.g., the carrier 132) and/or a "breaker."

By way of example only, the projections 158 are shown in FIGS. 1 and 3-7 as being coupled to a base or support 127 adapted to abut the separating wall 118. For example, the base 127 can be dimensioned to be received in the reservoir 103 and dimensioned to sit atop, abut, or otherwise cooperate with or be coupled to the separating wall 118. Such coupling with an internal structure of the biological sterilization indicator 100 can provide the necessary resistance and force to break the container 120 when desired. In some embodiments, however, the insert 130 does not include the base 127, and the projections 158 can be coupled to or form a portion of the housing 102. In some embodiments, the insert 130 is integrally formed with or provided by the housing 102.

As shown, the insert 130 can further include a sidewall 131 that connects the projections 158 and is shaped to accommodate an inner surface of the housing 102 and/or an outer surface of the container 120. Such a sidewall 131 can provide support and rigidity to the projections 158 to aid in reliably breaking the container 120 in a consistent manner. The sidewall 131 can also be shaped and dimensioned to guide the container 120 in a desired manner as it is moved in the housing 102 during activation, for example, to contact the projections 158 in a desired way to reliably fracture the container 120. The sidewall 131 and/or the wall 108 of the housing 102 (or an inner surface thereof) can also be shaped to define at least a portion of the second fluid path 162 of the biological sterilization indicator 100, for example, between an outer surface of the insert 130 and an inner surface of the housing 102. For example, in some embodiments, as shown in FIGS. 1-2, 5 and 7, the sidewall 131 of the insert 130 can include a channel (or groove, recess, or the like) 169 configured to form at least a portion of the second fluid path 162.

The second fluid path 162 can function as an "internal vent" or a "vent channel" within the biological sterilization indicator 100 to allow gas (e.g., displaced gas, such as air that had been trapped in the second chamber 111 (e.g., near the closed end 105 of the biological sterilization indicator 100) to escape the second chamber 111 of the biological sterilization indicator 100. In some embodiments, the second fluid path 162 can provide an escape, or internal vent, for a gas present in the second chamber 111 during activation to facilitate moving the liquid 122 into the second chamber 111 from the first chamber 109 as it is released from the container 120. Additionally or alternatively, in some embodiments, the second fluid path 162 can provide an escape, or internal vent, for a gas present in the second chamber 111 during sterilization to facilitate moving a sterilant into the second chamber 111 of the biological sterilization indicator 100 and to the spores 115, with more efficient sterilant penetration into the second chamber 111.

Figure 7:
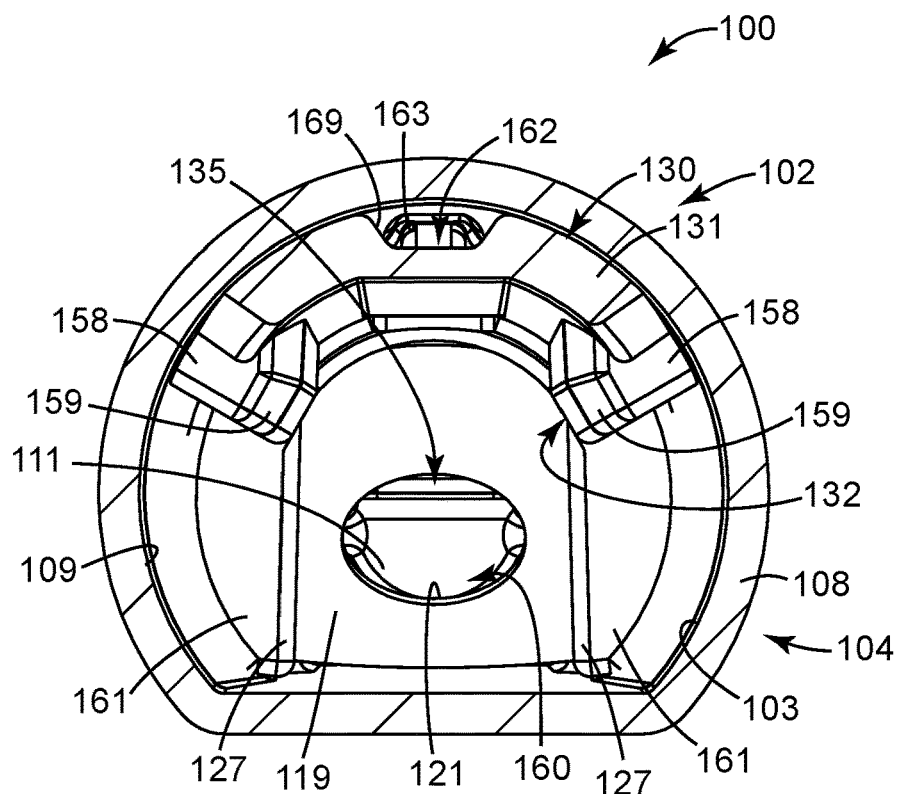
FIG. 7 is a top cross-sectional view of the biological sterilization indicator of FIGS. 1-6, with portions removed for clarity.

By way of example only, as shown in FIGS. 2 and 7, the second fluid path 162 can be at least partially defined by both a portion of the insert 130 (e.g., the channel 169) and by a channel (or groove, recess, or the like) 163 formed in the wall 108 of the housing 102 (e.g., in an inner surface of the wall 108). However, it should be understood that in some embodiments, the second fluid path 162 can be formed entirely of the housing 102 or of various combinations of other components of the biological sterilization indicator 100 such that the second fluid path 162 provides fluid connection between the second chamber 111 and another internal portion or region of the biological sterilization indicator 100. For example, the second fluid path 162 need not be formed by both the housing 102 and the insert 130, but can be formed by one of these components, or other components. In addition, as shown in FIGS. 2 and 7, the channel 163 that defines at least a portion of the second fluid path 162 is molded into an outer surface and an inner surface of the housing 102, such that the channel 163 is visible on the inside and the outside of the housing 102. However, the outer surface of the housing 102 need not include such a shape, and rather, in some embodiments, the outer surface of the housing 102 can remain substantially uniform or unchanged, and the inner surface of the housing 102 (e.g., a wall 108 of the housing 102) can include the channel 163.

Furthermore, in some embodiments, neither the insert 130 nor the housing 102 include the channel 169 or the channel 163, respectively, but rather the insert 130 and the housing 102 are shape and dimensioned such that a space or gap is provided between the insert 130 and the housing 102 that is in fluid communication with the second chamber 111, and such a space or gap functions as the second fluid path 162.

As further shown in FIGS. 4 and 6, in some embodiments, the first fluid path 160 and/or the second fluid path 162 can be at least partially defined by one or more of the wall 118, the substrate 119, the insert 130, and the housing 102. In addition, at least one of the first fluid path 160 and the second fluid path 162 can be defined at least partially by the spore carrier 135, or a portion thereof.

In some embodiments, the biological sterilization indicator 100 can include the following components arranged in the following order when the container 120 is in a first, unfractured, state: the closed end 105 of the housing 102 of the biological sterilization indicator 100, the second chamber 111, the substrate 119, the insert 130, the first chamber 109, the container 120, the open end 101 of the housing 102 (or the second portion 106 of the housing 102).

As shown in the illustrated embodiment, the second fluid path 162 can allow the second chamber 111 to vent to another portion of the biological sterilization indicator 100, such as the first chamber 109. In some embodiments, the second fluid path 162 can exit the second chamber 111 at a position located above (e.g., vertically above) the position at which the first fluid path 160 enters the second chamber 111, particularly, in embodiments in which the second fluid path 162 vents the second chamber 111 back to the first chamber 109. Said another way, in some embodiments, the second fluid path 162 can extend from the second chamber 111 to a position (e.g., a fourth level $L_4$, described below) in the biological sterilization indicator 100 that is above the position (e.g., a first level $L_1$ or a second level $L_2$, described below) at which the first fluid path 160 enters the second chamber 111. Furthermore, in some embodiments, the position at which the second fluid path 162 enters the first chamber 109 can be located above (e.g., vertically above) the position at which the first fluid path 160 enters the second chamber 111.

In some embodiments, the first fluid path 160 can be positioned to fluidly couple the second chamber 111 with a proximal portion of the biological sterilization indicator 100 (e.g., a portion of the first chamber 109 that is located proximally or adjacent the second chamber 111, e.g., at the first level $L_1$ and/or the second level $L_2$), and the second fluid path 162 can be positioned to fluidly couple the second chamber 111 with a distal portion of the biological sterilization indicator 100 (i.e., a portion of the first chamber 109 that is located further from the second chamber 111, e.g., at a third level $L_3$, described below, and/or the fourth level $L_4$). As a result, the position at which the second fluid path 162 enters the first chamber 109 can be positioned further from the second chamber 111 than the position at which the first fluid path 160 enters the second chamber 111.

More specifically and by way of example only, with reference to FIGS. 4 and 6, in some embodiments, fluid can enter the second chamber 111 at a variety of locations, such as at the first level, height, or position (e.g., longitudinal position) $L_1$ located generally at the front of the insert 130, the substrate 119, the housing 102, and/or the second chamber 111, as well as at the second level, height, or position (e.g., longitudinal position) $L_2$ located approximately at the level of the aperture 121 in the substrate 119. As described above, it should be understood that the variety of opening and spaces between the first chamber 109 and the second chamber 111 that allow fluid to move into the second chamber 111 can collectively be referred to as the first fluid path 160. As further illustrated in FIG. 4, in some embodiments, gas (e.g., displaced gas) can exit the second chamber 111 via the second fluid path 162 (i.e., as fluid moves into the second chamber 111 via the first fluid path 160) at the third level, height, or position (e.g., longitudinal position) $L_3$ located generally at the back of the insert 130, the substrate 119, the housing 102, and/or the second chamber 111.

In the vertically upright orientation of the biological sterilization indicator 100 shown in FIGS. 4 and 6, the third level $L_3$ is located at or above both the first level $L_1$ and the second level $L_2$. In addition, in some embodiments, the third level $L_3$ can still be located at or above both the first level $L_1$ and the second level $L_2$ in operation of the biological sterilization indicator 100 (e.g., when seated in a well of a reading apparatus, during sterilization, and/or during activation). That is, in some embodiments, the biological sterilization indicator 100 can be tilted in operation (e.g., toward the left-hand side of FIG. 4 or 6, toward the right-hand side of FIG. 4 or 6, into the page of FIG. 4 or 6, and/or out of the page of FIG. 4 or 6).

The first, second, and third levels $L_1$, $L_2$, and $L_3$ are shown by way of example only; however, it should be understood that the exact location at which the first fluid path 160 enters the second chamber 111 and/or the exact location at which the second fluid path 162 exits the second chamber 111 can be different than what is illustrated in FIGS. 4 and 6.

As shown in FIGS. 4 and 6, the second fluid path 162 is at least partially defined by the channel 169 of the insert 130 and/or the channel 163 of the housing 102, which will generally be referred to as simply "the channel" in the following discussion, which can be interpreted to refer to at least a portion of the channel 163 and/or the channel 169 of the illustrated embodiment. In the illustrated embodiment, the channel has an entrance that can be described as being located at any point in the second chamber 111, or at the third level $L_3$, and an exit that is positioned generally at the fourth level, height, or position (e.g., longitudinal position) $L_4$. As shown in FIGS. 4 and 6, the exit position of the channel (i.e., the fourth level $L_4$) is generally located above the position at which the first fluid path 160 connects with the second chamber 111 (i.e., the first level $L_1$ and/or the second level $L_2$), for example, in operation of the biological sterilization indicator 100.

Said another way, the first fluid path 160 can be positioned to fluidly couple the second (lower) end 113 of the first chamber 109 to the first (upper) end 124 of the second chamber 111. The second fluid path 162, on the other hand, can be positioned to fluidly couple the second chamber 111 (e.g., the first (upper) end 124 of the second chamber 111) to an upper portion (e.g., the first (upper) end 112) of the first chamber 109.

Furthermore, in some embodiments, the position or level at which the second fluid path 162 (or the channel) connects with the second chamber 111 can be described as being located at portion of the second chamber 111 that is the last to fill with the liquid 122 when the container 120 is in its second, fractured, state.

In some embodiments, when the container 120 is in the second, fractured, state, and the second chamber 111 is at least partially filled with the liquid 122, the liquid 122 can have a level, height or position (e.g., longitudinal position) L, and the second fluid path 162 can extend between a position below the level L and a position above the level L. As a result, as the second chamber 111 fills with the liquid 122 when the container is in the second state, the second chamber 111 can continually be vented by the second fluid path 162.

In some embodiments, the first fluid path 160 can function as the main or primary fluid communication path between the first chamber 109 and the second chamber 111, and the second fluid path 162 can serve as an accessory or secondary fluid communication path between the second chamber 111 and the first chamber 109 (e.g., when the second fluid path 162 exits in the first chamber 109 and not another portion of the biological sterilization indicator 100). In such embodiments, the collective space, volume and/or area of the second fluid path 162 can be substantially less than that of the first fluid path 160. In some embodiments, at least a portion of the first fluid path 160 and the second fluid path 162 can be described as being substantially isolated from one another or as being substantially parallel and non-intersecting. In some embodiments, the first fluid path 160 and the second fluid path 162 can each extend substantially longitudinally (e.g., substantially parallel to the longitudinal direction $D_L$) between the first chamber 109 and the second chamber 111.

That is, generally, the biological sterilization indicator 100 that includes (1) a first fluid path, such as the first fluid path 160, configured to accommodate at least a majority of the fluid movement from the first chamber 109 to the second chamber 111, and (2) a second fluid path, such as the second fluid path 162, configured to vent gas from the second chamber 111 would have advantages over a biological sterilization indicator 100 that included either only one internal chamber, or only one fluid path connecting the first chamber 109 and the second chamber 111, such that gas would have to exit the second chamber 111 via the same fluid path that fluid enters the second chamber 111.

By configuring the first fluid path 160 and the second fluid path 162 as shown in the illustrated embodiment, in some embodiments, the biological sterilization indicator 100 can at least partially eliminate any air-lock effect that may occur as a result of trying to move a sterilant and/or the liquid 122 into the second chamber 111. In addition, in some embodiments, the second fluid path 162 can allow for the biological sterilization indicator 100 to be activated, and the liquid 122 to be moved into the second chamber 111 due to gravity, while the biological sterilization indicator 100 remains in the same orientation (e.g., a substantially vertically upright orientation, as shown in FIGS. 1-2, 4 and 6), without requiring that the biological sterilization indicator 100 to be tipped upside down, or otherwise re-oriented in order to move the liquid 122 into the second chamber 111.

With continued reference to the insert 130, the projections 158 of the insert 130 are illustrated as being relatively rigid and stationary. That is, in some embodiments, the projections 158 may not be adapted to substantially flex, distort, deform or otherwise heed to the container 120 as it is moved in the housing 102. Rather, in some embodiments, as shown in FIGS. 1-4 and 6, the projections 158 can each be configured to have an upper end 159 atop which the container 120 can be positioned and held intact before activation. As shown in FIGS. 1-2 and 4, in some embodiments, the projections 158 can be positioned to fracture the container 120 at its radiused end, for example, when an oblong or capsule-shaped container 120 is employed.

One potential advantage of having the projections 158 form at least a portion of the carrier 132 is that the bottom of the container 120 can be unrestricted when the container 120 is fractured, such that the liquid 122 can be released from the container 120 and moved toward the spores 115 with relative ease and reliability.

In such embodiments, the insert 130 can be used to fracture the container 120 in a direction that is substantially perpendicular to a flat side of the container 120, for example, when an oblong or capsule-shaped container 120 is employed. In such embodiments, fracturing the container 120 along its side can be achieved, along with maintaining some open spaces around the lower end of the container 120 to facilitate moving the liquid 122 from the container 120 to the proximity of the spores 115 when the container 120 is fractured.

As mentioned above, the projections 158 can be adapted to fracture the container 120 as the container 120 is moved with respect to the housing 102 (e.g., along the longitudinal direction $D_L$), for example, in response to the second portion 106 of the housing 102 being moved with respect to the first portion 104 of the housing 102 (e.g., from the first position 148 to the second position 150).

In some embodiments, the projections 158 can include one or more edges (e.g., tapered edges) or points or otherwise be configured to concentrate the crushing force to increase the pressure on the container 120 in the regions adjacent the projections 158, and to facilitate fracturing the container 120 more easily and in one or more desired regions. In some embodiments, such concentration of force can reduce the total effort or force needed to move the second portion 106 with respect to the first portion 104 and to fracture the container 120 (or a portion thereof).

As shown in FIGS. 1-4 and 6, the projections 158 are integrally formed with the base 127 of the insert 130; however, it should be understood that the projections 158 can instead be integrally formed with the wall 108 of the housing 102. In addition, in some embodiments, the projections 158 can be coupled to the housing 102, or the projections 158 and the base 127 can be provided by separate inserts. In such embodiments, the projections 158 can each be a separate insert, or multiple projections 158 can be provided by one or more inserts. In addition, the insert 130 can be configured to abut the wall 118 to inhibit movement of the first portion the insert 130 into the proximity of the spores 115 (e.g., the lower portion 114 of the housing 102).

In addition, in some embodiments, as shown in FIGS. 1-4 and 6, the projections 158 can extend a distance along the longitudinal direction $D_L$, and the length and/or thickness (e.g., which can vary along the length) of the projections 158 can be tailored to control the fracturing of the container 120 at a desired position in the housing 102 and in a desired manner. The configuration of the projections 158 is shown in FIGS. 1-7 by way of example only.

In general, each of the projections 158 is shown by way of example only as increasing in thickness (e.g., inwardly toward the container 120 or center of the housing 102) along the longitudinal direction $D_L$ toward the spores 115. Such a configuration can decrease the cross-sectional area that is available to the container 120, as the container 120 is moved toward the spores 115, for example, in response to the second portion 106 being moved to the second position 150.

Furthermore, the biological sterilization indicator 100 is shown in FIGS. 1-7 as including two projections 158 and a sidewall 131 by way of example only, but it should understood that one projection 158 or as many as structurally possible, and other configurations, can be employed. In addition, the projections 158 can be shaped and dimensioned as desired, depending on the shape and dimensions of the housing 102, on the shape and dimensions of the container 120, on the shape and dimensions of the insert 130, and/or on the manner and position desired for fracturing the container 120.

As mentioned above, in some embodiments, at least a portion of the housing 102 can be tapered (see, e.g., the tapered portion 146 in FIG. 3). As a result, the cross-sectional area in the housing 102 can generally decrease along the longitudinal direction $D_L$. However, it should be understood that the inner dimensions of the housing 102 can generally decrease in the tapered portion along the longitudinal direction $D_1$ without the outer dimensions of the housing 102 changing. In some embodiments, the outer dimensions of the housing 102 can be uniform along its length, even though the inner portion of the housing 102 tapers along its length. In some embodiments, the one or more projections 158 alone can vary in thickness (i.e., toward the container 120, e.g., in a radial direction) along the longitudinal direction $D_L$, such that the cross-sectional area available to the container 120 generally decreases as the container 120 is moved in the housing 102 during activation, even though the dimensions of the housing 102 do not change (e.g., even if the housing 102 does not include any tapered portion 146, either internally or externally).

As shown in FIGS. 1-7, the upper end 159 of each of the projections 158 includes a rounded, curved or arcuate surface, which can facilitate movement of the container 120 from the first position 148 in which the container 120 sits at least partially above the upper end 159 of the projection 158 to a position in which the container 120 is forced, at least partially, into the smaller cross-sectional area region in between the projections 158 (or between the wall 108 of the housing 102 and one or more projections 158). In addition, the rounded upper end 159 can inhibit premature breakage of the container 120, which can inhibit premature activation of the biological sterilization indicator 100 (i.e., premature release of the liquid 122).

In some embodiments, as shown in FIG. 3, the insert 130 can be sized and shaped to allow the container 120 to be held above the projections 158 and out from the region adjacent any portion of an inwardly-facing surface of one or more of the projections 158 to inhibit accidental or premature activation of the biological sterilization indicator 100. Such a configuration can also inhibit inadvertent breakage due to shock or material expansion (e.g., due to exposure to heat during a sterilization process).

The carrier 132, which can be formed at least partially by the upper ends 159 of the projections 158, can be configured to hold a bottom portion of the container 120, and the projections 158 can be positioned to fracture the container 120 at a location near the bottom of the container 120 as it is positioned in the housing 102. Such a configuration can allow the container 120 to be broken near its bottom and can facilitate removal of the liquid 122 from the container 120, which can enhance the availability of the liquid 122 to the spores 115, and can enhance the reliability of releasing the liquid 122 into fluid communication with the spores 115 (e.g., with the spore reservoir 136). Such a configuration is shown by way of example only, however, and it should be understood that the projections 158 can be configured and positioned to fracture the container 120 in any desired manner.

Some embodiments of the present disclosure provide optimal and safe breakage of a frangible container 120 with relatively low force, while enhancing transfer of liquid 122 to the spore region (e.g., the second chamber 111 of the housing 102) of the biological sterilization indicator 100, and/or enhancing containment of the liquid 122 in the spore region of the biological sterilization indicator 100. In addition, some embodiments of the present disclosure operate to drive a liquid to a particular area of the biological sterilization indicator 100, such as a detection chamber (e.g., the second chamber 111) of the biological sterilization indicator 100.

In the embodiment illustrated in FIGS. 1-7, the insert 130 is illustrated as including two projections 158 that are approximately equally spaced about the container 120 and/or about the sidewall 131. However, in some embodiments, the sidewall 131 can include one solid (e.g., substantially annular or semi-annular) projection 158 that extends radially inwardly from the sidewall 131. Furthermore, in some embodiments, the sidewall 131 can extend further around the inner surface of the housing 102 than what is illustrated. However, employing one or more narrower (e.g., in an angular dimension) projections 158, such as those shown in FIGS. 1-7, can provide a substantially constant or substantially unobstructed sterilant path 164 around the container 120.

Whether the insert 130 includes one or more projections 158 or sidewalls 131, the insert 130 can be configured to hold the container 120 in the housing 102 in a consistent location to provide a substantially constant sterilant path 164 during sterilization. For example, rather than allowing the container 120 to move or roll around (e.g., radially and/or longitudinally) in the housing 102 before activation (e.g., during sterilization), the insert 130 can hold the container 120 in a substantially consistent position, which can allow a sterilant a substantially consistent and relatively unobstructed path between an outer surface of the container 120 and an inner surface of the housing 102, with little or no opportunity for inadvertent blockage.

As shown in the illustrated embodiment, the insert 130 can further include one or more projections 161 positioned substantially horizontally or perpendicularly with respect to the longitudinal direction $D_L$ of a biological sterilization indicator (e.g., when the insert 130 is positioned in a biological sterilization indicator). The projections 161 can be referred to as "second projections" or "horizontal projections," while the projections 158 used to hold and/or break the container 120 can be referred to as "first projections" or "vertical projections." The second projections 161 are not angled downwardly like the base 127. As a result, the second projections 161 can be used for a variety of purposes. For example, the second projections 161 can stabilize the insert 130 (e.g., aid in holding the insert 130 in a desired position in the housing 102 of the biological sterilization indicator 100) under the force of fracturing the container 120. In addition, the second projections 161 can function to retain and/or collect fractured portions of the container 120 after it has been fractured to inhibit movement of such portions into the proximity of spores in the biological sterilization indicator, which could negatively affect spore growth and/or detection of spore growth. Other shapes and configurations of the second projections 161 can be employed that still allow for fluid movement down to the spores 115 while inhibiting solid movement down to the spores 115.

In some embodiments, the insert 130 (e.g., the base 127) can be adapted for one or more of facilitating or allowing fluid movement (e.g., movement of the liquid 122) into the second chamber 111 (i.e., the lower portion 114) of the housing 102; minimizing movement of fractions or portions (e.g., solids) of the fractured container 120 into the second chamber 111 of the housing 102, that is, collecting and/or retaining portions of the fractured container 120; and/or minimizing diffusion of the spores 115 and/or signals out of the second chamber 111 of the housing 102. For example, in some embodiments, the base 127 can be configured to function as a grate or filter. In some embodiments, spore growth is determined by fluorescent indicators/molecules (e.g., fluorophores) or other markers. In some embodiments, if the liquid level after activation in the biological sterilization indicator 100 is above the location of the spores 115, such molecules or markers, or the spores 115 themselves, can move or diffuse away from or out of the spore reservoir 136 and, potentially, out of the second chamber 111 of the housing 102. As a result, portions of the biological sterilization indicator 100 (e.g., the insert 130) can be configured to inhibit undesirable diffusion of various indicators, molecules, and/or markers out of the second chamber 111 of the biological sterilization indicator 100. In some embodiments, as described above, the substrate 119 can also inhibit such undesirable diffusion.

In the embodiment illustrated in FIGS. 1-4, the base 127 of the insert 130 is generally U-shaped or horseshoe-shaped and includes a central aperture 177 (see FIG. 2) that facilitates the movement of sterilant toward the spores 115 during sterilization and the movement of the liquid 122 toward the spores 115 during activation. The horseshoe shape of the base 127 can increase the opening between the upper portion 116 (i.e., the first chamber 109) and the lower portion 114 (i.e., the second chamber 111) of the housing 102; however, this shape is shown by way of example only, and other shapes can be employed.

In some embodiments, the insert 130 can be described as including one or more downwardly-extending projections 127 adapted to abut or otherwise couple to the wall 118 or another internal structure of the biological sterilization indicator 100 to provide a base or support for the insert 130, to inhibit movement of the insert 130 and container 120 relative to the housing 102 before activation, and/or to provide resistance or force to aid in breaking the container 120 during activation. As a result, in some embodiments, the base 127 can instead be referred to as "third projections" 127.

As shown in the illustrated embodiment, in some embodiments, the insert 130 can be configured to reside entirely in the first chamber 109 of the biological sterilization indicator 100, such that the insert 130 does not extend into the second chamber 111 where it could potentially interfere with interrogation or detection processes. Furthermore, the insert 130 can be configured to inhibit movement of other portions of the biological sterilization indicator 100 (e.g., the fractured container 120) into the second chamber 111.

The insert 130 of the illustrated embodiment is generally symmetrical about a central longitudinal line of symmetry, such that there are two identical first projections 158, two identical second projections 161, and two identical third projections 127. However, the insert 130 need not include any lines of symmetry, and the first projections 158 need not be the same as one another, the second projections 161 need not be the same as one another, and the third projections 127 need not be the same as one another. The insert 130, and the various projections 158, 161 and 127 can be sized and positioned to control the sterilant path 164, for example, to tailor the kill/survival rate of the biological sterilization indicator 100, to inhibit inadvertent fracture of the container 120, to facilitate movement of the container 120 in the housing 120, to mate with or engage the housing 102, and/or to control the breakage of the container 120.

By way of example only, the illustrated insert 130 is shown as being a unitary device that includes at least the following: means for holding the container 120 before activation, for fracturing the container 120 during activation; for allowing movement of the container 120 in the housing 102; for providing a substantially constant sterilant path 164, for collecting and/or retaining portions of the fractured container 120 after activation (or at least partially inhibiting movement of portions of the fractured container 120 into the second chamber 111 of the housing 102); and/or for minimizing diffusion of the spores 115 and/or signals from the second chamber 111 to the first chamber 109 of the housing 102 after activation. However, it should be understood that in some embodiments, the insert 130 can include multiple portions that may not be part of a single, unitary device, and each of the portions can be adapted to do one or more of the above functions.

The insert 130 is referred to as an "insert" because in the illustrated embodiment, the device that performs the above functions is a device that can be inserted into the reservoir 103 (and, particularly, the first chamber 109) of the housing 102. However, it should be understood that the insert 130 can instead be provided by the housing 102 itself or another component of the biological sterilization indicator 100 and need not necessarily be insertable into the housing 102. The term "insert" will be described throughout the present disclosure for simplicity, but it should be understood that such a term is not intended to be limiting, and it should be appreciated that other equivalent structures that perform one or more of the above functions can be used instead of, or in combination with, the insertable insert 130. Furthermore, in the illustrated embodiment, the insert 130 is both insertable into and removable from the housing 102, and particularly, into and out of the first portion 104 (and the first chamber 109) of the housing 102. However, it should be understood that even if the insert 130 is insertable into the housing 102, the insert 130 need not be removable from the housing 102, but rather can be fixedly coupled to the housing 102 in a manner that inhibits removal of the insert 130 from the housing 102 after positioning the insert 130 in a desired location.

In some embodiments, at least a portion of the housing 102, for example, the lower portion 114 of the housing 102, can be transparent to an electromagnetic radiation wavelength or range of wavelengths (e.g., transparent to visible light when visible-light optical detection methods are employed), which can facilitate detection of spore growth. That is, in some embodiments, as shown in FIGS. 3, 4 and 6, at least a portion of the housing 102 can include or form a detection window 167.

In addition, in some embodiments, as shown in FIG. 3, at least a portion of the housing 102, for example, the lower portion 114 can include one or more planar walls 168. Such planar walls 168 can facilitate detection (e.g., optical detection) of spore growth. In addition, as shown and described above, the wall 108 of the first portion 104 of the housing 102 can include one or more stepped or tapered regions, such as the step 152, the step 123, and a tapered wall, or step, 170. The tapered wall 170 can function to reduce the overall thickness and size of the lower portion, or detection portion, 114 of the housing 102, such that the outer dimensions of the housing 102 are reduced in addition to the inner dimensions. Such a reduction in size and/or thickness of the lower portion 114 of the biological sterilization indicator 100 can facilitate detection. In addition, having one or more features, such as the steps and/or tapered walls 123, 152, 170 can allow the biological sterilization indicator 100 to be coupled to a reader or detection device in only one orientation, such that the biological sterilization indicator 100 is "keyed" with respect to a reading apparatus, which can minimize user error and enhance reliability of a detection process. In some embodiments, one or more portions of the biological sterilization indicator 100 can be keyed with respect to a reading apparatus.

The biological sterilization indicator of the present disclosure generally keeps the liquid 122 and the spores 115 separate but in relatively close proximity (e.g., within the self-contained biological sterilization indicator 100) during sterilization, such that the liquid 122 and the spores 115 can be readily combined after exposure to a sterilization process. The liquid 122 and the spores 115 can be incubated during a detection process (e.g., the reading apparatus 12 can incubate the biological sterilization indicator 100), or the biological sterilization indicator 100 can be incubated prior to a detection process. In some embodiments, when incubating the spores with the liquid 122, an incubation temperature above room temperature can be used. For example, in some embodiments, the incubation temperature is at least about 37° C., in some embodiments, the incubation temperature is at least about 50° C. (e.g., 56° C.), and in some embodiments, at least about 60° C. In some embodiments, the incubation temperature is no greater than about 60° C., in some embodiments, no greater than about 50° C., and in some embodiments, no greater than about 40° C.

A detection process can be adapted to detect a detectable change from the spores 115 (e.g., from within the spore reservoir 136) or the liquid 122 surrounding the spores 115. That is, a detection process can be adapted to detect a variety of characteristics, including, but not limited to, electromagnetic radiation (e.g., in the ultraviolet, visible, and/or infrared bands), fluorescence, luminescence, light scattering, electronic properties (e.g., conductance, impedance, or the like, or combinations thereof), turbidity, absorption, Raman spectroscopy, ellipsometry, or the like, or a combination thereof. Detection of such characteristics can be carried out by one or more of a fluorimeter, a spectrophotometer, colorimeter, or the like, or combinations thereof. In some embodiments, such as embodiments that measure fluorescence, visible light, etc., the detectable change is measured by detecting at a particular wavelength.

The spores and/or the liquid 122 can be adapted (e.g., labeled) to produce one or more of the above characteristics as a result of a biochemical reaction that is a sign of spore viability. As a result, no detectable change (e.g., as compared to a baseline or background reading) can signify an effective sterilization process, whereas a detectable change can signify an ineffective sterilization process. In some embodiments, the detectable change can include a rate at which one or more of the above characteristics is changing (e.g., increasing fluorescence, decreasing turbidity, etc.).

In some embodiments, spore viability can be determined by exploiting enzyme activity. As described in U.S. Pat. No. 5,073,488 (Matner et al.), which is incorporated herein by reference, enzymes can be identified for a particular type of spore in which the enzyme has particularly useful characteristics that can be exploited to determine the efficacy of a sterilization process. Such characteristics can include the following: (1) the enzyme, when subjected to sterilization conditions which would be sufficient to decrease a population of $1\times10^6$ test microorganisms by about 6 logs (i.e., to a population of about zero as measured by lack of outgrowth of the test microorganisms), has a residual activity which is equal to "background" as measured by reaction with a substrate system for the enzyme; and (2) the enzyme, when subjected to sterilization conditions sufficient only to decrease the population of $1\times10^6$ test microorganisms by at least 1 log, but less than 6 logs, has enzyme activity greater than "background" as measured by reaction with the enzyme substrate system. The enzyme substrate system can include a substance, or mixture of substances, which is acted upon by the enzyme to produce a detectable enzyme-modified product, as evident by a detectable change.

In some embodiments, the biological sterilization indicator 100 can be assayed in a single-side mode, where the biological sterilization indicator 100 includes only one detection window (e.g., detection window 167 of FIG. 3) that is positioned, for example, near the spores 115. In some embodiments, however, the biological sterilization indicator 100 can include more than one detection window (e.g., a window formed by all or a portion of both parallel walls 168 of the lower portion 114 of the housing 102), such that the biological sterilization indicator 100 can be assayed via more than one detection window. In embodiments employing multiple detection windows, the detection windows can be positioned side-by-side (similar to a single-side mode), or the detection windows can be oriented at an angle (e.g., 90 degrees, 180 degrees, etc.) with respect to one another.

In general, the spores 115 are positioned within the spore reservoir 136 which is in fluid communication with the reservoir 103. In some embodiments, the spore reservoir 136 forms a portion of the reservoir 103 (e.g., a portion of the second chamber 111). As shown in FIG. 4, the reservoir 103 is in fluid communication with ambience (e.g., via the aperture 107) during sterilization to allow sterilant to enter the reservoir 103 during a sterilization process to sterilize the spores 115. The container 120 can be configured to contain the liquid 122 during sterilization to inhibit the liquid 122 from being in fluid communication with the spores 115, the reservoir 103, and the sterilant during sterilization.

Various details of the spores 115 and/or spore reservoir 136 will now be described in greater detail.

In some embodiments, the spores 115 can be positioned directly in the lower portion 114 of the housing 102, or the spores 115 can be positioned in a spore reservoir, such as the spore reservoir 136 (e.g., provided by the spore carrier 135). Whether the spores 115 are positioned directly in the lower portion 114 of the housing 102 or in a spore reservoir, the spores 115 can be provided in a variety of ways. In some embodiments, the spores 115 can be in a spore suspension that can be positioned in a desired location in the biological sterilization indicator 100 and dried down. In some embodiments, the spores 115 can be provided on a substrate (not shown) that can be positioned and/or secured in a desired location in the biological sterilization indicator 100. Some embodiments can include a combination of spores 115 provided in a dried down form and spores 115 provided on a substrate.

In some embodiments, the substrate can be positioned to support the spores 115 and/or to help maintain the spores 115 in a desired locus. Such a substrate can include a variety of materials, including, but not limited to, paper, a polymer (e.g., any of the polymers listed above with respect to the housing 102), an adhesive (e.g., acrylate, natural or synthetic rubber, silicone, silicone polyurea, isocyanate, epoxy, or combinations thereof), a woven cloth, a nonwoven cloth, a microporous material (e.g., a microporous polymeric material), a reflective material (e.g., a metal foil), a glass, a porcelain, a ceramic, a gel-forming material (e.g., guar gum), or combinations thereof. In addition, or alternatively, such a substrate can include or be coupled to a hydrophilic coating to facilitate bringing the liquid 122 into intimate contact with the spores 115 (e.g., when the liquid 122 employed is aqueous). In addition, or alternatively, such a hydrophilic coating can be applied to any fluid path positioned to fluidly couple the liquid 122 and the spores 115. In some embodiments, in addition to, or in lieu of a hydrophilic coating, a hydrophobic coating can be applied to other portions of the housing 102 (e.g., the lower portion 114 of the housing 102) and/or spore reservoir 136, such that the liquid 122 is preferentially moved into contact with the spores 115.

Some embodiments of the biological sterilization indicator 100 do not include the spore carrier 135. Rather, the spore reservoir 136 is provided by the lower portion 114 of the housing 102 itself, and the spores 115 can be positioned in the lower portion 114, adsorbed to an inner surface or wall of the lower portion 114, or combinations thereof. In some embodiments, the spores 115 can be provided on a substrate that is positioned in the lower portion 114 of the housing 102.

In some embodiments, the spores 115 can be positioned in one locus of spores or in a plurality of loci of spores, all of which can be positioned either in the reservoir 103, in the lower portion 114 of the housing 102, and/or in the spore reservoir 136. In some embodiments, having multiple loci of spores can maximize the exposure of the spores to sterilant and to the liquid 122, can improve manufacturing (e.g., placement of the spores can be facilitated by placing each locus of spores in a depression within the biological sterilization indicator 100), and can improve detection characteristics (e.g., because spores in the middle of one large locus of spores may not be as easily detected). In embodiments employing a plurality of loci of spores, each locus of spores can include a different, known number of spores, and/or each locus of spores can include different spores, such that a plurality of spore types can be tested. By employing multiple types of spores, the biological sterilization indicator 100 can be used for a variety of sterilization processes and a specific locus of spores can be analyzed for a specific sterilization process, or the multiple types of spores can be used to further test the effectiveness, or confidence, of a sterilization process.

In addition, in some embodiments, the biological sterilization indicator 100 can include a plurality of spore reservoirs 136, and each spore reservoir 136 can include one or more loci of spores 115. In some embodiments employing a plurality of spore reservoirs 136, the plurality of spore reservoirs 136 can be positioned in fluid communication with the reservoir 103.

In some embodiments, the spores 115 can be covered with a cover (not shown) adapted to fit in or over the spores 115 and/or the spore reservoir 136. Such a cover can help maintain the spores within the desired region of the biological sterilization indicator 100 during manufacturing, sterilization and/or use. The cover, if employed, can be formed of a material that does not substantially impede a detection process, and/or which is at least partially transmissive to electromagnetic radiation wavelengths of interest. In addition, depending on the material makeup of the cover, in some embodiments, the cover can facilitate wicking the liquid 122 (e.g., the nutrient medium) along the spores 115. In some embodiments, the cover can also contain features for facilitating fluid flow into the spore reservoir 136 (or to the spores 115), such as capillary channels, hydrophilic microporous fibers or membranes, or the like, or a combination thereof. In addition, in some embodiments, the cover can isolate a signal, or enhance the signal, which can facilitate detection. Such a cover can be employed whether the spores 115 are positioned within the spore reservoir 136 or directly in the lower portion 114 of the housing 102. In addition, such a cover can be employed in embodiments employing a plurality of loci of spores. The cover can include a variety of materials, including, but not limited to, paper, a polymer (e.g., any of the polymers listed above with respect to the housing 102), an adhesive (e.g., acrylate, natural or synthetic rubber, silicone, silicone polyurea, isocyanate, or epoxy polymeric material), a glass, a porcelain, a ceramic, a gel-forming material (e.g., guar gum), or combinations thereof.

In some embodiments, the biological sterilization indicator 100 can further include a modified inner surface, such as a reflective surface, a white surface, a black surface, or another surface modification suitable to optimize the optical properties of the surface. A reflective surface (e.g., provided by a metal foil) can be positioned to reflect a signal sent into the spore reservoir 136 from an assaying or detection device and/or to reflect any signal generated within the spore reservoir 136 back toward the assaying device. As a result, the reflective surface can function to improve (e.g., improve the intensity of) a signal from the biological sterilization indicator 100. Such a reflective surface can be provided by an inner surface of the housing 102; a material coupled to the inner surface of the housing 102; an inner surface the spore reservoir 136; a material coupled to the inner surface of the spore reservoir 136; or the like; or the reflective surface can form a portion of or be coupled to a spore substrate; or a combination thereof.

Similarly, in some embodiments, the biological sterilization indicator 100 can further include a white and/or black surface positioned to increase and/or decrease a particular signal sent into the spore reservoir 136 from an assaying device and/or to increase and/or decrease a particular signal generated within the spore reservoir 136. By way of example only, a white surface can be used to enhance a signal, and a black surface can be used to reduce a signal (e.g., noise).

In some embodiments, the spores 115 can be positioned on a functionalized surface to promote the immobilization of the spores 115 on the desired surface. For example, such a functionalized surface can be provided by an inner surface of the housing 102, an inner surface of the spore reservoir 136, can form a portion of or be coupled to a spore substrate, or the like, or a combination thereof.

In some embodiments, the spores 115 are positioned (e.g. applied by coating or another application method) on a microstructured or microreplicated surface (e.g., such microstructured surfaces as those disclosed in PCT Publ. No. WO 2007/070310 (Halverson et al.), U. S. Publ. No. US 2003/0235677 (Hanschen et al.), and PCT Publ. No. WO 2004/000569 (Graham et al.). For example, such a microstructured surface can be provided by an inner surface of the housing 102, can be provided by an inner surface of the spore reservoir 136, can form a portion of or be coupled to a spore substrate, or the like, or a combination thereof.

In some embodiments, the biological sterilization indicator 100 can further include a gel-forming material positioned to be combined with the spores 115 and the liquid 122 when the liquid 122 is released from the container 120. For example, the gel-forming material can be positioned near the spores 115 (e.g., in the spore reservoir 136), in the lower portion 114 of the housing 102, can form a portion of or be coupled to a spore substrate, or the like, or a combination thereof. Such a gel-forming material can form a gel (e.g., a hydrogel) or a matrix comprising the spores and nutrients when the liquid 122 comes into contact with the spores. A gel-forming material (e.g., guar gum) can be particularly useful because it has the ability to form a gel upon hydration, it can aid in localizing a signal (e.g., fluorescence), it can anchor the spores 115 in place, it can help minimize diffusion of the spores 115 and/or a signal from the spore reservoir 136, and/or it can enhance detection.

In some embodiments, the biological sterilization indicator 100 can further include an absorbent or a wicking material. For example, the wicking material can be positioned near the spores 115 (e.g., in the spore reservoir 136), can form at least a portion of or be coupled to a spore substrate, or the like, or a combination thereof. Such a wicking material can include a porous wicking pad, a soaking pad, or the like, or a combination thereof, to facilitate bringing the liquid 122 into intimate contact with the spores.

In some embodiments, the frangible container 120 can be configured to facilitate fracturing of the frangible container 120 in a desired manner. For example, in some embodiments, a lower portion of the frangible container 120 can be formed of a thinner and/or weaker material, such that the lower portion preferentially fractures over another portion of the frangible container 120. In addition, in some embodiments, the frangible container 120 can include a variety of features positioned to facilitate fracturing of the frangible container 120 in a desired manner, including, but not limited to, a thin and/or weakened area, a score line, a perforation, or the like, or combinations thereof.

The frangible container 120 can have a first closed state in which the liquid 122 is contained within the frangible container 120 and a second open state in which the frangible container 120 has fractured and the liquid 122 is released into the reservoir 103 and/or the spore reservoir 136, and in fluid communication with the spores 115.

In some embodiments, the biological sterilization indicator 100 can be activated (e.g., the second portion 106 can be moved to the second position 150) manually. In some embodiments, the biological sterilization indicator 100 can be activated by a reading apparatus (e.g., as the biological sterilization indicator 100 is positioned in the reading apparatus). In some embodiments, the biological sterilization indicator 100 can be activated with a device (e.g., an activation device) independent of such a reading apparatus, for example, by positioning the biological sterilization indicator 100 in the device prior to positioning the biological sterilization indicator 100 in a well of a reading apparatus. In some embodiments, the biological sterilization indicator 100 can be activated by a combination of two or more of the reading apparatus, a device independent of the reading apparatus, and manual activation.

One or both of the biological sterilization indicator 100 and another device, such as a reading apparatus can be further configured to inhibit premature or accidental fracturing of the frangible container 120. For example, in some embodiments, the biological sterilization indicator 100, activation device, or reading apparatus can include a lock or locking mechanism that is positioned to inhibit the second portion 106 of the housing 102 from moving into the second position 150 until desired. In such embodiments, the biological sterilization indicator 100 cannot be activated until the lock is moved, removed or unlocked. In addition, or alternatively, in some embodiments, the biological sterilization indicator 100, activation device, and/or reading apparatus can include a lock or locking mechanism that is positioned to inhibit the second portion 106 of the housing 102 from moving from the second position 150 back into the first position 148 after activation.

In some embodiments, as shown in the illustrated embodiment, at least a portion of the housing can be flat (e.g., the parallel walls 168), and can be substantially planar with respect to the spore reservoir 136, and one or both of the parallel walls 168 or a portion thereof (e.g., the detection window 167) can be sized such that at least one dimension of the wall 168 (or detection window 167) substantially matches at least one dimension of the spore reservoir 136 and/or the locus of spores 115. Said another way, the wall 168 or a portion thereof (e.g., the detection window 167) can include a cross-sectional area that is substantially the same size as the cross-sectional area of the spore reservoir 136 and/or the locus of spores 115. Such size matching between the wall 168/detection window 167 and the spore reservoir 136 and/or the locus of spores 115 can maximize the signal detected during a detection or assaying process. Alternatively, or in addition, the wall 168 or detection window 167 can be sized to match the reservoir 103 (e.g., at least one dimension or the cross-sectional areas can be sized to match). Such size matching between detection zones can improve spore assaying and detection.

The biological sterilization indicator 100 illustrated in FIGS. 1-7, at least the portion of the biological sterilization indicator 100 where the spores 115 are positioned, is relatively thin (i.e., the "z dimension" is minimized), such that an optical path from the spores to the wall 168 (or detection window 167) is minimized and/or any effect of interfering substances in the liquid 122 (or nutrient medium) is minimized.

In use, the biological sterilization indicator 100 can be placed along with a sterilizing batch for a sterilization process. During sterilization, a sterilant is in fluid communication with the reservoir 103 (i.e., the first chamber 109 and the second chamber 111), the spore reservoir 136, and the spores 115 primarily via the sterilant path 164, such that sterilant can reach the spores to produce sterilized spores. As described above, the cooperation of the first fluid path 160 and the second fluid path 162 can facilitate movement of the sterilant into the second chamber 111, and particularly, into the closed end 105 of the biological sterilization indicator 100. In addition, during sterilization, the frangible container 120 is in a closed state, held intact at least partially by the carrier 132 of the insert 130. When the frangible container 120 is in a closed state, the liquid 122 is protected from the sterilant and is not in fluid communication with the reservoir 103 (particularly, the second reservoir 111 formed at least partially by the lower portion 114 of the housing 102), the spore reservoir 136, the spores 115, or the sterilant path 164.

Sterilization can further include moving a sterilant from the first chamber 109 to the second chamber 111 via the first fluid path 160 when the container 120 is in the first state, and moving displaced gas (e.g., trapped air) out of the second chamber 111 via the second fluid path 162 in response to, or to facilitate, moving the sterilant from the first chamber 109 to the second chamber 111.

Following sterilization, the effectiveness of the sterilization process can be determined using the biological sterilization indicator 100. The second portion 106 of the housing 102 can be unlocked, if previously locked in the first position 148, and moved from the first position 148 (see FIG. 3) to the second position 150 (see FIG. 4) to cause activation of the biological sterilization indicator 100. Such movement of the second portion 106 can cause the frangible container 120 to move in the housing 102, for example, along the longitudinal direction $D_L$ from a position above the upper ends 159 of the projections 158 to a position within the interior of the projections 158, which can cause the frangible container 120 to fracture. Fracturing the frangible container 120 can change the frangible container 120 from its closed state to its open state and release the liquid 122 into the reservoir 103, and into fluid communication with the spore reservoir 136 and the spores 115. The liquid 122 can either include nutrient medium (e.g., germination medium) for the spores, or the liquid 122 can contact nutrient medium in a dry form (e.g., in a powdered or tablet form) to form nutrient medium, such that a mixture including the sterilized spores and nutrient medium is formed. The mixture can then be incubated prior to or during a detection or assaying process, and the biological sterilization indicator 100 can be interrogated for signs of spore growth.

Activation can further include moving the liquid 122 from the first chamber 109 to the second chamber 111 via the first fluid path 160 when the container 120 is in the second state, and moving displaced gas (e.g., trapped air) out of the second chamber 111 via the second fluid path 162 in response to, or to facilitate, moving the liquid 122 from the first chamber 109 to the second chamber 111 via the first fluid path 160.

To detect a detectable change in the spores 115, the biological sterilization indicator 100 can be assayed immediately after the liquid 122 and the spores 115 have been combined to achieve a baseline reading. After that, any detectable change from the baseline reading can be detected. The biological sterilization indicator 100 can be monitored and measured continuously or intermittently. In some embodiments, a portion of, or the entire, incubating step may be carried out prior to measuring the detectable change. In some embodiments, incubation can be carried out at one temperature (e.g., at 37° C., at 50-60° C., etc.), and measuring of the detectable change can be carried out at a different temperature (e.g., at room temperature, 25° C., or at 37° C.).

The readout time of the biological sterilization indicator 100 (i.e., the time to determine the effectiveness of the sterilization process) can be, in some embodiments, less than 8 hours, in some embodiments, less than 1 hour, in some embodiments, less than 30 minutes, in some embodiments, less than 15 minutes, in some embodiments, less than 5 minutes, and in some embodiments, less than 1 minute.

Select Embodiments of the Present Disclosure

In a first embodiment, the present disclosure provides a fluorinated 4'-alkylumbelliferyl α-D-glucopyranoside represented by the structural formula

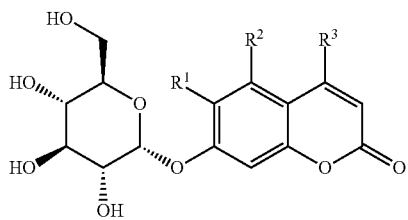

wherein:
one of $R^1$ and $R^2$ is F and the other is H, and
$R^3$ is an alkyl group having from 1 to 12 carbon atoms.

In a second embodiment, the present disclosure provides a fluorinated 4'-alkylumbelliferyl α-D-glucopyranoside according to the first embodiment, wherein $R^3$ is an alkyl group having 1 to 4 carbon atoms.

In a third embodiment, the present disclosure provides a fluorinated 4'-methylumbelliferyl α-D-glucopyranoside represented by the structural formula

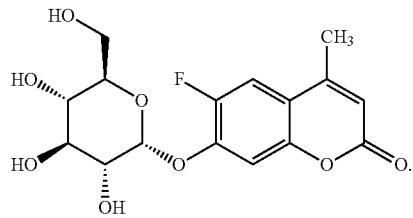 [SMILES: Cc1cc(=O)oc2cc(O[C@H]3O[C@H](CO)[C@@H](O)[C@H](O)[C@H]3O)c(F)cc12]

In a fourth embodiment, the present disclosure provides a fluorinated 4'-methylumbelliferyl α-D-glucopyranoside represented by the structural formula

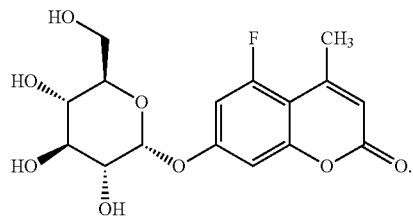 [SMILES: Cc1cc(=O)oc2cc(O[C@H]3O[C@H](CO)[C@@H](O)[C@H](O)[C@H]3O)cc(F)c12]

In a fifth embodiment, the present disclosure provides a self-contained biological sterilization indicator comprising:
a housing,
bacterial spores comprising, and/or capable of producing, an enzyme capable of catalyzing cleavage of an enzyme substrate represented by the structural formula

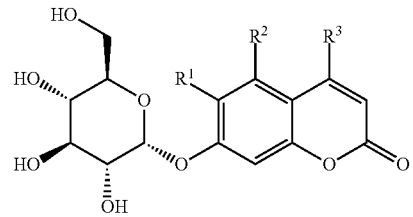

wherein:
one of $R^1$ and $R^2$ is F and the other is H, and
$R^3$ is an alkyl group having from 1 to 12 carbon atoms; and
a frangible container containing a composition, wherein the composition comprises the enzyme substrate, wherein if the frangible container is broken the composition will contact the bacterial spores to form a mixture having an initial pH in the range from 6.0 to 9.0.

In a sixth embodiment, the present disclosure provides a self-contained biological sterilization indicator according to the fifth embodiment, wherein the self-contained biological sterilization indicator is disposed inside a process-challenge device.

In a seventh embodiment, the present disclosure provides a self-contained biological sterilization indicator according to the fifth or sixth embodiment, wherein $R^3$ is an alkyl group having 1 to 4 carbon atoms.

In an eighth embodiment, the present disclosure provides a self-contained biological sterilization indicator according to any one of the fifth to seventh embodiments, wherein the self-contained biological sterilization indicator is capable of determining efficacy of two or more cycles chosen from the powerset of 121 gravity, 121 pre-vac, 121 SFPP, 132 gravity, 132 pre-vac, 132 SFPP, 134 pre-vac, 134 SFPP, 135 gravity, 135 pre-vac, and 135 SFPP.

In a ninth embodiment, the present disclosure provides a self-contained biological sterilization indicator according to any one of the fifth to eighth embodiments, wherein the enzyme substrate is represented by the structural formula

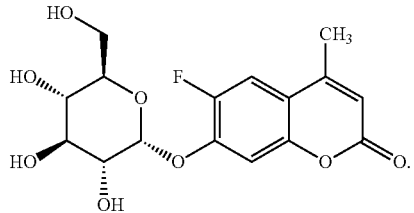 [SMILES: Cc1cc(=O)oc2cc(O[C@H]3O[C@H](CO)[C@@H](O)[C@H](O)[C@H]3O)c(F)cc12]

In a tenth embodiment, the present disclosure provides a self-contained biological sterilization indicator according to any one of the fifth to ninth embodiments, wherein the enzyme substrate is represented by the structural formula

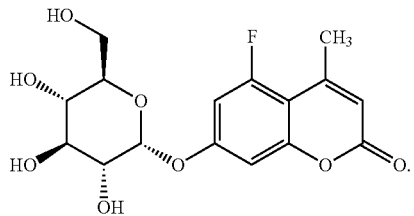 [SMILES: Cc1cc(=O)oc2cc(O[C@H]3O[C@H](CO)[C@@H](O)[C@H](O)[C@H]3O)cc(F)c12]

In an eleventh embodiment, the present disclosure provides a self-contained biological sterilization indicator according to any one of the fifth to tenth embodiments, wherein the mixture has an initial pH in the range from 6.0 to 7.0.

In a twelfth embodiment, the present disclosure provides a biological sterilization indicator comprising a kit containing isolated components comprising:
(i) bacterial spores comprising, and/or capable of producing, an enzyme capable of catalyzing cleavage of an enzyme substrate represented by the structural formula

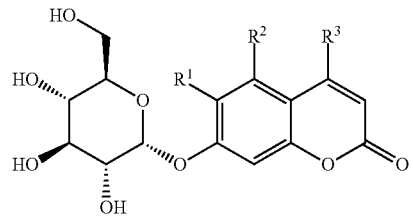

wherein:
one of $R^1$ and $R^2$ is F and the other is H, and
$R^3$ is an alkyl group having from 1 to 12 carbon atoms; and
(ii) a composition, wherein the composition comprises the enzyme substrate, wherein if the composition is brought into contact with the bacterial spores to form a mixture, the mixture will have an initial pH in the range from 6.0 to 9.0.

In a thirteenth embodiment, the present disclosure provides a biological sterilization indicator according to the twelfth embodiment, wherein at least one of components (i) or (ii) is disposed inside a process-challenge device.

In a fourteenth embodiment, the present disclosure provides a biological sterilization indicator according to the twelfth or thirteenth embodiment, wherein $R^3$ is an alkyl group having 1 to 4 carbon atoms.

In a fifteenth embodiment, the present disclosure provides a biological sterilization indicator according to any one of the twelfth to fourteenth embodiments, wherein the composition is a liquid composition.

In a sixteenth embodiment, the present disclosure provides a biological sterilization indicator according to any one of the twelfth to fifteenth embodiments, wherein the enzyme substrate is represented by the structural formula

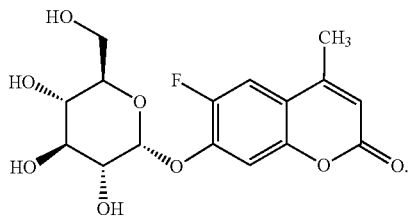 [SMILES: Cc1cc(=O)oc2cc(O[C@H]3O[C@H](CO)[C@@H](O)[C@H](O)[C@H]3O)c(F)cc12]

In a seventeenth embodiment, the present disclosure provides a biological sterilization indicator according to any one of the twelfth to fifteenth embodiments, wherein the enzyme substrate is represented by the structural formula

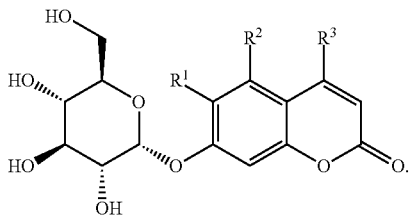

In an eighteenth embodiment, the present disclosure provides a biological sterilization indicator according to any one of the twelfth to seventeenth embodiments, wherein the mixture has an initial pH in the range from 6.0 to 7.0.

In a nineteenth embodiment, the present disclosure provides a method of assessing efficacy of a sterilization process, the method comprising sequentially:
a) providing a biological sterilization indicator comprising:
   bacterial spores comprising, and/or capable of producing, an enzyme capable of catalyzing cleavage of an enzyme substrate represented by the structural formula

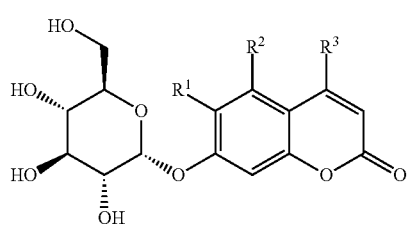

wherein:
one of $R^1$ and $R^2$ is F and the other is H, and
$R^3$ is an alkyl group having from 1 to 12 carbon atoms; and
a composition, wherein the composition comprises the enzyme substrate, wherein if the composition is brought into contact with the bacterial spores to form a mixture, the mixture will have an initial pH in the range from 6.0 to 9.0;

b) subjecting at least the bacterial spores to the sterilization process;

c) contacting the composition with the bacterial spores; and d) evaluating efficacy of the sterilization process.

In a twentieth embodiment, the present disclosure provides a method of assessing efficacy of a sterilization process according to the nineteenth embodiment, wherein step d) comprises fluorescence spectroscopy.

In a twenty-first embodiment, the present disclosure provides a method of assessing efficacy of a sterilization process according to the nineteenth or twentieth embodiment, wherein $R^3$ is an alkyl group having 1 to 4 carbon atoms.

In a twenty-second embodiment, the present disclosure provides a method of assessing efficacy of a sterilization process according to any one of the nineteenth to twenty-first embodiments, wherein the enzyme substrate is represented by the structural formula

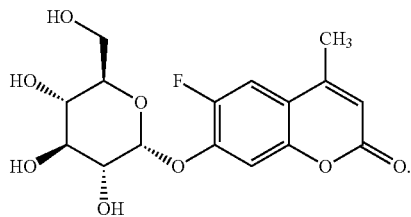

In a twenty-third embodiment, the present disclosure provides a method of assessing efficacy of a sterilization process according to any one of the nineteenth to twenty-first embodiments, wherein the enzyme substrate is represented by the structural formula

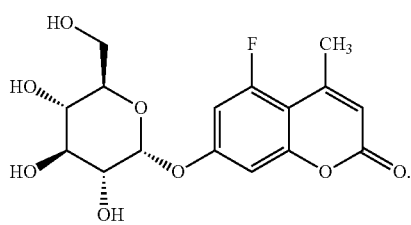 [SMILES: Cc1cc(=O)oc2cc(O[C@H]3O[C@H](CO)[C@@H](O)[C@H](O)[C@H]3O)cc(F)c12]

In a twenty-fourth embodiment, the present disclosure provides a method of assessing efficacy of a sterilization process according to any one of the nineteenth to twenty-third embodiments, wherein the composition and the bacterial spores are both contained within a housing.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

Column chromatography purification of compounds was conducted using an ISOLARA HPFC system (an automated high-performance flash chromatography purification instrument available from Biotage, Inc, Charlottesville, VA). The eluent used for each purification is described in the examples.

Proton nuclear magnetic resonance ($^1$H NMR and $^{19}$F NMR) analyses were conducted using a BRUKER A500 NMR spectrometer (Bruker Corporation, Billerica, MA).

Resorcinol, methanesulfonic acid, β-D-glucose pentaacetate, 4-(dimethylamino)pyridine, and 3,5-dimethoxyfluorobenzene were obtained from Alfa Aesar, Ward Hill, MA.

N-Fluoro-N'-chloromethyltriethylenediaminebis(tetrafluoroborate) (CAS No. 140681-55-6), ethyl acetoacetate, and 2,3,4,5-tetrafluorobenzene were obtained from Oakwood Chemical, Estill, SC.

Tryptone (#BD211705) and yeast extract (#BD212750) were obtained from Becton, Dickinson and Company, Franklin Lakes, NJ.

Deionized water was purified using a MILLI-Q water purification system (EMD Millipore, Burlington, MA).

Suspensions of *Geobacillus stearothermophilus* spores were prepared using molecular biology grade water (#BP2819) obtained from Thermo Fisher Scientific, Waltham, MA.

4'-Methylumbelliferyl-α-D-glucopyranoside (MUG), boron trifluoride etherate, and palladium (10%) on carbon were obtained from the Sigma-Aldrich Company, St. Louis, MO.

Luria-Bertani (LB) broth was prepared by dissolving tryptone (10 g/L), yeast extract (5 g/L), and NaCl (5 g/L) in deionized water. In the examples, 6'-fluoro-4'-methylumbelliferyl α-D-glucopyranoside (0.3 mg/mL) or 5'-fluoro-4'-methylumbelliferyl α-D-glucopyranoside (0.3 mg/mL) was added to the broth. In the comparative examples, 4'-methylumbelliferyl α-D-glucopyranoside (MUG) (0.3 mg/mL) or 6',8'-Difluoro-4'-methylumbelliferyl α-D-glucopyranoside (0.3 mg/mL) was added to the broth. The pH of the broth was adjusted to either pH 6, pH 7, pH 8, or pH 9 using 0.1 N hydrochloric acid or 1N sodium hydroxide solutions. The broth was passed through a 0.22 micron filter prior to use.

Example 1

6'-Fluoro-4'-methylumbelliferyl α-D-glucopyranoside (Enzyme Substrate)

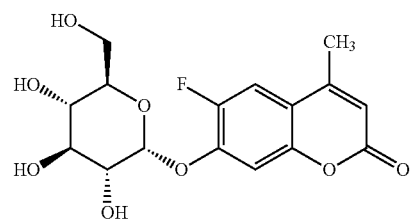 [SMILES: Cc1cc(=O)oc2cc(O[C@H]3O[C@H](CO)[C@@H](O)[C@H](O)[C@H]3O)c(F)cc12]

Part A

Resorcinol (10.13 g, 92.1 mmol) was added to a solution of 1-chloromethyl-4-fluoro-1,4-diazoniabicyclo[2.2.2]octane bis(tetrafluoroborate) (CAS No. 140681-55-6) (39.10 g, 110 mmol) in acetonitrile (800 mL). The reaction was incubated at 4° C. for 48 hours. The solvent was removed using a rotary evaporator. The resulting solid residue was then treated with diethyl ether and stirred for two hours. The remaining solids were removed by filtration and the filtrate was concentrated to give an off-white solid (10.23 g). The product was determined to be a 70:20:10 mixture of 4-fluororesorcinol, 2,4-difluororesorcinol, and 2-fluororesorcinol by $^1$H NMR analysis.

Part B

The reaction mixture from Part A (9.87 g, 77 mmol) was treated with ethyl acetoacetate (9.12 g, 70 mmol) and stirred at 0° C. Methanesulfonic acid (120 mL) was added dropwise over a period of 20 minutes. The solution was stirred for an additional 2 hours and then allowed to warm to ambient temperature overnight. The solution was then poured into deionized water (3 L), forming a precipitate which was isolated by filtration and dried in a vacuum oven to give 9.51 g of a tan powder.

$^1$H NMR indicated that the major product was 6-fluoro-4-methylumbelliferone. $^{19}$F NMR (470 MHz, CD$_3$OD) δ −141.5 (dd, J=11.4, 7.2 Hz). $^1$H NMR (500 MHz, CD$_3$OD) δ 7.48 (d, J=11.4 Hz, 1H), 6.86 (d, J=7.4 Hz, 1H), 6.19 (s, broad, 1H), 2.42 (d, J=1.2 Hz, 3H).

Part C

A 1-L round bottom flask was charged with β-D-glucose pentaacetate (9.29 g, 23.8 mmol), 4-(dimethylamino)pyridine (11.6 g, 95.2 mmol) and 6-fluoro-4-methylumbelliferone (9.29 g, 47.9 mmol). Anhydrous 1,2-dichloroethane (80 mL) was added and the mixture was stirred under an atmosphere of nitrogen. Boron trifluoride etherate (36.8 mL, 298 mmol) was carefully added to the stirred reaction mixture and the reaction was then heated to 60° C. After 2 hours, the reaction mixture was cooled, diluted with dichloromethane and carefully quenched by the addition of a saturated sodium bicarbonate solution. The reaction mixture was filtered through a glass fritted funnel to remove unreacted 6-fluoro-4-methylumbelliferone. The filtrate was placed in a separatory funnel, and the layers were separated. The organic portion was washed with of 1N NaOH solution, followed by washing with water and brine. The organic portion was dried over sodium sulfate, filtered and concentrated. Column chromatography (SiO$_2$, 40-60% ethyl acetate/hexanes) gave 6'-fluoro-4'-methylumbelliferyl-2,3,4,6-tetra-O-acetyl-D-glucopyranoside as a mixture of the alpha and beta anomers. These isomers were separated by column chromatography (SiO$_2$, 5-15% acetone/chloroform) to give 2.77 g of purified 6'-fluoro-4'-methylumbelliferyl 2,3,4,6-tetra-O-acetyl-α-D-glucopyranoside and 0.63 g of purified 6'-fluoro-4'-methylumbelliferyl 2,3,4,6-tetra-O-acetyl-β-D-glucopyranoside both as white powders.

6'-Fluoro-4'-methylumbelliferyl 2,3,4,6-tetra-O-acetyl-α-D-glucopyranoside: $^1$H NMR (500 MHz, CDCl$_3$) δ 7.33 (d, J=10.6 Hz, 1H), 7.21 (d, J=6.8 Hz, 1H), 6.27 (s, 1H), 5.77 (d, J=3.7 Hz, 1H), 5.71 (t, J=9.9 Hz, 1H), 5.17 (dd, J=10.2, 9.5 Hz, 1H), 5.05 (dd, J=10.3, 3.7 Hz, 1H), 4.29 (dd, J=12.3, 5.1 Hz, 1H), 4.22 (ddd, J=10.3, 5.1, 2.0 Hz, 1H), 4.09 (dd, J=12.3, 2.1 Hz, 1H), 2.40 (d, J=1.2 Hz, 3H), 2.12 (s, 3H), 2.09 (s, 3H), 2.07 (s, 3H), 2.06 (s, 3H).

6'-Fluoro-4'-methylumbelliferyl 2,3,4,6-tetra-O-acetyl-β-D-glucopyranoside: $^1$H NMR (500 MHz, CDCl$_3$) δ 7.30 (d, J=10.5 Hz, 1H), 7.16 (d, J=6.8 Hz, 1H), 6.27 (s, 1H), 5.35-5.32 (m, 2H), 5.18 (m, 1H), 5.12 (m, 1H), 4.30 (dd, J=12.4, 5.8 Hz, 1H), 4.20 (dd, J=12.4, 2.3 Hz, 1H), 3.91 (ddd, J=10.0, 5.8, 2.3 Hz, 1H), 2.39 (d, J=1.2 Hz, 3H), 2.15 (s, 3H), 2.09 (s, 3H), 2.07 (s, 3H), 2.05 (s, 3H).

Part D

6'-Fluoro-4'methylumbelliferyl 2,3,4,6-tetra-O-acetyl-α-D-glucopyranoside (2.56 g) was dissolved in 30 mL of anhydrous methanol and treated with 10 drops of 5 M sodium methoxide solution (TCI, Tokyo, Japan). After stirring for 60 minutes, the reaction mixture was concentrated under reduced pressure to give a white solid. The solid was triturated in 10 mL of methanol, filtered, rinsed with a small amount of cold methanol, and dried with suction to give 1.28 g of 6'-fluoro-4'-methylumbelliferyl α-D-glucopyranoside as light green powder. $^1$H NMR (500 MHz, CD$_3$OD) δ 7.59 (d, J=11.2 Hz, 1H), 7.41 (d, J=7.0 Hz, 1H), 6.29 (d, J=1.1 Hz, 1H), 5.74 (d, J=3.7 Hz, 1H), 3.91 (t, J=9.4 Hz, 1H), 3.76 (dd, J=12.1, 2.4 Hz, 1H), 3.72-3.63 (m, 3H), 3.46 (dd, J=9.9, 9.0 Hz, 1H), 2.46 (d, J=1.2 Hz, 3H).

Example 2

5'-Fluoro-4'-methylumbelliferyl α-D-glucopyranoside (Enzyme Substrate)

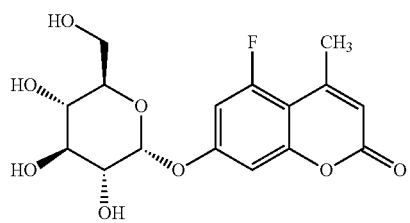 [SMILES: Cc1cc(=O)oc2cc(O[C@H]3O[C@H](CO)[C@@H](O)[C@H](O)[C@H]3O)cc(F)c12]

Part A 3,5-Dimethoxyfluorobenzene (4.36 g, 28 mmol) was dissolved in 25 mL of anhydrous dichloromethane under an atmosphere of nitrogen. A 1.0 M solution of BBr$_3$ in dry dichloromethane (84 mL) was added by syringe over 15 minutes and the resulting reaction mixture was stirred overnight. The reaction mixture was carefully poured into 400 mL of water and stirred at ambient temperature. The mixture was transferred to a separatory funnel and the layers were separated. The aqueous phase was further extracted with diethyl ether (2×200 mL). The organic portions were combined, washed with brine, dried over magnesium sulfate, filtered and concentrated under reduced pressure to give 3.40 g of 5-fluororesorcinol as a solid. $^{19}$F NMR (470 MHz, CD$_3$OD): δ −115.0 (t, J=10.6 Hz). $^1$H NMR (500 MHz, CD$_3$OD): δ 6.05 (td, J=2.0, 0.9 Hz, 1H), 5.98 (dd, J=10.7, 2.1 Hz, 2H).

Part B

5-Fluororesorcinol (3.27 g) was dissolved in ethyl acetoacetate (3.5 g) in an ice bath under a nitrogen atmosphere. Methanesulfonic acid (33 mL) was added dropwise through a pressure equalizing dropping funnel over a period of about 20 minutes. The solution was stirred for 1 hour and then removed from the ice bath and allowed to warm to ambient temperature. The solution was then poured into deionized water (1 L) forming a white precipitate. The precipitate was isolated by filtration and dried under vacuum to give 4.67 g of 5-fluoro-4-methylumbelliferone as a white solid. $^{19}$F NMR (470 MHz, CD$_3$OD): δ −111.61 (m). $^1$H NMR (500 Hz, CD$_3$OD): δ 6.54 (1H, s), 6.52 (dd, J=15.9, 2.4 Hz, 1H), 6.04 (d, J=1.2 Hz, 1H), 2.50 (dd, J=6.2, 1.1 Hz, 3H).

Part C

A 500-mL round bottom flask was charged with β-D-glucose pentaacetate (1.63 g, 4.17 mmol), 4-(dimethylamino)pyridine (1.02 g, 8.34 mmol) and 5-fluoro-4-methyl umbelliferone (0.81 g, 4.17 mmol). Anhydrous 1,2-dichloroethane (15 mL) was added and the mixture was stirred under an atmosphere of nitrogen. Boron trifluoride etherate (3.34 mL, 27.1 mmol) was carefully added to the stirred reaction mixture. The reaction mixture was then heated to 60° C. for 3 hours. The resulting clear yellow solution was cooled to ambient temperature and carefully quenched by the addition of a saturated sodium bicarbonate solution. The reaction mixture was diluted with 50 mL of chloroform followed by addition of 10 mL of 1N NaOH solution and the layers were separated. The organic portion was washed with water and brine, dried over sodium sulfate, filtered, and concentrated. Column chromatography (SiO$_2$, 50% ethyl acetate/hexanes) gave 5'-fluoro-4'-methylumbelliferyl-2,3,4,6-tetra-O-acetyl-D-glucopyranoside as a mixture of the alpha and beta anomers. These isomers were partially separated by column chromatography (SiO$_2$, 5-15% acetone/chloroform) to give 233 mg (white powder) of a mixture of 5'-fluoro-4'-methylumbelliferyl 2,3,4,6-tetra-O-acetyl-α-D-glucopyranoside and 5'-fluoro-4'-methylumbelliferyl 2,3,4,6-tetra-O-acetyl-β-D-glucopyranoside in a 4:1 ratio.

Part D

The mixture of 5'-fluoro-4'-methylumbelliferyl-2,3,4,6-tetra-O-acetyl-α-D-glucopyranoside and 5'-fluoro-4'-methylumbelliferyl-2,3,4,6-tetra-O-acetyl-β-D-pyranoside (233 mg) was dissolved in 5 mL of anhydrous methanol and treated with 2 drops of 5 M sodium methoxide solution. After stirring for 60 minutes, the reaction mixture was concentrated under reduced pressure to give a white solid. Column chromatography (SiO$_2$, 5-20% methanol/chloroform gave 80 mg of 5'-fluoro-4'-methylumbelliferyl D-glucopyranoside as a white powder as a 4:1 ratio of α:β anomers. $^1$H NMR (500 MHz, CD$_3$OD) δ 7.01 (dd, J=1.16, 2.14 Hz, 0.8H), 6.95 (dd, J=2.32, 13.57 Hz, 0.8H), 6.91 (dd, J=1.04, 2.26 Hz, 0.2H), 6.87 (dd, J=2.38, 13.39 Hz, 0.2H), 6.11-6.19 (m, 1H), 5.64 (d, J=3.55 Hz, 0.8H), 5.06 (d, J=7.34 Hz, 0.2H), 3.94 (dd, J=2.20, 12.10 Hz, 0.2H), 3.85 (m, 0.8H), 3.78 (m, 0.8H), 3.68-3.75 (m, 1H), 3.64 (dd, J=3.67, 9.78 Hz, 0.8H), 3.50-3.65 (m, 1.4H), 3.45 (m, 1H), 2.49-2.56 (m, 3H).

Comparative Example A

6',8'-Difluoro-4'-methylumbelliferyl α-D-glucopyranoside (Comparative Enzyme Substrate)

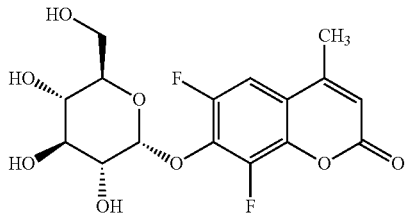 [SMILES: Cc1cc(=O)oc2c(F)c(O[C@H]3O[C@H](CO)[C@@H](O)[C@H](O)[C@H]3O)c(F)cc12]

Part A 2,3,4,5-Tetrafluorobenzene (24.98 g, 0.128 mol) was dissolved in methanol (250 mL) under a nitrogen atmosphere. The stirred solution was cooled in an ice bath. A 5 M solution of sodium methoxide in methanol (60 mL) was slowly added over a period of 3 hours. The resulting mixture was left to warm to ambient temperature overnight. The reaction was then quenched with 26 mL of a 1 M aqueous citric acid solution and the solvent was removed under reduced pressure. Diethyl ether (400 mL) and an additional 100 mL of 1 M citric acid solution were added. The layers were separated and the organic portion was washed successively with 100 mL of 1 M citric acid solution and brine. The organic portion was dried over sodium sulfate, filtered, and concentrated under reduced pressure to give 21.8 g of 2,4-dimethoxy-3,5-difluoronitrobenzene as a brown solid. $^{19}$F NMR (470 MHz, CDCl$_3$) δ −131.8 (m, 1F), −141.6 (d, J=6.1 Hz, 1F). $^1$H NMR (500 MHz, CDCl$_3$) δ 7.53 (dd, J=10.9, 2.3 Hz, 1H), 4.14 (t, J=1.8 Hz, 3H), 4.00 (d, J=0.9 Hz, 3H).

Part B 2,4-Dimethoxy-3,5-difluoronitrobenzene (21.3 g, 0.097 mol) was dissolved in 25 mL of ethyl acetate and the mixture was transferred to a 500 mL Parr hydrogenation bottle. Ethanol (65 mL) was added and the solution degassed for 10 minutes with a stream of nitrogen. Palladium (10%) on carbon (0.96 g) was added and the mixture was shaken under an atmosphere of hydrogen (45 PSI). When hydrogen consumption had ceased, the reaction mixture was filtered through a CELITE pad to yield a brown solution. The solvent was removed under reduced pressure to give 16.6 g of 1-amino-3,5-difluoro-2,4-dimethoxybenzene as a brown oil. $^{19}$F NMR (470 MHz, CDCl$_3$) δ −135.2 (dd, J=11.9 Hz, 4.4 Hz), −149.9 (s). $^1$H NMR (500 MHz, CDCl$_3$) δ 6.26 (dd, J=11.9, 2.2 Hz, 1H), 3.87 (s, 3H), 3.87 (s, 3H), 3.8 (broad s, 2H).

Part C

A stirred suspension of 1-amino-3,5-difluoro-2,4-dimethoxybenzene (16.6 g, 0.088 mol) in a 2:1 mixture of water and concentrated hydrochloric acid was cooled to −5° C. A pre-cooled solution (4° C.) of sodium nitrite (6.39 g, 0.093 mol) dissolved in 15 mL of deionized water was added and the mixture was stirred for 25 minutes. A cooled (10° C.) hypophosphorous acid solution (50% w/w in water, Alfa Aesar) was added in several portions over 6-7 minutes. The reaction mixture was left to warm to ambient temperature overnight providing a red lower phase and a tan/yellow upper phase. The lower phase was removed and water was added, followed by enough 1N NaOH to neutralize the solution. The mixture was extracted 2× with diethyl ether and the combined organic phases were extracted with water (2×), then brine, dried with sodium sulfate, and filtered. The filtrate was concentrated under reduced pressure. The resulting oily residue was dissolved in hexane and filtered through silica gel, extracting with additional hexane during the filtration. The filtration step was repeated. Concentration of the final filtrate under reduced pressure provided 10.53 g of 2,4-difluoro-1,3-dimethoxybenzene as an orange liquid. $^{19}F$ NMR (470 MHz, CDCl$_3$) δ −138.5 (m, 1F), −149.9 (d, J=7.1 Hz, 1F). $^1H$ NMR (500 MHz, CDCl$_3$) δ 6.80 (ddd, J=10.5, 9.4, 2.4 Hz, 1H), 6.58 (dt, J=9.2 Hz, 4.5 Hz, 1H), 4.00 (s, 3H), 3.86 (s, 3H).

Part D 2,4-Difluoro-1,3-dimethoxybenzene (10.21 g, 59 mmol) was dissolved in anhydrous dichloromethane (25 mL) and a 1.0 M solution of BBr$_3$ in dry dichloromethane (180 mL) was added by syringe over 25 minutes. The reaction mixture was stirred overnight, poured into 2 liters of deionized water and then stirred again for about 2 hours. The aqueous mixture was extracted with diethyl ether. The organic fractions were washed with brine, dried over magnesium sulfate, filtered, and concentrated under reduced pressure to yield 6.24 g of 2,4-difluororesorcinol as a tan solid. $^{19}F$ NMR (470 MHz, DMSO-d6) δ −144.5 (p, J=10.6, 4.8-5.3 Hz, 1F), −154.7 (s, 1F). $^1H$ NMR (500 MHz, DMSO-d6) δ 10.0 (s, 1H), 9.6 (s, 1H), 6.7 (ddd, J=18.8, 9.2, 2.3 Hz, 1H), 6.35 (dt, J=9.0, 4.6 Hz, 1H).

Part E 2,4-Difluororesorcinol (5.67 g) was dissolved in ethyl acetoacetate (5.5 mL) in an ice bath. Methanesulfonic acid (100 mL) was added to the solution dropwise over a period of about 30 minutes. The brown solution rapidly turned red in color. The ice bath was removed and the reaction was stirred overnight. The solution was then poured into deionized water. The resulting precipitate was recovered by filtration and then air dried to provide 7.02 g of 6,8-difluoro-4-methylumbelliferone. $^{19}F$ NMR (470 MHz, CD$_3$OD) δ −138.7 (t, J=10.4 Hz, 1F), −154.7 (d, J=9.5 Hz, 1F). $^1H$ NMR (500 MHz, CD$_3$OD) δ 7.35 (dd, J=11.1, 2.2 Hz, 1H), 6.25 (s, 1H), 2.41 (d, J=1.2 Hz, 3H).

Part F

A 500-mL round bottom flask was charged with β-D-glucose pentaacetate (3.90 g, 10.0 mmol), 4-(dimethylamino)pyridine (2.44 g, 20 mmol) and 6,8-difluoro-4-methylumbelliferone (2.12 g, 10.0 mmol). Anhydrous 1,2-dichloroethane (30 mL) was added and the mixture was stirred under an atmosphere of nitrogen. Boron trifluoride etherate (8.02 mL, 65 mmol) was carefully added to the stirred reaction. The reaction mixture was then heated to 60° C. for 2 hours. After cooling to ambient temperature, the reaction was diluted with dichloromethane, and carefully quenched by the addition of a saturated sodium bicarbonate solution. The reaction mixture was placed in a separatory funnel and treated with 20 mL of 1 N NaOH solution. The layers were separated. The organic portion was washed with of 1 N NaOH solution, followed by washing with water and brine. The organic portion was dried over sodium sulfate, filtered and concentrated under reduced pressure. Column chromatography (SiO$_2$, 50% ethyl acetate/hexanes) gave 6',8'-difluoro-4'-methylumbelliferyl-2,3,4,6-tetra-O-acetyl-D-glucopyranoside as a mixture of the alpha and beta anomers. These isomers were separated by column chromatography (SiO$_2$, 5-15% acetone/chloroform) to give 830 mg of purified 6',8'-difluoro-4'-methylumbelliferyl 2,3,4,6-tetra-O-acetyl-α-D-glucopyranoside as a white powder. $^1H$ NMR (500 MHz, CDCl$_3$) δ 7.21 (dd, J=2.02, 10.45 Hz, 1H), 6.40 (d, J=0.98 Hz, 1H), 5.74-5.80 (m, 1H), 5.64 (d, J=3.67 Hz, 1H), 5.24 (t, J=9.90 Hz, 1H), 5.10 (dd, J=3.73, 10.45 Hz, 1H), 4.59-4.66 (m, 1H), 4.30-4.36 (m, 1H), 4.23 (dd, J=2.14, 12.53 Hz, 1H), 2.46 (d, J=1.22 Hz, 3H), 2.22 (s, 3H), 2.14 (s, 2H), 2.14 (s, 2H), 2.13 (s, 3H).

Part G

6',8'-Difluoro-4'-methylumbelliferyl 2,3,4,6-tetra-O-acetyl-α-D-glucopyranoside (399 mg) was dissolved in 8 mL of anhydrous methanol and treated with 2 drops of 5 M sodium methoxide solution. After stirring for 60 minutes, the reaction mixture was concentrated under reduced pressure to give a white solid. Column chromatography (SiO$_2$, 10-20% methanol/chloroform) gave 190 mg of 6',8'-difluoro-4'-methylumbelliferyl α-D-glucopyranoside as a white powder. $^1H$ NMR (500 MHz, CD$_3$OD) 7.48 (dd, J=2.14, 11.31 Hz, 1H), 6.40 (d, J=0.98 Hz, 1H), 5.72 (d, J=3.67 Hz, 1H), 3.97 (td, J=3.47, 10.06 Hz, 1H), 3.92 (t, J=9.48 Hz, 1H), 3.74 (d, J=3.42 Hz, 2H), 3.64 (dd, J=3.67, 9.78 Hz, 1H), 3.48 (t, J=9.60 Hz, 1H), 2.46 (d, J=1.22 Hz, 3H).

Example 3

LB broth (pH 6) containing 6'-fluoro-4'-methylumbelliferyl α-D-glucopyranoside (0.3 mg/mL) (enzyme substrate of Example 1) was added to two wells (100 microliters per well) of a black 96-well microtiter plate with optically clear, flat bottom wells (NUNC #165301, Thermo Fisher Scientific, Waltham, MA). A 5 microliter aqueous suspension containing 5×10$^6$ Geobacillus stearothermophilus spores (ATCC 7953) was added to each well of the microtiter plate. Next, the contents of each well were mixed using a multiple aspiration/delivery sequence with the pipet. Two control wells were also prepared that did not contain any Geobacillus stearothermophilus spores. The top of the plate was covered with an optically clear sealing film (product #4311971, Applied Biosystems Corporation, Foster City, CA). The plate was warmed at 60° C. and shaken in a linear direction. Fluorescence readings (360 nm excitation/450 nm emission at 50% gain) were taken from the bottom of the plate. A reading was taken at an initial time point of 10 seconds and then at +1 minute intervals thereafter. A Synergy Neo2 fluorescence plate reader (BioTek Company, Winooski, VT) was used. In Table 1, the mean fluorescence values detected (RFU) at times of 10 seconds, +5 minutes, +10 minutes, and +30 minutes are reported. The mean fluorescence values detected for the control wells were 978 RFU at 10 seconds; 920 RFU at +5 minutes; 870 RFU at +10 minutes, and 746 RFU at +30 minutes.

Example 4

The procedure of Example 3 was followed, with the exception that the LB broth (pH 6) containing 6'-fluoro-4'-methylumbelliferyl α-D-glucopyranoside (0.3 mg/mL) was replaced with LB broth (pH 6) containing 5'-fluoro-4'-methylumbelliferyl-α-D-glucopyranoside (0.3 mg/mL) (enzyme substrate of Example 2). In Table 1, the mean fluorescence values detected (RFU) at times of 10 seconds, +5 minutes, +10 minutes, and +30 minutes are reported. The mean fluorescence values detected for the control wells were 828 RFU at 10 seconds; 784 RFU at +5 minutes; 738 RFU at +10 minutes, and 622 RFU at +30 minutes.

Comparative Example B

The procedure of Example 3 was followed, with the exception that the LB broth (pH 6) containing 6'-fluoro-4'-methylumbelliferyl α-D-glucopyranoside (0.3 mg/mL) was replaced with LB broth (pH 6) containing 4-methylumbelliferyl α-D-glucopyranoside (0.3 mg/mL) (MUG). In Table 1, the mean fluorescence values detected (RFU) at times of 10 seconds, +5 minutes, +10 minutes, and +30 minutes are reported. The mean fluorescence values detected for the control wells were 868 RFU at 10 seconds; 802 RFU at +5 minutes; 756 RFU at +10 minutes, and 656 RFU at +30 minutes.

Comparative Example C

The procedure of Example 3 was followed, with the exception that the LB broth (pH 6) containing 6'-fluoro-4'-methylumbelliferyl α-D-glucopyranoside (0.3 mg/mL) was replaced with LB broth (pH 6) containing 6',8'-difluoro-4'-methylumbelliferyl α-D-glucopyranoside (0.3 mg/mL) (enzyme substrate of Comparative Example A). In Table 1, the mean fluorescence values detected (RFU) at times of 10 seconds, +5 minutes, +10 minutes, and +30 minutes are reported. The mean fluorescence values detected for the control wells were 1,768 RFU at 10 seconds; 1,750 RFU at +5 minutes; 1,743 RFU at +10 minutes, and 1,805 RFU at +30 minutes.

Table 1, below, reports fluorescence measurements using various enzyme substrates and *Geobacillus stearothermophilus* spores at pH 6.

TABLE 1

| EXAMPLE | pH of LB BROTH | ENZYME SUBSTRATE USED | MEASURED FLUORESCENCE, RFU | | | |
|---|---|---|---|---|---|---|
| | | | 10 sec | +5 min | +10 min | +30 min |
| Example 3 | 6 | Example 1 | 11764 | 30536 | 51188 | 82334 |
| Example 4 | 6 | Example 2 | 1663 | 3559 | 7048 | 20550 |
| Comparative Example B | 6 | MUG | 1590 | 3100 | 5607 | 15915 |
| Comparative Example C | 6 | Comparative Example A | 29807 | 68823 | 85625 | >100000 |

Example 5

LB broth (pH 7) containing 6'-fluoro-4'-methylumbelliferyl α-D-glucopyranoside (0.3 mg/mL) (enzyme substrate of Example 1) was added to two wells (100 microliters per well) of a black 96-well microtiter plate with optically clear, flat bottom wells (NUNC #165301, Thermo Fisher Scientific). A 5 microliter aqueous suspension containing $5 \times 10^6$ *Geobacillus stearothermophilus* spores (ATCC 7953) was added to each well of the microtiter plate. Next, the contents of each well were mixed using a multiple aspiration/delivery sequence with the pipet. Two control wells were also prepared that did not contain any *Geobacillus stearothermophilus* spores. The top of the plate was covered with an optically clear sealing film (product #4311971, Applied Biosystems Corporation). The plate was warmed at 60° C. and shaken in a linear direction. Fluorescence readings (360 nm excitation/450 nm emission at 50% gain) were taken from the bottom of the plate. A reading was taken at an initial time point of 10 seconds and then at +1 minute intervals thereafter. A Synergy Neo2 fluorescence plate reader (BioTek Company) was used. In Table 2, the mean fluorescence values detected (RFU) at times of 10 seconds, +5 minutes, +10 minutes, and +30 minutes are reported. The mean fluorescence values detected for the control wells were 989 RFU at 10 seconds; 936 RFU at +5 minutes; 895 RFU at +10 minutes, and 763 RFU at +30 minutes.

Example 6

The procedure of Example 5 was followed, with the exception that the LB broth (pH 7) containing 6'-fluoro-4'-methylumbelliferyl α-D-glucopyranoside (0.3 mg/mL) was replaced with LB broth (pH 7) containing 5'-fluoro-4'-methylumbelliferyl α-D-glucopyranoside (0.3 mg/mL) (enzyme substrate of Example 2). In Table 2, the mean fluorescence values detected (RFU) at times of 10 seconds, +5 minutes, +10 minutes, and +30 minutes are reported. The mean fluorescence values detected for the control wells were 720 RFU at 10 seconds; 679 RFU at +5 minutes; 646 RFU at +10 minutes, and 547 RFU at +30 minutes.

Comparative Example C

The procedure of Example 5 was followed, with the exception that the LB broth (pH 7) containing 6'-fluoro-4'-methylumbelliferyl α-D-glucopyranoside (0.3 mg/mL) was replaced with LB broth (pH 7) containing 4-methylumbelliferyl α-D-glucopyranoside (0.3 mg/mL) (MUG). In Table 2, the mean fluorescence values detected (RFU) at times of 10 seconds, +5 minutes, +10 minutes, and +30 minutes are reported. The mean fluorescence values detected for the control wells were 722 RFU at 10 seconds; 670 RFU at +5 minutes; 636 RFU at +10 minutes, and 557 RFU at +30 minutes.

Comparative Example D

The procedure of Example 5 was followed, with the exception that the LB broth (pH 7) containing 6'-fluoro-4'-methylumbelliferyl α-D-glucopyranoside (0.3 mg/mL) was replaced with LB broth (pH 7) containing 6',8'-difluoro-4'-methylumbelliferyl α-D-glucopyranoside (0.3 mg/mL) (enzyme substrate of Comparative Example A). In Table 2, the mean fluorescence values detected (RFU) at times of 10 seconds, +5 minutes, +10 minutes, and +30 minutes are reported. The mean fluorescence values detected for the control wells were 1,536 RFU at 10 seconds; 1,519 RFU at +5 minutes; 1,508 RFU at +10 minutes, and 1,439 RFU at +30 minutes.

Table 2, below reports fluorescence measurements using various enzyme substrates and *Geobacillus stearothermophilus* spores at pH 7.

TABLE 2

| EXAMPLE | pH of LB BROTH | ENZYME SUBSTRATE USED | MEASURED FLUORESCENCE, RFU | | | |
|---|---|---|---|---|---|---|
| | | | 10 sec | +5 min | +10 min | +30 min |
| Example 5 | 7 | Example 1 | 24718 | 54317 | 79851 | >100000 |
| Example 6 | 7 | Example 2 | 5842 | 15059 | 28596 | 58390 |
| Comparative Example C | 7 | MUG | 3298 | 7944 | 15511 | 41643 |
| Comparative Example D | 7 | Comparative Example A | 32795 | 67118 | 89943 | >100000 |

Example 7

LB broth (pH 8) containing 6'-fluoro-4'-methylumbelliferyl α-D-glucopyranoside (0.3 mg/mL) (enzyme substrate of Example 1) was added to two wells (100 microliters per well) of a black 96-well microtiter plate with optically clear, flat bottom wells (NUNC #165301, Thermo Fisher Scientific). A 5 microliter aqueous suspension containing $5 \times 10^6$ *Geobacillus stearothermophilus* spores (ATCC 7953) was added to each well of the microtiter plate. Next, the contents of each well were mixed using a multiple aspiration/delivery sequence with the pipet. Two control wells were also prepared that did not contain any *Geobacillus stearothermophilus* spores. The top of the plate was covered with an optically clear sealing film (product #4311971, Applied Biosystems Corporation). The plate was warmed at 60° C. and shaken in a linear direction. Fluorescence readings (360 nm excitation/450 nm emission at 50% gain) were taken from the bottom of the plate. A reading was taken at an initial time point of 10 seconds and then at +1 minute intervals thereafter. A Synergy Neo2 fluorescence plate reader (BioTek Company) was used. In Table 3, the mean fluorescence values detected (RFU) at times of 10 seconds, +5 minutes, +10 minutes, and +30 minutes are reported. The mean fluorescence values detected for the control wells were 940 RFU at 10 seconds; 884 RFU at +5 minutes; 845 RFU at +10 minutes, and 723 RFU at +30 minutes.

Example 8

The procedure of Example 7 was followed, with the exception that the LB broth (pH 8) containing 6'-fluoro-4'-methylumbelliferyl α-D-glucopyranoside (0.3 mg/mL) was replaced with LB broth (pH 8) containing 5'-fluoro-4'-methylumbelliferyl α-D-glucopyranoside (0.3 mg/mL) (enzyme substrate of Example 2). In Table 3, the mean fluorescence values detected (RFU) at times of 10 seconds, +5 minutes, +10 minutes, and +30 minutes are reported. The mean fluorescence values detected for the control wells were 616 RFU at 10 seconds; 573 RFU at +5 minutes; 538 RFU at +10 minutes, and 455 RFU at +30 minutes.

Comparative Example E

The procedure of Example 7 was followed, with the exception that the LB broth (pH 8) containing 6'-fluoro-4'-methylumbelliferyl α-D-glucopyranoside (0.3 mg/mL) was replaced with LB broth (pH 8) containing 4-methylumbelliferyl α-D-glucopyranoside (0.3 mg/mL) (MUG). In Table 3, the mean fluorescence values detected (RFU) at times of 10 seconds, +5 minutes, +10 minutes, and +30 minutes are reported. The mean fluorescence values detected for the control wells were 628 RFU at 10 seconds; 569 RFU at +5 minutes; 535 RFU at +10 minutes, and 463 RFU at +30 minutes.

Comparative Example F

The procedure of Example 7 was followed, with the exception that the LB broth (pH 8) containing 6'-fluoro-4'-methylumbelliferyl α-D-glucopyranoside (0.3 mg/mL) was replaced with LB broth (pH 8) containing 6',8'-difluoro-4'-methylumbelliferyl α-D-glucopyranoside (0.3 mg/mL) (enzyme substrate of Comparative Example A). In Table 3, the mean fluorescence values detected (RFU) at times of 10 seconds, +5 minutes, +10 minutes, and +30 minutes are reported. The mean fluorescence values detected for the control wells were 2,547 RFU at 10 seconds; 2,601 RFU at +5 minutes; 2,666 RFU at +10 minutes, and 3,020 RFU at +30 minutes.

Table 3, below, reports fluorescence measurements using various enzyme substrates and *Geobacillus stearothermophilus* spores at pH 8.

TABLE 3

| EXAMPLE | pH of LB BROTH | ENZYME SUBSTRATE USED | MEASURED FLUORESCENCE, RFU | | | |
|---|---|---|---|---|---|---|
| | | | 10 sec | +5 min | +10 min | +30 min |
| Example 7 | 8 | Example 1 | 11298 | 32225 | 61862 | >100000 |
| Example 8 | 8 | Example 2 | 3928 | 11692 | 26273 | 66491 |
| Comparative Example E | 8 | MUG | 3450 | 9572 | 21171 | 64484 |

TABLE 3-continued

| EXAMPLE | pH of LB BROTH | ENZYME SUBSTRATE USED | MEASURED FLUORESCENCE, RFU | | | |
|---|---|---|---|---|---|---|
| | | | 10 sec | +5 min | +10 min | +30 min |
| Comparative Example F | 8 | Comparative Example A | 20878 | 48312 | 77765 | >100000 |

Example 9

LB broth (pH 9) containing 6'-fluoro-4'-methylumbelliferyl α-D-glucopyranoside (0.3 mg/mL) (enzyme substrate of Example 1) was added to two wells (100 microliters per well) of a black 96-well microtiter plate with optically clear, flat bottom wells (NUNC #165301, Thermo Fisher Scientific). A 5 microliter aqueous suspension containing $5 \times 10^6$ Geobacillus stearothermophilus spores (ATCC 7953) was added to each well of the microtiter plate. Next, the contents of each well were mixed using a multiple aspiration/delivery sequence with the pipet. Two control wells were also prepared that did not contain any Geobacillus stearothermophilus spores. The top of the plate was covered with an optically clear sealing film (product #4311971, Applied Biosystems Corporation). The plate was warmed at 60° C. and shaken in a linear direction. Fluorescence readings (360 nm excitation/450 nm emission at 50% gain) were taken from the bottom of the plate. A reading was taken at an initial time point of 10 seconds and then at +1 minute intervals thereafter. A Synergy Neo2 fluorescence plate reader (BioTek Company) was used. In Table 4, the mean fluorescence values detected (RFU) at times of 10 seconds, +5 minutes, +10 minutes, and +30 minutes are reported. The mean fluorescence values detected for the control wells were 825 RFU at 10 seconds; 772 RFU at +5 minutes; 738 RFU at +10 minutes, and 633 RFU at +30 minutes.

Example 10

The procedure of Example 9 was followed, with the exception that the LB broth (pH 9) containing 6'-fluoro-4'-methylumbelliferyl α-D-glucopyranoside (0.3 mg/mL) was replaced with LB broth (pH 9) containing 5'-fluoro-4'-methylumbelliferyl α-D-glucopyranoside (0.3 mg/mL) (enzyme substrate of Example 2). In Table 4, the mean fluorescence values detected (RFU) at times of 10 seconds, +5 minutes, +10 minutes, and +30 minutes are reported. The mean fluorescence values detected for the control wells were 501 RFU at 10 seconds; 449 RFU at +5 minutes; 421 RFU at +10 minutes, and 365 RFU at +30 minutes.

Comparative Example G

The procedure of Example 9 was followed, with the exception that the LB broth (pH 9) containing 6'-fluoro-4'-methylumbelliferyl α-D-glucopyranoside (0.3 mg/mL) was replaced with LB broth (pH 9) containing 4-methylumbelliferyl α-D-glucopyranoside (0.3 mg/mL) (MUG). In Table 4, the mean fluorescence values detected (RFU) at times of 10 seconds, +5 minutes, +10 minutes, and +30 minutes are reported. The mean fluorescence values detected for the control wells were 494 RFU at 10 seconds; 436 RFU at +5 minutes; 406 RFU at +10 minutes, and 338 RFU at +30 minutes.

Comparative Example H

The procedure of Example 9 was followed, with the exception that the LB broth (pH 9) containing 6'-fluoro-4'-methylumbelliferyl α-D-glucopyranoside (0.3 mg/mL) was replaced with LB broth (pH 9) containing 6',8'-difluoro-4'-methylumbelliferyl α-D-glucopyranoside (0.3 mg/mL) (enzyme substrate of Comparative Example A). In Table 4, the mean fluorescence values detected (RFU) at times of 10 seconds, +5 minutes, +10 minutes, and +30 minutes are reported. The mean fluorescence values detected for the control wells were 1,381 RFU at 10 seconds; 1,397 RFU at +5 minutes; 1,496 RFU at +10 minutes, and 2,521 RFU at +30 minutes.

Table 4, below, reports fluorescence measurements using various enzyme substrates and Geobacillus stearothermophilus spores at pH 9.

TABLE 4

| EXAMPLE | pH of LB BROTH | ENZYME SUBSTRATE USED | MEASURED FLUORESCENCE, RFU | | | |
|---|---|---|---|---|---|---|
| | | | 10 sec | +5 min | +10 min | +30 min |
| Example 9 | 9 | Example 1 | 2823 | 8863 | 22809 | 77125 |
| Example 10 | 9 | Example 2 | 1116 | 3002 | 7983 | 43732 |
| Comparative Example G | 9 | MUG | 1193 | 3444 | 9258 | 48874 |
| Comparative Example H | 9 | Comparative Example A | 4119 | 12620 | 31290 | 77404 |

Example 11

An 800-microliter sample of LB broth (pH 6) containing 6'-fluoro-4'-methylumbelliferyl α-D-glucopyranoside (0.3 mg/mL) (enzyme substrate of Example 1) was added to a 1.5 mL microcentrifuge tube and the capped tube was placed in a heating block at 100° C. for 15 minutes. A metal block was placed on top of the tube to keep the cap sealed during heating. The sample was cooled to ambient temperature and then added to two wells (100 microliters per well) of a black 96-well microtiter plate with optically clear, flat bottom wells (NUNC #165301, Thermo Fisher Scientific). The top of the plate was covered with an optically clear sealing film (product #4311971, Applied Biosystems Corporation). The plate was warmed at 60° C. and shaken in a linear direction. Fluorescence readings (360 nm excitation/450 nm emission at 50% gain) were taken from the bottom of the plate. A reading was taken at an initial time point of 10 seconds and then at +1 minute intervals thereafter. A Synergy Neo2 fluorescence plate reader (BioTek Company) was used. In Table 5, the mean fluorescence values detected (RFU) at times of 10 seconds, +5 minutes, +10 minutes, and +30 minutes are reported.

Example 12

The procedure of Example 11 was followed, with the exception that the LB broth (pH 6) containing 6'-fluoro-4'-methylumbelliferyl α-D-glucopyranoside (0.3 mg/mL) was replaced with LB broth (pH 6) containing 5'-fluoro-4'-methylumbelliferyl α-D-glucopyranoside (0.3 mg/mL) (enzyme substrate of Example 2). In Table 5, the mean fluorescence values detected (RFU) at times of 10 seconds, +5 minutes, +10 minutes, and +30 minutes are reported.

Comparative Example I

The procedure of Example 11 was followed, with the exception that the LB broth (pH 6) containing 6'-fluoro-4'-methylumbelliferyl α-D-glucopyranoside (0.3 mg/mL) was replaced with LB broth (pH 6) containing 4-methylumbelliferyl α-D-glucopyranoside (0.3 mg/mL) (MUG). In Table 5, the mean fluorescence values detected (RFU) at times of 10 seconds, +5 minutes, +10 minutes, and +30 minutes are reported.

Comparative Example J

The procedure of Example 11 was followed, with the exception that the LB broth (pH 6) containing 6'-fluoro-4'-methylumbelliferyl α-D-glucopyranoside (0.3 mg/mL) was replaced with LB broth (pH 6) containing 6',8'-difluoro-4'-methylumbelliferyl α-D-glucopyranoside (0.3 mg/mL) (enzyme substrate of Comparative Example A). In Table 5, the mean fluorescence values detected (RFU) at times of 10 seconds, +5 minutes, +10 minutes, and +30 minutes are reported.

Table 5, below, reports measurement of enzyme substrate degradation (pH 6, 100° C. for 15 minutes).

TABLE 5

| EXAMPLE | pH of LB BROTH | ENZYME SUBSTRATE USED | MEASURED FLUORESCENCE, RFU | | | |
|---|---|---|---|---|---|---|
| | | | 10 sec | +5 min | +10 min | +30 min |
| Example 11 | 6 | Example 1 | 1108 | 1096 | 1040 | 948 |
| Example 12 | 6 | Example 2 | 933 | 852 | 805 | 758 |
| Comparative Example I | 6 | MUG | 967 | 909 | 852 | 782 |
| Comparative Example J | 6 | Comparative Example A | 10,605 | 10,851 | 10,748 | 10,663 |

Example 13

An 800-microliter sample of LB broth (pH 7) containing 6'-fluoro-4'-methylumbelliferyl α-D-glucopyranoside (0.3 mg/mL) (enzyme substrate of Example 1) was added to a 1.5 mL microcentrifuge tube and the capped tube was placed in a heating block at 100° C. for 15 minutes. A metal block was placed on top of the tube to keep the cap sealed during heating. The sample was cooled to ambient temperature and then added to two wells (100 microliters per well) of a black 96-well microtiter plate with optically clear, flat bottom wells (NUNC #165301, Thermo Fisher Scientific). The top of the plate was covered with an optically clear sealing film (product #4311971, Applied Biosystems Corporation). The plate was warmed at 60° C. and shaken in a linear direction. Fluorescence readings (360 nm excitation/450 nm emission at 50% gain) were taken from the bottom of the plate. A reading was taken at an initial time point of 10 seconds and then at +1 minute intervals thereafter. A Synergy Neo2 fluorescence plate reader (BioTek Company) was used. In Table 6, the mean fluorescence values detected (RFU) at times of 10 seconds, +5 minutes, +10 minutes, and +30 minutes are reported.

Example 14

The procedure of Example 13 was followed, with the exception that the LB broth (pH 7) containing 6'-fluoro-4'-methylumbelliferyl α-D-glucopyranoside (0.3 mg/mL) was replaced with LB broth (pH 7) containing 5'-fluoro-4'-methylumbelliferyl α-D-glucopyranoside (0.3 mg/mL) (enzyme substrate of Example 2). In Table 6, the mean fluorescence values detected (RFU) at times of 10 seconds, +5 minutes, +10 minutes, and +30 minutes are reported.

Comparative Example K

The procedure of Example 13 was followed, with the exception that the LB broth (pH 7) containing 6'-fluoro-4'-methylumbelliferyl α-D-glucopyranoside (0.3 mg/mL) was replaced with LB broth (pH 7) containing 4-methylumbelliferyl α-D-glucopyranoside (0.3 mg/mL) (MUG). In Table 6, the mean fluorescence values detected (RFU) at times of 10 seconds, +5 minutes, +10 minutes, and +30 minutes are reported.

Comparative Example L

The procedure of Example 13 was followed, with the exception that the LB broth (pH 7) containing 6'-fluoro-4'-methylumbelliferyl α-D-glucopyranoside (0.3 mg/mL) was replaced with LB broth (pH 7) containing 6',8'-difluoro-4'-methylumbelliferyl α-D-glucopyranoside (0.3 mg/mL) (enzyme substrate of Comparative Example A). In Table 6, the mean fluorescence values detected (RFU) at times of 10 seconds, +5 minutes, +10 minutes, and +30 minutes are reported.

Table 6, below reports measurement of enzyme substrate degradation (pH 7, 100° C. for 15 minutes).

TABLE 6

| EXAMPLE | pH of LB BROTH | ENZYME SUBSTRATE USED | MEASURED FLUORESCENCE, RFU | | | |
|---|---|---|---|---|---|---|
| | | | 10 sec | +5 min | +10 min | +30 min |
| Example 13 | 7 | Example 1 | 1209 | 1183 | 1130 | 1037 |
| Example 14 | 7 | Example 2 | 831 | 777 | 733 | 673 |
| Comparative Example K | 7 | MUG | 823 | 790 | 745 | 670 |
| Comparative Example L | 7 | Comparative Example A | 12986 | 13409 | 13403 | 13283 |

Example 15

An 800-microliter sample of LB broth (pH 8) containing 6'-fluoro-4'-methylumbelliferyl α-D-glucopyranoside (0.3 mg/mL) (enzyme substrate of Example 1) was added to a 1.5 mL microcentrifuge tube and the capped tube was placed in a heating block at 100° C. for 15 minutes. A metal block was placed on top of the tube to keep the cap sealed during heating. The sample was cooled to ambient temperature and then added to two wells (100 microliters per well) of a black 96-well microtiter plate with optically clear, flat bottom wells (NUNC #165301, Thermo Fisher Scientific). The top of the plate was covered with an optically clear sealing film (product #4311971, Applied Biosystems Corporation). The plate was warmed at 60° C. and shaken in a linear direction. Fluorescence readings (360 nm excitation/450 nm emission at 50% gain) were taken from the bottom of the plate. A reading was taken at an initial time point of 10 seconds and then at +1 minute intervals thereafter. A Synergy Neo2 fluorescence plate reader (BioTek Company) was used. In Table 7, the mean fluorescence values detected (RFU) at times of 10 seconds, +5 minutes, +10 minutes, and +30 minutes are reported.

Example 16

The procedure of Example 15 was followed, with the exception that the LB broth (pH 8) containing 6'-fluoro-4'-methylumbelliferyl α-D-glucopyranoside (0.3 mg/mL) was replaced with LB broth (pH 8) containing 5'-fluoro-4'-methylumbelliferyl α-D-glucopyranoside (0.3 mg/mL) (enzyme substrate of Example 2). In Table 7, the mean fluorescence values detected (RFU) at times of 10 seconds, +5 minutes, +10 minutes, and +30 minutes are reported.

Comparative Example M

The procedure of Example 15 was followed with the exception that the LB broth (pH 8) containing 6'-fluoro-4'-methylumbelliferyl α-D-glucopyranoside (0.3 mg/mL) was replaced with LB broth (pH 8) containing 4-methylumbelliferyl α-D-glucopyranoside (0.3 mg/mL) (MUG). In Table 7, the mean fluorescence values detected (RFU) at times of 10 seconds, +5 minutes, +10 minutes, and +30 minutes are reported.

Comparative Example N

The procedure of Example 15 was followed, with the exception that the LB broth (pH 8) containing 6'-fluoro-4'-methylumbelliferyl α-D-glucopyranoside (0.3 mg/mL) was replaced with LB broth (pH 8) containing 6',8'-difluoro-4'-methylumbelliferyl α-D-glucopyranoside (0.3 mg/mL) (enzyme substrate of Comparative Example A). In Table 7, the mean fluorescence values detected (RFU) at times of 10 seconds, +5 minutes, +10 minutes, and +30 minutes are reported.

Table 7, below, reports measurement of enzyme substrate degradation (pH 8, 100° C. for 15 minutes).

TABLE 7

| EXAMPLE | pH of LB BROTH | ENZYME SUBSTRATE USED | MEASURED FLUORESCENCE, RFU | | | |
|---|---|---|---|---|---|---|
| | | | 10 sec | +5 min | +10 min | +30 min |
| Example 15 | 8 | Example 1 | 1145 | 1130 | 1092 | 1026 |
| Example 16 | 8 | Example 2 | 748 | 705 | 658 | 579 |
| Comparative Example M | 8 | MUG | 714 | 685 | 643 | 567 |
| Comparative Example N | 8 | Comparative Example A | 14015 | 14483 | 14494 | 14331 |

Example 17

An 800-microliter sample of LB broth (pH 9) containing 6'-fluoro-4'-methylumbelliferyl α-D-glucopyranoside (0.3 mg/mL) (enzyme substrate of Example 1) was added to a 1.5 mL microcentrifuge tube and the capped tube was placed in a heating block at 100° C. for 15 minutes. A metal block was placed on top of the tube to keep the cap sealed during heating. The sample was cooled to ambient temperature and then added to two wells (100 microliters per well) of a black 96-well microtiter plate with optically clear, flat bottom wells (NUNC #165301, Thermo Fisher Scientific). The top of the plate was covered with an optically clear sealing film (product #4311971, Applied Biosystems Corporation). Fluorescence readings (360 nm excitation/450 nm emission at 50% gain) were taken from the bottom of the plate at 60° C. and with linear shaking of the plate. A reading was taken at an initial time point of 10 seconds and then at +1 minute intervals thereafter. A Synergy Neo2 fluorescence plate reader (BioTek Company) was used. In Table 8, the mean fluorescence values detected (RFU) at times of 10 seconds, +5 minutes, +10 minutes, and +30 minutes are reported.

Example 18

The procedure of Example 17 was followed, with the exception that the LB broth (pH 9) containing 6'-fluoro-4'-methylumbelliferyl α-D-glucopyranoside (0.3 mg/mL) was replaced with LB broth (pH 9) containing 5'-fluoro-4'-methylumbelliferyl α-D-glucopyranoside (0.3 mg/mL) (enzyme substrate of Example 2). In Table 8, the mean fluorescence values detected (RFU) at times of 10 seconds, +5 minutes, +10 minutes, and +30 minutes are reported.

Comparative Example O

The procedure of Example 17 was followed, with the exception that the LB broth (pH 9) containing 6'-fluoro-4'-methylumbelliferyl α-D-glucopyranoside (0.3 mg/mL) was replaced with LB broth (pH 9) containing 4-methylumbelliferyl α-D-glucopyranoside (0.3 mg/mL) (MUG). In Table 8, the mean fluorescence values detected (RFU) at times of 10 seconds, +5 minutes, +10 minutes, and +30 minutes are reported.

Comparative Example P

The procedure of Example 17 was followed, with the exception that the LB broth (pH 9) containing 6'-fluoro-4'-methylumbelliferyl α-D-glucopyranoside (0.3 mg/mL) was replaced with LB broth (pH 9) containing 6',8'-difluoro-4'-methylumbelliferyl α-D-glucopyranoside (0.3 mg/mL) (enzyme substrate of Comparative Example A). In Table 8, the mean fluorescence values detected (RFU) at times of 10 seconds, +5 minutes, +10 minutes, and +30 minutes are reported.

Table 8, below, reports measurement of enzyme substrate degradation (pH 9, 100° C. for 15 minutes).

TABLE 8

| EXAMPLE | pH of LB BROTH | ENZYME SUBSTRATE USED | MEASURED FLUORESCENCE, RFU | | | |
|---|---|---|---|---|---|---|
| | | | 10 sec | +5 min | +10 min | +30 min |
| Example 17 | 9 | Example 1 | 1449 | 1437 | 1388 | 1330 |
| Example 18 | 9 | Example 2 | 675 | 625 | 584 | 530 |
| Comparative Example O | 9 | MUG | 654 | 622 | 575 | 500 |
| Comparative Example P | 9 | Comparative Example A | 18584 | 19052 | 18990 | 18683 |

The preceding description, given in order to enable one of ordinary skill in the art to practice the claimed disclosure, is not to be construed as limiting the scope of the disclosure, which is defined by the claims and all equivalents thereto.

What is claimed is:

1. A fluorinated 4'-alkylumbelliferyl α-D-glucopyranoside represented by the structural formula

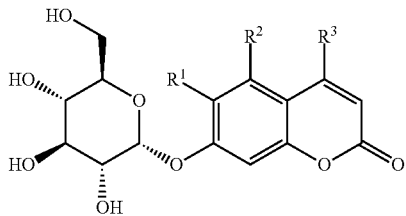

wherein:
one of $R^1$ and $R^2$ is F and the other is H, and
$R^3$ is an alkyl group having from 1 to 12 carbon atoms.

2. The fluorinated 4'-alkylumbelliferyl α-D-glucopyranoside of claim 1, wherein $R^3$ is an alkyl group having 1 to 4 carbon atoms.

3. The fluorinated 4'-alkylumbelliferyl α-D-glucopyranoside of claim 1, wherein $R^1$ is F, $R^2$ is H, and $R^3$ is methyl.

4. The fluorinated 4'-alkylumbelliferyl α-D-glucopyranoside of claim 1, wherein $R^1$ is H, $R^2$ is F, and $R^3$ is methyl.

5. A self-contained biological sterilization indicator comprising:
a housing,
bacterial spores comprising, and/or capable of producing, an enzyme capable of catalyzing cleavage of an enzyme substrate represented by the structural formula

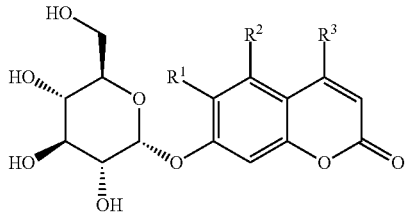

wherein:
one of $R^1$ and $R^2$ is F and the other is H, and
$R^3$ is an alkyl group having from 1 to 12 carbon atoms; and a frangible container containing a composition, wherein the composition comprises the enzyme substrate, wherein if the frangible container is broken the composition will contact the bacterial spores to form a mixture having an initial pH in the range from 6.0 to 9.0.

6. The self-contained biological sterilization indicator of claim 5, wherein the self-contained biological sterilization indicator is disposed inside a process-challenge device.

7. The self-contained biological sterilization indicator of claim 5, wherein $R^3$ is an alkyl group having 1 to 4 carbon atoms.

8. The self-contained biological sterilization indicator of claim 5, wherein the self-contained biological sterilization indicator is capable of determining efficacy of two or more cycles chosen from the powerset of 121 gravity, 121 pre-vac, 121 SFPP, 132 gravity, 132 pre-vac, 132 SFPP, 134 pre-vac, 134 SFPP, 135 gravity, 135 pre-vac, and 135 SFPP.

9. The self-contained biological sterilization indicator of claim 5, wherein the enzyme substrate is represented by the structural formula

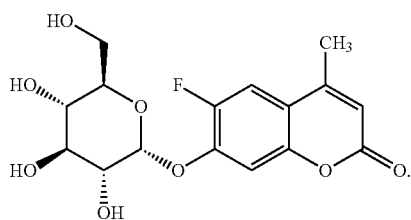 [SMILES: Cc1cc(=O)oc2cc(O[C@H]3O[C@H](CO)[C@@H](O)[C@H](O)[C@H]3O)c(F)cc12]

10. The self-contained biological sterilization indicator of claim 5, wherein the enzyme substrate is represented by the structural formula

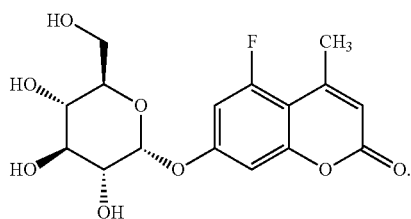 [SMILES: Cc1cc(=O)oc2cc(O[C@H]3O[C@H](CO)[C@@H](O)[C@H](O)[C@H]3O)cc(F)c12]

11. The self-contained biological sterilization indicator of claim 5, wherein the mixture has an initial pH in the range from 6.0 to 7.0.

12. A biological sterilization indicator comprising a kit containing isolated components comprising:
(i) bacterial spores comprising, and/or capable of producing, an enzyme capable of catalyzing cleavage of an enzyme substrate represented by the structural formula

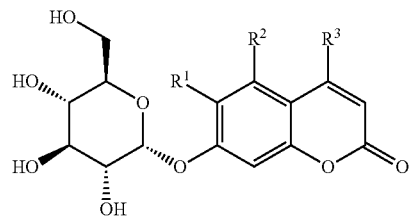

wherein:
one of $R^1$ and $R^2$ is F and the other is H, and $R^3$ is an alkyl group having from 1 to 12 carbon atoms; and
(ii) a composition, wherein the composition comprises the enzyme substrate, wherein if the composition is brought into contact with the bacterial spores to form a mixture, the mixture will have an initial pH in the range from 6.0 to 9.0.

13. The biological sterilization indicator of claim 12, wherein at least one of components (i) or (ii) is disposed inside a process-challenge device.

14. The biological sterilization indicator of claim 12, wherein $R^3$ is an alkyl group having 1 to 4 carbon atoms.

15. The biological sterilization indicator of claim 12, wherein the composition is a liquid composition.

16. The biological sterilization indicator of claim 12, wherein the enzyme substrate is represented by the structural formula

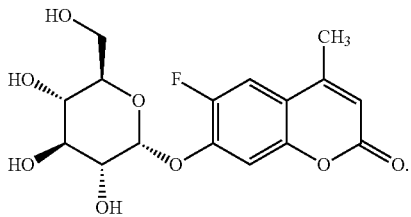 [SMILES: Cc1cc(=O)oc2cc(O[C@H]3O[C@H](CO)[C@@H](O)[C@H](O)[C@H]3O)c(F)cc12]

17. The biological sterilization indicator of claim 12, wherein the enzyme substrate is represented by the structural formula

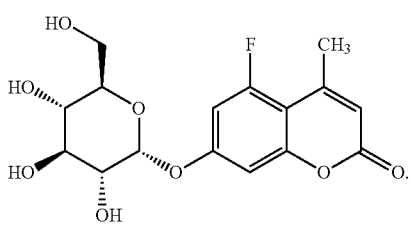 [SMILES: Cc1cc(=O)oc2cc(O[C@H]3O[C@H](CO)[C@@H](O)[C@H](O)[C@H]3O)cc(F)c12]

18. The biological sterilization indicator of claim 12, wherein the mixture has an initial pH in the range from 6.0 to 7.0.

19. A method of assessing efficacy of a sterilization process, the method comprising sequentially:
a) providing a biological sterilization indicator comprising:
bacterial spores comprising, and/or capable of producing, an enzyme capable of catalyzing cleavage of an enzyme substrate represented by the structural formula

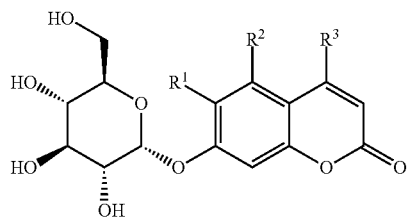

wherein:
one of $R^1$ and $R^2$ is F and the other is H, and $R^3$ is an alkyl group having from 1 to 12 carbon atoms; and
a composition, wherein the composition comprises the enzyme substrate, wherein if the composition is brought into contact with the bacterial spores to form a mixture, the mixture will have an initial pH in the range from 6.0 to 9.0;

b) subjecting at least the bacterial spores to the sterilization process;
c) contacting the composition with the bacterial spores; and
d) evaluating efficacy of the sterilization process.

20. The method of claim 19, wherein step d) comprises fluorescence spectroscopy.

21. The method of claim 19, wherein $R^3$ is an alkyl group having 1 to 4 carbon atoms.

22. The method of claim 19, wherein the enzyme substrate is represented by the structural formula

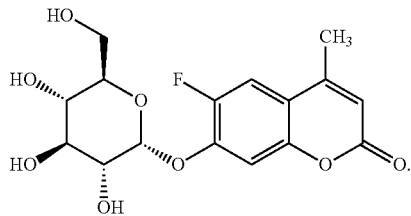 [SMILES: Cc1cc(=O)oc2cc(O[C@H]3O[C@H](CO)[C@@H](O)[C@H](O)[C@H]3O)c(F)cc12]

23. The method of claim 19, wherein the enzyme substrate is represented by the structural formula

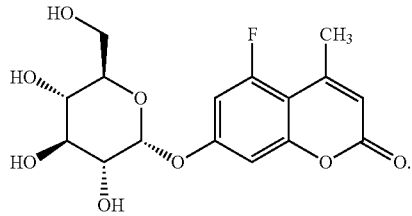 [SMILES: Cc1cc(=O)oc2cc(O[C@H]3O[C@H](CO)[C@@H](O)[C@H](O)[C@H]3O)cc(F)c12]

24. The method of claim 19, wherein the composition and the bacterial spores are both contained within a housing.

* * * * *